(12) United States Patent
Khairkhahan et al.

(10) Patent No.: US 9,597,514 B2
(45) Date of Patent: Mar. 21, 2017

(54) EPICARDIAL HEART RHYTHM MANAGEMENT DEVICES, SYSTEMS AND METHODS

(71) Applicant: Vquad Medical, Palo Alto, CA (US)

(72) Inventors: Alex Khairkhahan, Palo Alto, CA (US); Sebastian Khairkhahan, Palo Alto, CA (US)

(73) Assignee: VQUAD MEDICAL, Palo Alto, CA (US)

( * ) Notice: Subject to any disclaimer, the term of this patent is extended or adjusted under 35 U.S.C. 154(b) by 0 days.

(21) Appl. No.: 14/960,943

(22) Filed: Dec. 7, 2015

(65) Prior Publication Data

US 2016/0158545 A1    Jun. 9, 2016

Related U.S. Application Data

(60) Provisional application No. 62/088,336, filed on Dec. 5, 2014.

(51) Int. Cl.
*A61N 1/368* (2006.01)
*A61N 1/05* (2006.01)
(Continued)

(52) U.S. Cl.
CPC ............ *A61N 1/368* (2013.01); *A61N 1/059* (2013.01); *A61N 1/37205* (2013.01);
(Continued)

(58) Field of Classification Search
CPC ............... A61N 1/059; A61N 1/36542; A61N 1/37205; A61N 1/368; A61N 2001/0578;
(Continued)

(56) References Cited

U.S. PATENT DOCUMENTS 4,271,846 A * 6/1981 Little .................. A61N 1/0587
607/131
4,428,378 A * 1/1984 Anderson ............ A61B 5/1118
607/19
(Continued)

OTHER PUBLICATIONS

Spickler et al., "Totally Self-Contained Intracardiac Pacemaker", J. Electrocardiology, 3 (3-4), 1970, 325-331.

*Primary Examiner* — Mark W Bockelman
(74) *Attorney, Agent, or Firm* — Kilpatrick Townsend and Stockton, LLP

(57) ABSTRACT

Embodiments of the present invention generally relate to epicardial heart rhythm management. In some embodiments a method is provided for managing heart rhythm by implanting a pa device within the pericardial space of a patient. In some embodiments, an implantable device is provided for pacing the epicardial surface of a patient. The device may include a first module coupled to a second module by a tether. The first and second modules may be selectively placed for bi-ventricular pacing or for dual chamber pacing in some embodiments. Optionally the modules may be separate and may wirelessly communicate with one another and may also communicate with a heart stimulation device programmer. Optionally, a plurality of devices may be implanted in the pericardial space. A delivery device for delivering the implantable device to the pericardial space is also provided. Further embodiments provide implant retrieval devices and methods.

10 Claims, 24 Drawing Sheets

(51) Int. Cl.
  *A61N 1/372* (2006.01)
  *A61N 1/365* (2006.01)
  *A61B 17/34* (2006.01)
  *A61B 17/00* (2006.01)

(52) U.S. Cl.
  CPC ..... *A61B 17/3468* (2013.01); *A61B 2017/003* (2013.01); *A61B 2017/00358* (2013.01); *A61N 1/36542* (2013.01); *A61N 2001/0578* (2013.01)

(58) Field of Classification Search
  CPC .... A61B 2017/003; A61B 2017/00358; A61B 17/3468
  See application file for complete search history.

(56) References Cited

U.S. PATENT DOCUMENTS

| | | |
|---|---|---|
| 5,385,579 A | 1/1995 | Helland, Jr. et al. |
| 5,476,500 A | 12/1995 | Fain et al. |
| 5,871,532 A | 2/1999 | Schroeppel et al. |
| 6,256,541 B1 | 7/2001 | Heil et al. |
| 7,069,075 B2 | 6/2006 | Olson |
| 7,270,669 B1 | 9/2007 | Sra |
| 7,890,192 B1* | 2/2011 | Kelsch ............... A61B 17/8888 600/375 |
| 8,295,939 B2 | 10/2012 | Jacobson |
| 8,548,605 B2 | 10/2013 | Ollivier |
| 8,781,605 B2 | 7/2014 | Bornzin et al. |
| 2003/0074041 A1 | 4/2003 | Parry et al. |
| 2004/0127967 A1* | 7/2004 | Osypka ............... A61N 1/059 607/122 |
| 2004/0167416 A1 | 8/2004 | Lee |
| 2006/0085041 A1 | 4/2006 | Hastings et al. |
| 2006/0293740 A1 | 12/2006 | Heil, Jr. et al. |
| 2009/0082828 A1 | 3/2009 | Ostroff |
| 2011/0082466 A1 | 4/2011 | Ollivier |
| 2012/0232565 A1 | 9/2012 | Kveen et al. |

* cited by examiner

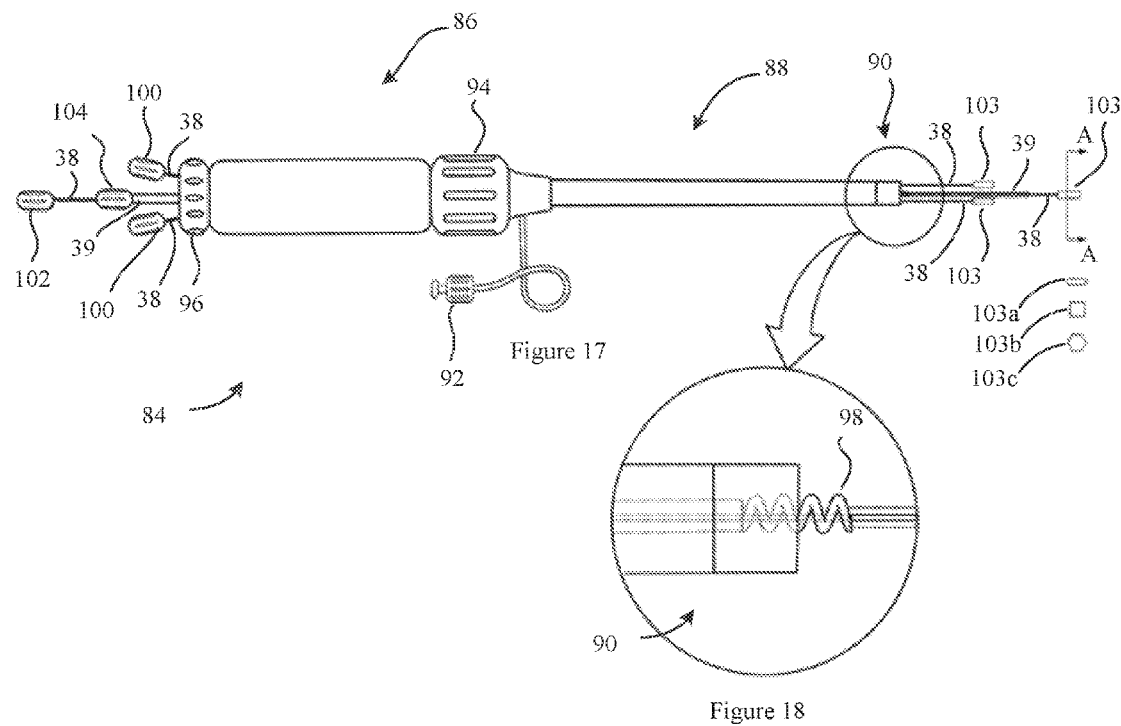
Figure 17
Figure 18
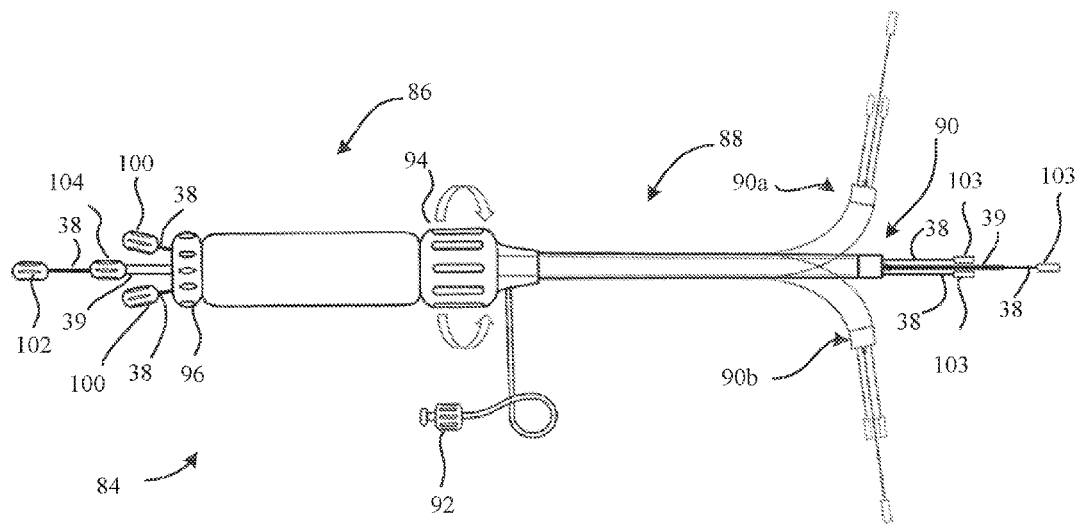
Figure 19

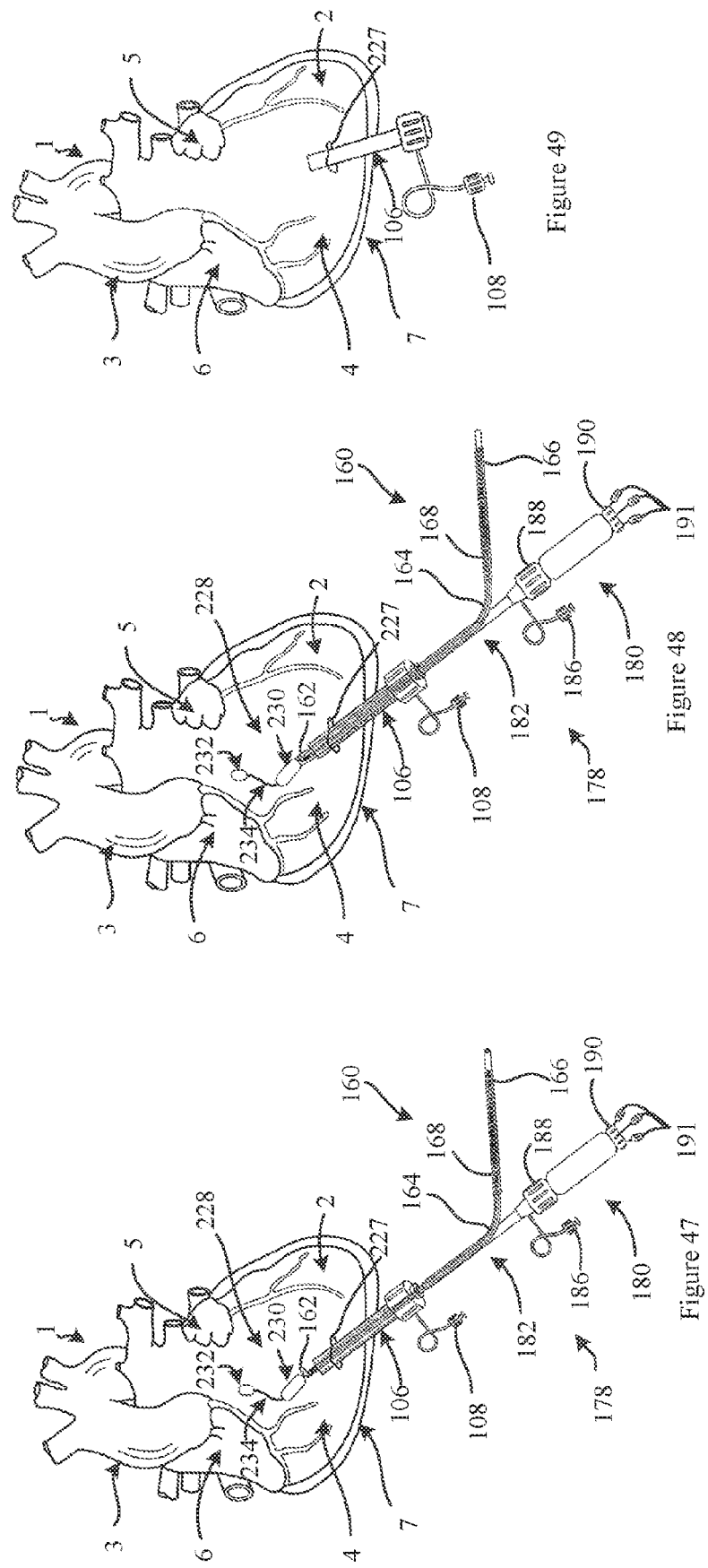

EPICARDIAL HEART RHYTHM MANAGEMENT DEVICES, SYSTEMS AND METHODS

CROSS REFERENCE TO RELATED APPLICATION DATA

The present application claims the benefit under 35 USC §119(e) of U.S. Provisional Application No. 62/088,336 filed Dec. 5, 2014; the full disclosure which is incorporated herein by reference in its entirety for all purposes.

BACKGROUND

The invention generally relates to improved medical devices, systems, and methods. In many embodiments, the invention provides devices, systems, and methods for heart rhythm management. In some specific embodiments, a heart stimulation device and/or system (e.g., including an epicardial pacemaker, implantable cardioverter-defibrillator (ICD), or the like) is provided for managing the heart rhythm of a patient. In these or other embodiments, delivery devices and kits can be provided for delivering implantable devices to an attachment location in the pericardial space of a patient. In further aspects, recapture devices are provided for detaching, repositioning and/or removing implants from a patient. Some cardiac rhythm devices, systems, and methods described herein include a heart-surface mounted stimulation device (including a stimulation signal generator) and an activity sensor that can be mounted away from the heart. Methods are also provided for delivering, implanting, repositioning, and/or retrieving implantable devices to or from an implantation site in the pericardial space of a patient. Still further aspects of the invention are described herein below.

An implantable cardioverter-defibrillator (ICD) is an implanted device that combines the functionality of a cardioverter and a defibrillator into a single implantable device. Specifically, the ICD may monitor the rate and rhythm of the heart and may deliver electrical shocks to the heart when the monitored heart rate exceeds a desired heart rate. Additionally, the ICD may deliver electrical energy to the heart to during cardiac dysrhythmias, ventricular fibrillation, and pulseless ventricular tachycardia to depolarize a mass of the heart muscle to terminate the dysrhythmia. Artificial implantable pacemakers are devices that are configured to maintain a desired heart rate of a patient with a naturally slower heart rate. Some artificial pacemakers may include the functionality of a defibrillator as well. Recently, left-ventricular cardiac pacing has been practiced to ameliorate heart failure; a practice termed cardiac resynchronization therapy (CRT). CRT has been practiced with electrode-leads and a pulse generator, either an implantable cardioverter-defibrillator (CRT-D) or an otherwise conventional pacemaker (CRT-P). The left-ventricular pacing conventionally uses an electrode in contact with cardiac muscle in that chamber. The corresponding electrode-lead is usually placed endocardially in a transvenous manner through the coronary sinus vein, or epicardially.

ICDs and pacemakers often include a housing (generally containing circuitry, a power source, and the like) implanted by in a small pocket created under the left collar bone. Leads typically extend from a connector between the lead and the housing, through a vein, along the blood flow path of the cardiovascular system into the heart, and to an electrode attached to heart tissues within one or more chambers of the heart. The implantation procedures may require not only transvenous delivery of the leads to the one or more heart chambers, but the leads may also extend through one or more valves of the heart, so that the valves open and close around the leads. The advancement and placement of the leads is often performed under fluoroscopic guidance to provide a physician a view of a stimulation position of the electrode lead. To facilitate fluoroscopic guidance, contrast agents may be introduced into the blood of the patient. Once implanted and attached, the pacemaker may pace the chambers and may also sense the heart's natural rhythm.

Recently, leadless pacemakers have been developed. These leadless pacemakers are self-contained intracardial pacemaker systems in which an electrode is rigidly affixed to the housing containing the signal generating circuitry and the like, so that the leadless pacemaker is implanted in a chamber of the heart and can operate without the use of flexible transvenous leads, obviating the need of creating a surgical pocket for implanting the pacemaker and thereby avoids visual lumps associated with subclavical implantation of pacemakers.

While the new leadless pacemakers represent advances in heart rhythm management for many patients, work in connection with the present invention suggests that further improvements may be available. For example, intracardiac pacemakers are often small enough to traverse veins of the patient and to fit within the chambers of the heart. Unfortunately, the reduced size may restrict battery capacity for the implanted device and may thus unduly limit pacemaker life. Further, given the delivery and implantation of standard pacemakers or the new leadless pacemakers at least partially within the blood flow of the patient, an associated risk of thrombus formation may remain, along with associated risks of clot debris traveling in the blood to the brain, heart, or lungs—thereby presenting at least some risk of stroke, myocardial infarctions, and/or pulmonary embolisms. Because of the risk associated with thrombus, it may not be safe to place the leads and leadless pacemaker in the left heart (e.g., left atrium and left ventricle) which presents serious limitations for efficacy treatment (e.g., bi-ventricular pacing or three-chamber pacing). In addition, both leads and leadless pacemakers are associated with perforation of the right atrium or right ventricular walls, which could occur during placement of the lead or leadless pacemaker over time. The risk of perforation is associated with serious clinical sequel or death. Moreover, it may be desirable to further simplify implantation methods, particularly when implantation involves test pacing of a candidate stimulation site, sensing thresholds, repositioning of the electrodes, etc., prior to identifying a preferred attachment location, ideally without having to re-anchor and remove the housing for each unsuccessful candidate location. Additionally, there may be some risk that intracardiac devices become dislodged during their lifetime given the constant motion of the heart, and it would be best if the resulting risks could be mitigated.

SUMMARY OF THE INVENTION

The present invention generally relates to improved medical devices, systems, and methods, with exemplary embodiments providing implantable heart stimulation devices (such as implantable pacemakers and/or ICDs) and heart stimulation device deployment and/or removal systems and methods. Embodiments of the heart stimulation devices described herein may include stimulation circuitry disposed along an epicardial or outer surface of the heart in the pericardial space of the patient, and may be electrically coupled to heart tissue without having to resort to a lead extending through a wall of a blood vessel into a chamber of the heart, and without having the challenges of implanting the circuitry (and/or an associated battery) within the heart chamber. Advantageously, the heart rhythm management systems described herein can be electrically coupled to a plurality of separated stimulation sites of the heart, with the stimulation being coordinated and/or included in a common circuit while still providing a long implant life.

The heart stimulation device may include one or more modules. For example, the heart stimulation device may include a first and a second module. The first and second module may be a proximal and a distal module. The first and second modules may be operatively coupled to one another. For example, in some embodiments, the first and second modules may be electrically coupled via a flexible conductive tether.

The one or more modules may each include an electrode positioned at a contact surface of each respective module for stimulating and/or pacing via the epicardial surface of the heart and sensing natural heart signals via the epicardial surface. The one or more modules may be used for dual-chamber and three-chamber stimulating and/or pacing, bi-ventricular stimulating and/or pacing, defibrillating, etc. A module may be provided to house a battery for powering a plurality of modules of the exemplary heart stimulation device. Optionally, a module may include a communication circuitry for synchronizing stimulating and/or pacing between a plurality of modules. In some specific embodiments, the module which includes a battery and/or communications circuitry may be larger than other modules. In some embodiments, the plurality of modules may have a similar size and may each house a separate battery. Communications between the modules may be performed via a flexible conductive tether or cable in some embodiments to reduce energy use over embodiments with wireless telemetry or the like. Within the one or more modules may be one or more anchor channels for deploying and retracting an anchor housed therein. The anchor may be helical anchor or a shape memory barb, for example. In some embodiments, the device may use include a polymer mesh for attaching to the epicardial wall with surgical adhesive to bond the mesh to the tissue.

Given the epicardial attachment of the device, methods of implantation are also provided. The method may start by accessing the pericardial space (e.g., subxiphoid surgical approach or other minimally invasive caudal approach) and an introducer sheath may be inserted therein. Thereafter the heart stimulation device may be inserted into the pericardial space with a delivery catheter. Once introduced, the catheter and/or a module may be steered for pacing and sensing to identify a good signal from the epicardial wall. Once a good signal is identified, anchors may be deployed to secure the one or more modules at preferred locations. For bi-ventricular stimulating and/or pacing, a first module may, for example, be placed over the left ventricle or the summit of the left vernicle to stimulate and/or pace the left ventricle and a second module may be placed on the right ventricle to stimulate and/or pace the right ventricle. For dual-chamber stimulating and/or pacing, the first module may, for example, be placed over the right atrium to stimulate and/or pace the right atrium and the second module may be placed on the right ventricle to stimulate and/or pace the right ventricle. For three-chamber stimulating and/or pacing, the first module may, for example, be placed over the right atrium to stimulate and/or pace the right atrium and the second module may be placed on the right ventricle to stimulate and/or pace the right ventricle and the third module may be placed on the summit of the left ventricle to simulate and/or pace the left ventricle. Once the modules are preferably placed, a screw control knob may be actuated to release the heart stimulation device from the delivery catheter.

While some embodiments comprise a first module coupled with a second module via a flexible tether, other embodiments may comprise one or more modules that may communicate wirelessly with one another and/or an external heart stimulation device programmer.

According to some embodiments of the invention, a method of implanting a heart stimulation device on the epicardial surface of a heart of a patient is provided. The method may include accessing the pericardial space of the patient through an incision in the pericardial wall of the patient and inserting the heart stimulation device into the pericardial space through the pericardial wall incision. Thereafter, the heart stimulation device may be swept over regions of the epicardial surface and heart signals may be sensed from regions of the epicardial surface as the heart stimulation device is swept. A desired attachment for the heart stimulation device may be identified based on the heart signals sensed from the epicardial surface and the heart stimulation device may be attached to epicardial surface at the desired attachment location. After attachment, the heart stimulation device may be activated to pace the epicardial surface of the heart at the desired attachment location. In some embodiments, the pericardial space of the patient is accessed by inserting an introducer sheath into the pericardial space through the incision. The heart stimulation device may be releasably coupled to a distal end of a delivery catheter and the heart stimulation device may be inserted into the pericardial space by inserting the heart stimulation device through the introducer sheath and into the pericardial space.

In some embodiments, the distal end of the delivery catheter is deflectable and the method sweeping the heart stimulation device over regions of the epicardial surface may include deflecting the distal end of the delivery catheter to sweep the heart stimulation device over the epicardial surface. In some embodiment, the heart stimulation device includes an injection channel with an opening on an attachment side of the heart stimulation device. The attachment side of the heart stimulation device may include a polymer mesh adjacent to the opening and attaching the heart stimulation device to the epicardial surface may include the step of injecting a surgical adhesive into the injection channel of the heart stimulation device so that the surgical adhesive exits the opening and bonds the polymer mesh to the epicardial surface of the heart. In some embodiments, the heart stimulation device includes an anchor channel with an opening on the attachment side of the heart stimulation device. The attachment of the heart stimulation device to the epicardial surface may include the step of advancing an anchor through the anchor channel and out of the opening to anchor the heart stimulation device to the epicardial surface of the heart.

In some embodiments, the anchor comprises a helical screw and is advanced out of the opening and engages the epicardial surface of the heart by rotating a stylet operatively coupled to the anchor. In further embodiments, the anchor may comprise a shape memory barb and the shape memory barb may be advanced out of the opening to engage the epicardial surface of the heart by pushing a stylet operatively coupled to the anchor distally. The shape memory barb may restricted to a collapsed configuration when within the anchor channel and may be expanded to a deployed configuration when advanced out of the opening of the anchor channel by the distal advancement of the stylet.

Optionally, the heart stimulation device may comprise a first module and a second module communicatively coupled to the first module. The step of identifying a desired attachment location may include identifying a desired first module attachment location by sweeping the first module over and sensing heart signals from regions of the epicardial surface and identifying a desired second module attachment location by sweeping the second module over and sensing heart signals from regions of the epicardial surface. Attaching the heart stimulation device may comprise attaching the first module to the epicardial surface at the desired first module attachment location and attaching the second module to the epicardial at the desired second module attachment location. In some embodiments, the first module is placed on the epicardial surface for stimulating and/or pacing the right atrium and the second module is placed on the epicardial surface for stimulating and/or pacing the right ventricle.

In further embodiments, the first module may be placed on the epicardial surface for stimulating and/or pacing the left ventricle and second module may be placed on the epicardial surface for stimulating and/or pacing the right ventricle. Optionally, the heart stimulation device may further include a third module communicatively coupled with the first and second modules. In such embodiments, identifying a desired attachment location for the heart stimulation device further includes identifying a desired third module attachment location by sweeping the third module over and sensing heart signals from regions of the epicardial surface. Attaching a heart stimulation device may include attaching the third module to the epicardial surface at the desired third module attachment location and the first module may be placed on the epicardial surface for stimulating and/or pacing the right atrium; the second module may be placed on the epicardial surface for stimulating and/or pacing the left ventricle; and the third module may be place on the epicardial surface for stimulating and/or pacing the right ventricle.

In some embodiments, the first and second may be wireless coupled together. In other embodiments, the first and second modules may be coupled by a tether and the first module may comprise a distal module and the second module may comprise a proximal module.

In some embodiments, the proximal module of the heart stimulation device is coupled to a distal end of the delivery catheter and sweeping the distal module over the epicardial surface may comprise deflecting the distal module relative to the proximate module and the distal end of the delivery catheter by actuating a distal module steering controller.

In further embodiments of the method, an activity level sensor may be attached to the patient. The activity level sensor may be communicatively coupled with the heart stimulation device to provide activity level data to the heart stimulation device. The heart stimulation device may adjust stimulating and/or pacing of the epicardial surface of the heart, based on activity level data received from the activity level sensor. In some embodiments, the activity level sensor is implanted within the patient by coupling the activity level sensor to a sternum, the rib, or parietal pleura of the patient. The activity level sensor may include an accelerometer and the activity level data may be accelerometer data.

In further aspects of the invention, an assembly for implanting a heart stimulation device along an epicardial surface of a heart of a patient is provided. The assembly may include a delivery catheter including a handle with a delivery catheter shaft extending distally from the handle to a distal end of the delivery catheter shaft. A heart stimulation device may be releaseably coupled with the delivery catheter at the distal end of the delivery catheter shaft. The delivery catheter shaft may be deflectable by a user actuating a deflection controller of the delivery catheter so as to deflect the distal end of the delivery catheter shaft. The distal end of the delivery catheter shaft may be deflected to sweep an electrode of the heart stimulation device between a plurality of locations.

In some embodiments, the heart stimulation device may include an anchor channel with an opening on an attachment side of the heart stimulation device. The heart stimulation device may also include an anchor advanceable through the anchor channel and out the opening to anchor the heart stimulation device on the epicardial surface of the heart. A stylet may extend through a lumen of the delivery catheter shaft and into the anchor channel of the heart stimulation device for operatively coupling a distal end of the stylet with the anchor when the heart stimulation device is releaseably coupled with the distal end of the delivery catheter shaft. The anchor may be a helical screw that may be advanced out of the opening to engage with the heart by rotating the stylet while the distal end of the stylet is operatively coupled with the anchor. Optionally, the anchor may be a shape-memory barb that may be advanced out of the opening to engage with the heart by pushing the stylet distally while the distal end of the stylet is operatively coupled with the anchor. The shape-memory barb may be restricted to a collapsed configuration when within the anchor channel and may be expanded to a deployed configuration when advanced out of the opening of the anchor channel by the distal advancement of the stylet.

In some embodiments, the heart stimulation device may include an injection channel with an opening on an attachment side of the heart stimulation device. The attachment side of the heart stimulation device may include a polymer mesh adjacent the opening. The delivery catheter may include an injection port fluidly coupled with the injection channel of the heart stimulation device when the heart stimulation device is releaseably coupled with the distal end of the delivery catheter shaft.

In some embodiments, the heart stimulation device may be coupled with the distal end of the delivery catheter shaft by an actuatable engagement feature of the delivery catheter. The delivery catheter may further include a heart stimulation device release controller for controllably actuating the engagement feature to release the heart stimulation device from the distal end of the delivery catheter shaft. The actuatable engagement feature of the deliver catheter may be a helical screw that engages with an engagement channel of the heart stimulation device. The heart stimulation device release controller may be actuated to rotate the helical screw so as to disengage with the engagement channel of the heart stimulation device.

Optionally, the heart stimulation device comprises a first module and a second module electrically coupled with the first module by a flexible tether. The first module may include a first electrode and the second module may include a second electrode. Optionally, only one of the first and second modules includes a battery for powering both modules.

The first module may be a proximal module and the second module may be a distal module. The proximal module may be releaseably coupled with the distal end of the delivery catheter shaft. The distal module may be separately steerable relative to the proximal module. A steering stylet may extend through the delivery catheter shaft, through the proximal module, and into the flexible tether. The steering stylet may be actuated at a proximal end of the steering stylet to controllably bend the flexible tether for steering the distal module relative to the proximal module.

In further aspects of the present invention, a method of implanting a heart stimulation device along an epicardial surface of a heart of a patient may be provided. The method may include accessing a pericardial space of the patient through a minimally invasive access path and inserting the heart stimulation device distally into the pericardial space through the access path. The heart stimulation device may include a first module having an electrode on an attachment side of the first module, a second module having an electrode on an attachment side of the second module, and a tether coupling the first module to the second module. The first module may be attached at a first location along the epicardial surface of the heart of the patient and the second module may be at a second location along the epicardial surface of the heart of the patient. The heart stimulation device may be activated to stimulate the heart.

The method may also include sweeping the electrode of the first module over the epicardial surface of the heart and sensing heart signals with the electrode of the first module from the epicardial surface of the heart to identify the first location; and sweeping the electrode of the second module over the epicardial surface of the heart and sensing heart signals with the electrode of the second module from the epicardial surface of the heart to identify the second location. The heart stimulation device may be releaseably coupled with a delivery catheter when inserted into the pericardial space and the electrode of the first module may be swept over the epicardial surface by controllably deflecting a shaft of the delivery catheter. Optionally, the electrode of the second module may be swept over the epicardial surface by controllably deflecting the tether coupling the first module to the second module.

The method may also include attaching an activity sensor to the patient and establishing a communication link between the activity sensor and the heart stimulation device. The stimulation of the heart by the heart stimulation device may be dependent on a signal received from the activity sensor through the established communication link that is indicative of a level of activity of the user.

In another embodiment of the present invention, an epicardial heart stimulation device is provided. The epicardial heart stimulation device may include a proximal epicardial heart stimulation device module comprising an electrode on an attachment side of the proximal epicardial heart stimulation device module. A distal epicardial heart stimulation device module may be provided that includes an electrode on an attachment side of the distal epicardial heart stimulation device module, and a tether may couple the proximal epicardial heart stimulation device module to the distal epicardial heart stimulation device module.

In some embodiments, the proximal epicardial heart stimulation device module includes a proximal end and a distal end and the length therebetween. The distal epicardial heart stimulation device module may similarly include a proximal and a distal end and a length therebetween, and the tether may couple the distal end of the proximal epicardial heart stimulation device to the proximal end of the distal epicardial heart stimulation device module. The attachment side of the proximal epicardial heart stimulation device module may be concave and couple with the epicardial surface of the heart and the direction transverse to the length of the proximal epicardial heart stimulation device module. The attachment side of the distal epicardial heart stimulation device module may also be concave and may couple with the epicardial surface of the heart and the direction transverse to the length of the distal epicardial heart stimulation device module.

In some embodiments, only one of the proximal epicardial heart stimulation device module and distal epicardial heart stimulation device module comprises a battery for powering both the proximal epicardial heart stimulation device module and the distal epicardial heart stimulation device module. The epicardial heart stimulation device module comprising the battery may be larger than the other epicardial heart stimulation device module. In some embodiments, the proximal epicardial heart stimulation device module comprises an attachment channel that extends from a proximal side of the proximal epicardial heart stimulation device module and terminates at an opening on the attachment side of the proximal epicardial heart stimulation device module. The distal epicardial heart stimulation device may include an attachment channel that extends through the proximal epicardial heart stimulation device module and through the tether and terminates at an opening on the attachment side of the distal epicardial heart stimulation device module.

The attachment channels of the proximal module and the distal module may comprise a helical anchor having a distal tissue penetrating end for advancement from the opening of the attachment channel and a proximal end couplable to a stylet in some embodiments of the invention. Optionally, a shape memory barb may be used, having a distal tissue penetrating end and a proximal end couplable to a stylet. The shape memory barb may be restricted to a collapsed configuration when within the attachment channel and expanded to a deployed configuration when advanced out of the opening of the attachment channel. In some embodiments, the attachment side of the proximal module and the attachment side of the distal module may include a polymer mesh.

In further aspects, yet another method of implanting a heart stimulation device is provided. The method may include attaching the heart stimulation device to a surface of a heart of a patient. The heart stimulation device may include a signal generator, and the signal generator may move with the surface of the heart. The method may further include attaching an activity sensor to the patient at a location separated from the heart (e.g., parietal pleura). A communication link may be established between the heart stimulation device and the activity sensor. The heart stimulation device may be activated with the signal generator to stimulate the heart and stimulation of the heart by the heart stimulation device may be dependent on a signal received from the activity sensor through the established communication link that is indicative of a level of activity of the user.

The heart stimulation device may be attached along an epicardial surface of the heart. Optionally, the heart stimulation device comprises a first module and a second module, each attached to the surface of the heart. The first module and the second module may be electrically coupled together by a flexible electrically conductive tether.

The heart stimulation device may increase a heart stimulation rate when the signal received from the activity sensor is indicative of an increased level of activity of the user. The heart stimulation device may decrease a heart stimulation rate when the signal received from the activity level sensor is indicative of a decreased level of activity of the user. The activity level sensor may be coupled to a sternum of the patient. The activity level sensor may include an accelerometer.

The heart stimulation device may be configured to identify stimulating and/or pacing parameters associated with the user activity indicated by the activity level sensor. The heart stimulation device may control stimulating and/or pacing pulse delivery as a function of the stimulating and/or pacing parameters.

The activity level sensor may include an attachment channel that extends from a proximal end of the activity level sensor to an opening on an attachment side of the activity level sensor. The activity level sensor may be attached by advancing an anchor from within the attachment channel to extend from the opening on the attachment side of the activity sensor. The anchor may be a helical anchor or a shape-memory barb.

The activity level sensor may include a polymer mesh on the attachment side of the activity level sensor adjacent to the opening of the attachment channel. The activity level sensor may be attached by advancing a surgical adhesive through the attachment channel so as to bond the polymer mesh of the activity level sensor to tissue of the patient.

The method may also include inserting the activity level sensor distally through a minimally invasive access path. The activity level sensor may be releaseably coupled to a distal end of a delivery catheter.

In further aspects, a heart stimulation system may be provided. The system may include a heart stimulation device for coupling with a surface of a heart of a patient. The heart stimulation device may include a signal generator for generating heart stimulation signals. The system may further include an activity level sensor for coupling to a location within the patient separate from the heart of the patient. The activity level sensor may be communicatively coupled with the heart stimulation device by a communication link. Stimulation of the heart by the heart stimulation device may be dependent on a signal received from the activity level sensor through the communication link that is indicative of a level of activity of the user.

The heart stimulation device may be an epicardial heart stimulation device for attaching along an epicardial surface of the heart and for stimulating the epicardial surface of the heart. The epicardial heart stimulation device may include a first epicardial module comprising an electrode on an attachment side of the first epicardial module and a second epicardial module comprising an electrode on an attachment side of the second epicardial module. A tether may couple the first epicardial module to the second epicardial module.

The activity level sensor may include an accelerometer. The heart stimulation device may be configured to identify stimulating and/or pacing parameters associated with the level of user activity indicated by the activity level sensor. The heart stimulation device may control stimulating and/or pacing pulse delivery as a function of the stimulating and/or pacing parameters. The activity level sensor may include an attachment channel that extends from a proximal end of the activity level sensor to an opening on an attachment side of the activity level sensor. The activity level sensor may include an anchor within the attachment channel that is configured to extend from the opening on the attachment side of the activity level sensor. The anchor may be a helical anchor or a shape-memory barb.

The activity level sensor may include a polymer mesh on the attachment side of the activity level sensor adjacent to the opening of the attachment channel. The activity level sensor may be configured to be attached by advancing a surgical adhesive through the attachment channel so as to bond the polymer mesh of the activity level sensor to tissue of the patient.

The heart stimulation device may increase a heart stimulation rate when the signal received from the activity sensor is indicative of an increased level of activity of the user. The heart stimulation device may decrease a heart stimulation rate when the signal received from the activity level sensor is indicative of a decreased level of activity of the user.

In further embodiments of the present invention, an epicardial heart stimulation system is provided. The epicardial heart stimulation system may include a delivery catheter comprising a handle coupled with the catheter shaft having a distal end. A heart stimulation device may be releasably coupled to the distal end of the catheter shaft by an engagement feature. The heart stimulation device may include a first anchor channel housing an anchor therein. The first anchor channel may terminate at an opening on an attachment side of the heart stimulation device. The delivery catheter may further include a heart stimulation device release controller for actuating the engagement feature of the delivery catheter to selectively disengage the heart stimulation device from the distal end of the catheter shaft. Additionally, the delivery catheter may also include a first anchor controller for actuating a first stylet to control the deployment of the heart stimulation device anchor disposed in the first anchor channel. The first stylet may extend down the catheter shaft and engage with the anchor housed in the first anchor channel of the heart stimulation device.

In some embodiments, the epicardial heart stimulation device system may also include a heart stimulation device that has a proximal module coupled to a distal module by a tether. The distal end of the catheter shaft may be releasably coupled with the proximal module at an attachment end of the proximal module and the distal module may extend cantilever from the distal end of the catheter shaft. Optionally, the first anchor channel may be disposed within the heart stimulation device module and may terminate on the attachment side of the proximal module. The distal module may comprise a second anchor channel housing an anchor therein. The second anchor channel may terminate at an opening on the attachment side of the distal module. The second anchor channel may extend through the tether and through the proximal module to the attachment end of the proximal module. The proximal module may include a first electrode on the attachment side of the proximal module and the distal module may include a second electrode on the attachment side of the distal module.

In some embodiments, the delivery catheter may further include a second anchor controller for actuating the second stylet to control the deployment of the heart stimulation device anchor disposed in the second anchor channel. The second stylet may extend down the catheter shaft and engage with the anchor housed in the second anchor channel of the heart stimulation device.

In some embodiments of the epicardial heart stimulation device system, the delivery catheter may further include a shaft deflection controller for deflecting the catheter shaft and a distal module steering controller for separately deflecting the distal module relative to the proximal module. Optionally, only one of the proximal module and the distal module includes a battery for powering both the proximal module and the distal module and the module having the battery may be larger than the other module.

In some embodiments, an epicardial heart stimulation device implantation kit is provided that includes a guide wire for insertion into the pericardial space of the patient and an introducer sheath for advancement over the guide wire and into the pericardial space, and may further include the epicardial heart stimulation device system described above for the delivery of the heart stimulation device to the pericardial space through the introducer sheath.

In further embodiments, an epicardial heart stimulation device implantation kit is provided. The epicardial heart stimulation device implantation kit may include the epicardial heart stimulation device systems described above and an activity level sensor for implantation within the patient. The activity level sensor may include an accelerometer and may be communicatively coupled with the heart stimulation device to provide accelerometer data to the heart stimulation device. The heart stimulation device may be configured to adjust stimulating and/or pacing of the epicardial surface of the heart based on accelerometer data received from the activity level data.

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

The invention will be better understood upon reading the following description and examining the figures which accompany it. These figures are provided by way of illustration only and are in no way limiting on the invention.

BRIEF DESCRIPTION OF THE DRAWINGS

Further details, aspects and embodiments of the invention will be described by way of example only and with reference to the drawings. In the drawings, like reference numbers are used to identify like or functionally similar elements. Elements in the figures are illustrated for simplicity and clarity and have not necessarily been drawn to scale.

FIG. 17 illustrates a delivery catheter for delivering heart stimulation devices to a target implantation site according to some embodiments of the present invention;

FIG. 18 illustrates a close up view of the distal end of the delivery catheter shown in FIG. 17 according to some embodiments of the present invention;

FIG. 19 illustrates the operation of the deflection knob of the delivery catheter shown in FIG. 17 to control the deflection of the distal end of the delivery catheter according to some embodiments of the invention;

FIG. 47 illustrates the use of a recapture catheter-snare assembly for retrieving an implanted device according to some embodiments of the invention;

FIG. 48 illustrates the engagement of the snare to the implanted device according to some embodiments of the invention;

FIG. 49 illustrates the removal of the implanted device through the introducer sheath using the recapture catheter according to some embodiments of the invention;

DETAILED DESCRIPTION

The subject matter of embodiments of the present invention is described here with specificity, but the claimed subject matter may be embodied in other ways, may include different elements or steps, and may be used in conjunction with other existing or future technologies.

Figure 1:
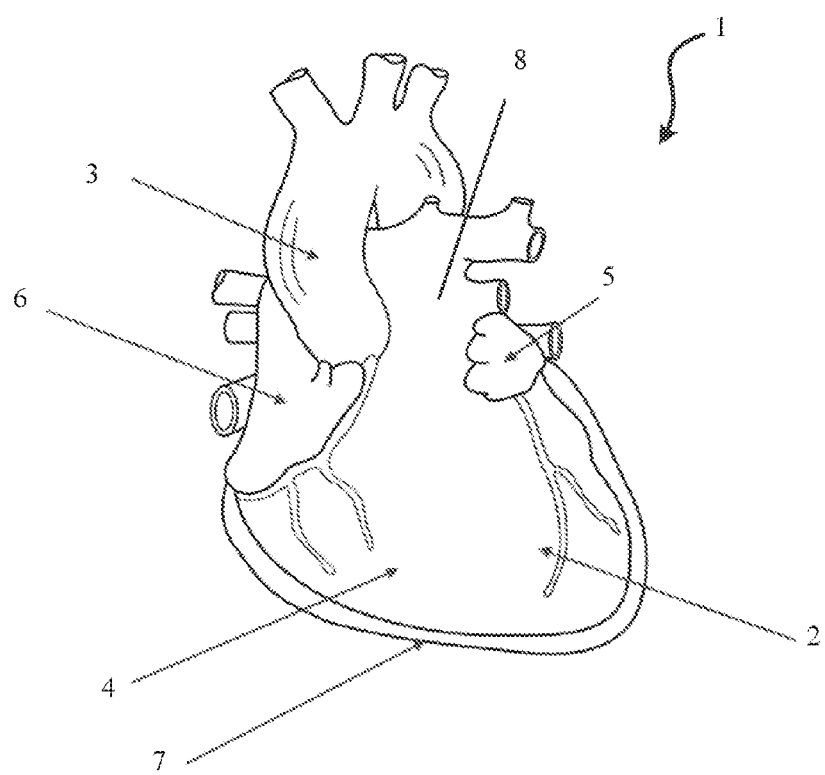
FIG. 1 illustrates the anatomy of a human heart.

FIG. 1 illustrates the anatomy of a human heart 1. Heart 1 includes a left ventricle 2 for pumping blood to the aorta 3. Heart 1 further includes a right ventricle 4 that pumps blood to the pulmonary artery. Ventricular fibrillation is a condition in which there is uncoordinated contraction of the ventricles 2, 4 of the heart 1. The ventricles 2, 4 may quiver and be unable to sufficiently pump blood through the patient's body. In such situations, an electric defibrillator may be used to reverse the condition by an electric discharge. In some situations, patients with high risk of ventricular fibrillation may benefit from an implantable cardioverter defibrillator ("ICD"). ICD devices may sense the natural heart rhythm of the patient and may correct detected irregular rhythms by delivering electrical impulses to the heart 1. Yet in another situation, the heart's natural pacemaker and/or conduction system fails to provide synchronized atrial and ventricular contractions at appropriate rates and intervals for a patient's needs. Cardiac pacing electrically stimulates the heart when the heart's nature pacemaker and/or conduction system fails to function properly. Such bradycardia pacing provides relief from symptoms and even life support for hundreds of thousands of patients. Cardiac pacing may also give electrical overdrive stimulation intended to suppress or convert tachyarrhythmias, again supplying relief from symptoms and preventing or terminating arrhythmias that could lead to sudden cardiac death.

Situated above the left ventricle 2 is a left atrial appendage 5. The left atrial appendage 5 is an extension of the left atrium and part of the left border of the heart's anterior surface. The left atrium 8 pumps blood from the lungs into the left ventricle 2. When a patient has atrial fibrillation, the electrical impulses that control the heartbeat do not travel in an orderly fashion through the heart. Instead, many impulses begin at the same time and spread through the atria. The fast and chaotic impulses may not give the atria time to contract and/or effectively squeeze blood into the left ventricle 2. A right atrial appendage 6 is pouch-like extension of the muscular part of the right atrium and is situated on top of the right atrium and above the right ventricle 4. The right atrium pumps blood to the right ventricle 4 during atrial systole/ventricular diastole.

The heart 1 is also surrounded by the pericardium 7 (also referred to herein as the pericardial wall). The pericardium 7 is a tissue layer that surrounds the heart 1. The pericardial space/cavity is the space or potential space between the pericardium 7 and the epicardial surface of the heart 1. The pericardial space includes serous fluid which helps protect the heart from external forces and also helps provide lubrication for the heart's continuous beating. Sub-xyphoid access to the pericardial space could be achieved by standard surgical techniques similar to pericardiocentesis, by inserting a guide needle through the chest and into the pericardial space. Then, a guidewire may be inserted through the needle and into the pericardial space. Next the needle is removed and the guidewire is used for introduction of subsequent devices.

Figure 2:
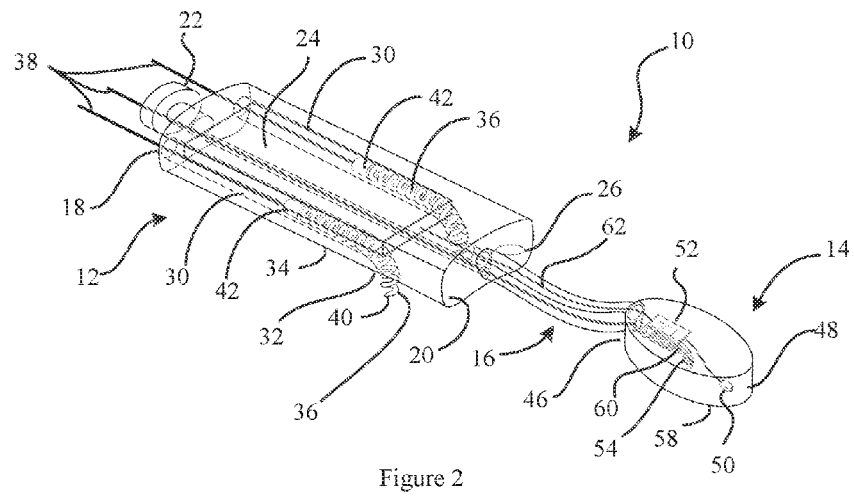
FIG. 2 illustrates an exemplary heart stimulation device according to some embodiments of the invention.
Figure 3:
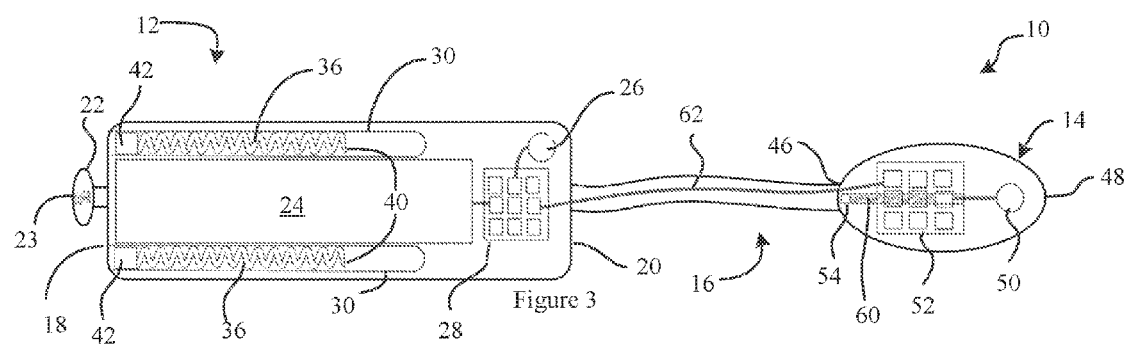
FIG. 3 illustrates a top view of the heart stimulation device shown in FIG. 2.
Figure 4:
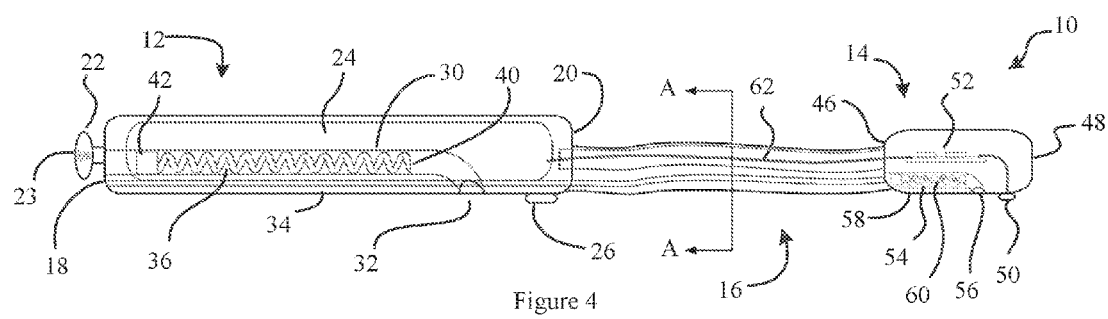
FIG. 4 illustrates a side view of the heart stimulation device shown in FIG. 2.

Many embodiments of the present invention generally related to devices for implantation into the pericardial space of the heart 1 and for attachment to an epicardial surface of the heart and methods related thereto, including delivery, attachment, release, recapture, repositioning, and/or removal. For example, some embodiments generally relate to implantable heart stimulation devices, such as, pacemakers, cardioverter-defibrillators, or the like. Embodiments of the heart stimulation devices described herein may be attached to an epicardial/outer wall of the heart in the pericardial space of the patient. FIG. 2 illustrates an exemplary implantable heart stimulation device 10 according to some embodiments of the invention. FIG. 3 illustrates a top view of the implantable heart stimulation device 10 shown in FIG. 2 and FIG. 4 illustrates a side view of the implantable heart stimulation device 10 of FIG. 2. As illustrated, in some embodiments, implantable heart stimulation device 10 may include a proximal module 12 coupled to a distal module 14 by a tether 16.

Proximal module 12 may have a proximal end 18, a distal end 20, and a length therebetween. A proximal button 22 portion of the proximal module 12 may extend proximally from the proximal end 18 of the proximal module 12. The proximal module 12 may further include at least one electrode 26 positioned on an attachment side 34 of the proximal module 12 for pacing, sensing and/or defibrillating purposes. The proximal module 12 may further include a battery 24, a pulse generator and communication board 28, and one or more attachment channels 30 disposed internally within the proximal module 12. The attachment channels 30 of the proximal module 12 may further include an anchor 36 disposed therein according to some embodiments of the invention. The proximal module 12 may have a generally rectangular cross-section with curved surface 34 to match the curvature of the heart at the site of attachment and rounded corners when viewed in the top view, FIG. 3, and may have relatively low profile, where the height of the proximal module 12 is less than the width and the length of the proximal module 12 as shown in the side view, FIG. 4. While the proximal module 12 is described and illustrated with one preferred configuration, it should be understood that the description and illustrations are exemplary only and non-limiting. The proximal module 12 may have other configurations as desired in other embodiments of the present invention. The proximal module may be manufactured from known bio-inert materials such as Titanium, PEEK or a combination of Titanium, PEEK, Silicone, and/or other implantable materials. The cross-section of the proximal module may be shaped like crescent to match the curvature of the heart at the site of attachment. The proximal module length may be from 20-80 mm, for example, preferably about 60 mm, and the height from 4-12 mm, for example, preferably about 8 mm, and the width from 6-20 mm, for example, preferably about 14 mm. The outer case of the proximal segment may be manufactured by know techniques such as CNC machining or metal injection molding (MIM) in two or more components and laser welded to provide hermetic seal for the inside components. The proximal case may be used as the second electrode in a bi-polar configuration. As used herein, the terms "proximal" and "distal" are to be taken as relative to the medical practitioner implanting the heart stimulation device (e.g., surgeon, cardiologist, or the like) or relative to the implant delivery device. "Proximal" is to be understood as relatively close to the practitioner/delivery device and "distal" is to be understood as relatively farther away from the practitioner/delivery device.

The proximal button 22 may be provided for engagement with a delivery catheter for device 10 delivery to an implantation site, the details of which are discussed further below. Further, the proximal button 22 may further facilitate device detachment and retrieval from an implantation site by acting as an engagement feature for engaging with a retrieval device, the details of which are discussed further below. In some embodiments, the proximal button 22 may include a channel 23 for coupling with an engagement feature of a delivery catheter and/or a recapture catheter. For example, channel 23 may be a threaded channel for engaging with a helical screw or coil of a delivery catheter and/or a recapture catheter. The exemplary proximal button 22 projects from the proximal end 18 of the proximal module 12 along a button axis. In some embodiments the proximal button 22 may have an outer dimension transverse to the button axis that increases at a proximal portion of the proximal button 22. The increase in the outer dimension may provide an enlarged protrusion that facilitates coupling a delivery catheter, a recapture catheter, retrieval snare, or the like to the proximal module 12 of the exemplary implantable heart stimulation device 10. In the illustrated embodiment 10, the exemplary proximal button 22 projects from the proximal end 18 of the proximal module 12 with a circular cross-section that enlarges in circumference to provide a lip for engagement with a delivery catheter, a recapture catheter, and/or a retrieval snare as will be discussed below. It should be understood that the proximal button 22 may have other configurations and that the configuration illustrated in the Figures is exemplary and non-limiting. Alternatively, the cross-section of the button may be rectangular, square; triangular, etc. In further alternatives, the button may be replaced by a hook, pigtail, or umbrella-like structure.

Electrode 26 may be placed on an attachment side 34 of the proximal module 12 for contacting an epicardial surface of the heart 1. The electrode 26 may deliver electrical pulses to the epicardial surface of the heart 1 to regulate the beating of the heart 1. Additionally, the electrode 26 may sense the electrical manifestation of naturally occurring heart beats. Electrode 26 may also provide defibrillating stimulation to the heart 1. While the illustrated embodiment 10 is shown with a single electrode 26 on the proximal module 12, it should be understood that other embodiments may include a plurality of electrodes 26. The electrode 26 may be manufactured from materials such as platinum or platinum and Iridium alloy with Titanium nitride or Iridium oxide coating. The tissue contact surface area of the electrode may be 1-4 mm$^2$, for example, preferably about 2 mm$^2$. The electrode 26 may contain a hollow structure open channel to the epicardial surface to house and elute appropriate amount of anti-inflammatory agent such as steroid to the pericardial tissue.

As illustrated, in some embodiments, the attachment side 34 of the proximal module 12 may be coupled to the epicardial surface of the heart 1 in a direction transverse to the length of the proximal module 12. Attachment side 34 of proximal module 12 may have a concave configuration. The concave configuration of attachment side 34 may better conform to portions of the epicardial surface of the heart 1 and may thereby provide better attachment of the proximal module 12 and the one or more electrodes 26 of the proximal module 12 to the epicardial surface of the heart 1. The attachment side 34 may also have some rounded or otherwise smooth transitions to the sides of proximal module 12. In some embodiments it may be preferable to use rounded edges to reduce the occurrence of unintentionally catching an edge of the implantable device 10 on a tissue surface or structure. The surface 34 may be partially, electrically insulated from the electrode 26 to function as the second electrode (e.g. sensing electrode), in the bi-polar configuration. The distance between exposed section (non-insulated) of the surface 34 and electrode 26 may be 8-20 mm, for example, preferably about 10 mm. The surface 34 may be electrically insulated using know techniques such vapor deposition (e.g. parylene coating).

Battery 24 may be coupled with the electrical components of the implantable heart stimulation device 10 for powering the devices. In many embodiments, the battery 24 may be a lithium battery or Li—CFx, which have been recently developed. Batteries using Li—CFx are unpressurized systems and are considered very stable compared to other lithium-based structures, the battery capacity may be 250-550 mah (mili-amp-hour) for example, preferably about 350 mah with 0.5-3 cc volume, for example, preferably about 1 cc.

Communication board 28 may be coupled with the battery 24 and the electrode 26. The communication board 28 may include a device processor or controller with logic stored therein. The controller may receive the sensed heart beats from the electrode 26 and may adjust the delivery of electrical impulses to the epicardial surface via the electrode 26 in response to the sensed heart beats. The communication board 28 may further coordinate communication between the proximal module 12 and the distal module 14 to provide dual chamber, or bi-ventricular, or three-chamber pacing and/or defibrillating. In some embodiments the communication board 28 may further provide for wireless communication between the implantable heart stimulation device 10 and an external device programmer. The board 28 may include a communication circuit and a pulse generator for controlling the delivery of the pulses to electrode 26. The board 28 may include a battery regulator, battery voltmeter, battery ammeter, a processor or controller, sense amplifier, communication amplifier, communication circuit and a pulse generator.

Attachment channel 30 may extend from an opening in the proximal end 18 of the proximal module 12 to an opening 32 on an attachment side 34 of the proximal module 12. In some embodiments, attachment channel 30 may be a lumen with an axis extending distally from the proximal side 18 of the proximal module 12 with a curve in the axis of the lumen to redirect the lumen to the attachment side 34 of the proximal module 12. Attachment channel 30 may be configured to guide an anchor 36 disposed therein to transition from a retracted and undeployed position from within the attachment channel 30 (where the anchor 36 is generally aligned along the length of the proximal module 12) to an advanced and deployed position (where the anchor 36 extends from the opening 32 on the attachment side 34 of the proximal module 12). In some embodiments the anchor 36 may extend from the opening 32 of the attachment channel 30 in a direction transverse to the length of the proximal module 12. In some embodiments, the attachment channel 30 may have internal surface features which engage with or otherwise cooperate with the anchor 36 disposed therein. For example, the inner surface of the attachment channel 30 may be threaded to couple with the threads or helical coils of an anchor 36 disposed therein. In the illustrated embodiment 10, two attachment channels 30 are provided in the proximal module 12 on both sides of the proximal module 12. While illustrated with two attachment channels 30, it should be understood that in some embodiments, the proximal module 12 may include a single attachment channel 30 utilizing a single anchor 36 or may include three or more attachment channels 30, each with associated anchors 36. In some embodiments the number of attachment channels 30 and anchors 36 used for the proximal module 12 may depend on a size of the proximal module 12. The diameter of the channel 30 may be 1-5 mm, for example, preferably about 2 mm. The length of channel 30 may be 5-40 mm, for example, preferably about 25 mm. The curvature of the channel 30 is intended to change the direction of the anchor so it could be positioned against the tissue at the attachment site. The radius of the curvature of channel 30 may be from 1-10 mm, for example, preferably about 5 mm. The angle of the curvature for channel 30 may be from 20-100 degrees, for example, preferably about 70 degrees.

Anchor 36 is illustrated as a helical coil having a distal tissue penetrating end 40. The proximal end 42 of the anchor 36 may include an engagement feature for coupling with a distal end of a stylet 38. The stylet 38 may releaseably couple with the anchor 36 and may be actuated to control the deployment and/or retraction of an anchor 36. For example in the illustrated embodiment, the stylet 38 may be rotated and/or pushed distally to deploy the anchor 36 from the anchor channel 30 and to engage with epicardial heart tissue. Further details on anchor deployment will be discussed below. The anchor 36 may be configured as helix (screw) to engage the tissue by rotating in one direction, and to disengage from the tissue by rotating in the opposite direction. The helical anchor may be manufactured with known materials such as Platinum, Platinum-Iridium alloy, Stainless steel, Elgiloy, or super elastic material such as Nitinol. The dimensions of the helical anchor may be from 2-5 mm in OD, for example, preferably about 2 mm. The helical anchor may comprise wire with 0.008-0.020 inch in diameter, for example, preferably about 0.011 inch in diameter or the helical anchor may be made by other known manufacturing techniques such as laser cutting a hypo tube. The helical anchor may comprise a configuration with constant pitch or variable pitch. The pitch of the helical anchor may be between 0.5-3 mm, for example, preferably about 0.9 mm. The anchor may also comprise other configurations such as expandable hooks made from a super elastic material such as Nitinol. The anchor may include 1-10 hooks, for example, preferably about 4 hooks. The diameter of the hooks may be from 1-10 mm, for example, preferably about 5 mm. The arc length of the hooks may be from 3-30 mm, for example, preferably about 15 mm. The multi-hook anchor may be made by known manufacturing techniques such as laser cutting a tube or sheet of super elastic material in one piece or multiple pieces and then laser welded together.

The distal module 14 may have a proximal end 46, a distal end 48 with a length therebetween. The distal module 14 may include an electrode 50 positioned on an attachment side 58 of distal module 14 for pacing and sensing purposes. The distal module 14 may further include a pulse generator 52, and one or more attachment channels 54 disposed internally within the distal module 14. The attachment channel 54 of the distal module 14 may further include an anchor 60 disposed therein according to some embodiments of the invention. The distal module 14 may have an elongate and/or roughly elliptical cross-section when viewed from the top, FIG. 3, and may have a relatively low profile where the height of the distal module 14 is less than the width and the length of the distal module 14 as shown in the side view, FIG. 4. Distal and/or proximal modules having elongate cross-sections may help maintain an orientation of any electrodes and anchor systems during lateral movement in the pericardial space. Further, as illustrated in FIG. 4, the distal module 14 may include rounded edges where the top surface transitions to the sides of the distal module 14 and where the sides of the distal module 14 transition to the attachment side 58 of the distal module 14. The distal module 14 may have other configurations as desired in other embodiments of the present invention. The distal module 14 may be made from known material such as Titanium using manufacturing techniques such as CNC machining or metal injection molding (MIM) to form two shells and laser welded together to form a hermetic seal. The height of the distal module 14 may be from 3-10 mm, for example, preferably about 6 mm, and a width between 6-20 mm, for example, preferably about 10 mm, and the length of the distal module 14 may be from 10-40 mm, for example, preferably about 20 mm. The distal module 14 may be configured to a variety of shapes such as a curved circular disk, or curved elliptical disk with rounded edges to prevent erosion and damage to the surrounding tissue. The curvature of the disk may be configured to match the curvature of the cardiac tissue at the site of attachment. The radius of curvature of the distal segment 14 may be from 15-40 mm, for example, preferably about 25 mm.

Electrode 50 may have a similar configuration as electrode 26, described above. For example, electrode 50 may be configured to deliver electrical pulses to stimulate and/or pace the epicardial surface of the heart 1 of a patient. Further the electrode 50 may be configured to sense electrical signals associated with the patient's natural heartbeat. Similar to proximal module 12, while the illustrated embodiment 10 is shown with a single electrode 50 on the distal module 14, it should be understood that other embodiments may include a plurality of electrodes 50 on the distal module 14. The electrode 50 may be made from materials such as Platinum or Platinum-Iridium alloy and coated with Titanium Nitride or Iridium Oxide. The electrode 50 may have a tissue contact surface area from 1-4 mm$^2$, for example, preferably about 2 mm$^2$.

In some embodiments, the attachment side 58 of the distal module 14 may couple to the epicardial surface of the heart 1 in a direction transverse to the length of the distal module 14. Attachment side 58 of distal module 14 may also have a concave configuration. The concave configuration of attachment side 58 may better conform to portions of the epicardial surface of the heart 1 and may thereby provide better attachment of the distal module 14 and the one or more electrodes 50 of the distal module 14 to the epicardial surface of the heart 1. The attachment side 58 may also have some rounded or otherwise smooth transitions to the sides of distal module 14. The attachment site 58 may be fully or partially insulated using known coating technique such as vapor deposition and materials such as paryrlene. In the partially coated configuration, the non-coated section of the surface 58 may serve as the second electrode, or sensing electrode in (bi-polar) pacing and sensing.

Distal module 14 may include a separate pulse generator board 52 for controlling the delivery of electrical pulses to electrode 50. Pulse generator 52 may be coupled with communication board 28 and communication board 28 may coordinate the delivery of electrical pulses to electrode 26 and electrode 50 depending on the programming of the implantable heart stimulation device 10. In some embodiments, the communication board 28 may provide for bi-ventricular stimulating and/or pacing or dual chamber stimulating and/or pacing. In some embodiments electrical pulses may be delivered to electrodes 26, 50 simultaneously. In other embodiments, electrical pulses may be delivered asynchronously to electrodes 26, 50. The board 52 may include a battery regulator, battery voltmeter, battery ammeter, a processor or controller, sense amplifier, communication amplifier, communication circuit and a pulse generator.

Attachment channel 54 may extend from an opening in the proximal end 18 of the proximal module 12, through the proximal module 12, through the tether 16, and to an opening 56 on the attachment side 58 of the distal module 14. In some embodiments, attachment channel 54 may be a lumen with an axis extending distally from the proximal side 18 of the proximal module 12 with a curve in the axis of the lumen to redirect the lumen to the attachment side 58 of the distal module 14. Attachment channel 54 may be configured to guide an anchor 60 disposed therein to transition from a retracted and stored position from within the attachment channel 54 where the anchor 60 is generally aligned along the length of the distal module 14 (e.g., FIG. 4) to an advanced and deployed position where the anchor 60 extends from the opening 56 on the attachment side 58 of the distal module 14. In some embodiments the anchor 60 may extend from the opening 56 of the attachment channel 54 in a direction transverse to the length of the distal module 14. In some embodiments, the attachment channel 54 may have internal surface features which engage with or otherwise cooperate with the anchor 60 disposed therein. For example, the inner surface of the attachment channel 54 may be threaded to couple with the threads or helical coils of an anchor 60 disposed therein. In the illustrated embodiment 10, a single attachment channel 54 is provided with the opening 56 centered along the width of the distal module 14. While illustrated with a single attachment channel 54, it should be understood that in some embodiments, the distal module 14 may include a plurality of attachment channels 54, each with associated anchors 60. In some embodiments the number of attachment channels 54 and anchors 60 used for the distal module 14 may depend on a size of the distal module 14. In some embodiments, the attachment channel 54 may have a smaller lumen diameter compared to a lumen diameter of attachment channel 30. The diameter of the attachment channel 54 may be 1-5 mm, for example, preferably about 2 mm. The length of channel 30 may be 5-40 mm, for example, preferably about 15 mm. The curvature of the channel 54 may be configured to change the direction of the anchor so it could be positioned against the tissue at the attachment site. The radius of the curvature of channel 54 may be from 1-10 mm, for example, preferably about 5 mm.

The angle of the curvature for channel 54 may be from 20-100 degrees, for example, preferably about 70 degrees.

Anchor 60 may have a similar configuration as anchor 36. For example, anchor 60 may be a helical coil having a distal tissue penetrating end and a proximal end of the anchor 60 may include an engagement feature for coupling with a distal end of a stylet 38. The stylet 38 may releaseably couple with the anchor 60 and may be actuated to control the deployment and/retraction of an anchor 60. For example, in the illustrated embodiment, the central stylet 38 may be rotated and/or pushed distally to deploy the anchor 60 from the anchor channel 54 and to engage with epicardial heart tissue. In some embodiments, the anchor 60 may be a smaller helical coil compared to anchors 36. For example, anchor 60 may have a length shorter than a length of anchors 36. Optionally, anchor 60 may comprise a helical coil with a smaller helical diameter than the helical diameter of anchor 36. Further, anchor 60 may comprise a wire with a smaller diameter than a wire used for anchor 36. Further details on anchor deployment will be discussed below. The anchor 60 may be configured as helix (screw) to engage the tissue by rotating in one direction, and to disengage from the tissue by rotating in the opposite direction. The helical anchor may be made from known materials such as Platinum, Platinum-Iridium alloy, Stainless steel, Elgiloy, super elastic materials such as Nitinol, or other materials. The dimensions of the helical anchor may be from 2-5 mm in outside diameter (OD), for example, preferably about 2 mm. The helical anchor may be made from wire with 0.008-0.020 inch in diameter, for example, preferably about 0.011 inch in diameter. The helical anchor may be made by other know manufacturing techniques such as laser cutting a hypo tube or the like. The helical anchor may be made to a configuration with constant pitch or variable pitch. The pitch of the helical anchor may be between 0.5-3 mm, for example, preferably about 0.9 mm. The anchor may also be made to other configurations such as expandable hooks made from a super elastic material such as Nitinol. The anchor may include 1-10 hooks, for example, preferably about 4 hooks. The diameter of the hooks may be from 1-10 mm, for example, preferably about 5 mm. The arc length of the hooks may be from 3-30 mm for example, preferably about 15 mm. The multi-hook anchor may be made by know manufacturing techniques such as laser cutting a tube or sheet of super elastic material in one piece or multiple pieces and then laser welded together.

Figure 5:
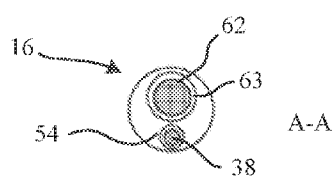
FIG. 5 illustrates a cross-sectional view of the tether along A-A of FIG. 4 according to some embodiments of the present invention.

Tether 16 may couple the proximal module 12 with the distal module 14. In some embodiments, tether 16 may couple the distal end 20 of the proximal module 12 with the proximal end 46 of the distal module 14. Tether 16 may include a conductive wire 62 that couples the electronics of the proximal module 12 and with the electronics of the distal module 14. As mentioned above, tether 16 may further include a lumen that is a portion of the attachment channel 54 extending through the length of the tether 16 and into the distal module 14. FIG. 5 illustrates a cross-sectional view of the tether 16 along A-A of FIG. 4 according to some embodiments of the present invention. As illustrated in FIG. 5, tether 16 may include a conductive wire lumen 63 with the conductive wire 62 disposed therein. Also, the tether 16 may include attachment channel 54. When deploying or retrieving device 10, a stylet 38 may be positioned within attachment channel 54 for engaging with the anchor 60 of the distal module 14. Accordingly, in some embodiments, the tether may be a flexible multi-lumen tube. In some embodiments, the tether 16 may be manufactured from polyurethane, silicon, or the like. The tether 16 may be constructed using known manufacturing techniques, such as by extruding a multi-lumen polymeric tubing and reinforcing by a coil or braid made of known materials such as Cobalt Chromium Nickel, or Cobalt Chromium Molybdenum. The support coil or braid structure may be manufactured from strands of above mentioned metals with circular or rectangular cross-sections (wire or ribbon) with a dimension from 0.002-0.010 in, for example, preferably about 0.006 inch in the circular configuration, and 0.001-0.005 inch in thickness and 0.002-0.010 inch in width, for example, preferably about 0.001×0.003 inch, in the ribbon configuration. One or more lumens of the multi-lumen tube may be lined with lubricious material such as PTFE to allow easier introduction of the stylets through the lumens. The tether 16 may be extruded from material such as Polyurethane with a durameter between 30D-90D, for example, preferably about 40D. The tether may be constructed from an ePTFE or a combination of polyurethane multi-lumen extrusion as the inside core and ePTFE jacket to prevent adhesion and tissue ingrowth and ongrowth on the tether to facilitated easier retrieval after months to years after implantation. All or segments of the tether might be configured to an accordion shaped tube to improve durability under cyclical loads.

The conductive wire 62 may couple the communications board 28 of the proximal module 12 with the pulse generator 52 of the distal module 14. Further, the conductive wire 62 may couple the battery 24 of the proximal module 12 with the pulse generator 52 of the distal module 14. The conductive wire 62 may be constructed with strands of know materials such as Cobalt Chromium Nickel, or Cobalt Chromium Molybdenum and silver core to form a conductive cable. The conductive cable may be insulated with thin layer of PTFE or other suitable materials. A diameter of the conductive wire may be between 0.003 in to 0.012 in, for example, preferably about 0.008 in. The conductive wire may be configured to a hollow cable configuration to allow passage of stylet through the center lumen. Accordingly, in some embodiments, a battery 24 may be provided in only one of the two modules but may be configured to power both modules. Optionally, the module with the battery 24 may be larger than the module without a battery 24 to accommodate a battery 24 with a greater power capacity. While the illustrated heart stimulation device 10 is shown with a battery 24 only in the proximal module 12, it should be understood that in some embodiments, a battery 24 may be provided only in the distal module 14. Further, optionally, both the proximal module 12 and the distal module 14 include batteries 24.

FIG. 3 and FIG. 4 illustrate the top and side view, respectively, of the exemplary heart stimulation device 10 when the anchors 36, 60 are retracted within anchor channels 30, 54, respectively, according to some embodiments of the invention. Implantable heart stimulation device 10 may be in a delivery configuration when the anchors 36, 60 are retracted within anchor channels 30, 54, respectively. When retracted, the anchors 36, 60 may have an anchor axis that is parallel to the length of the proximal module 12 and the distal module 14, respectively. Further, in some embodiments, the proximal end 42 of anchors 36 may be adjacent to the proximal end 18 of the proximal module 12.

Figure 6:
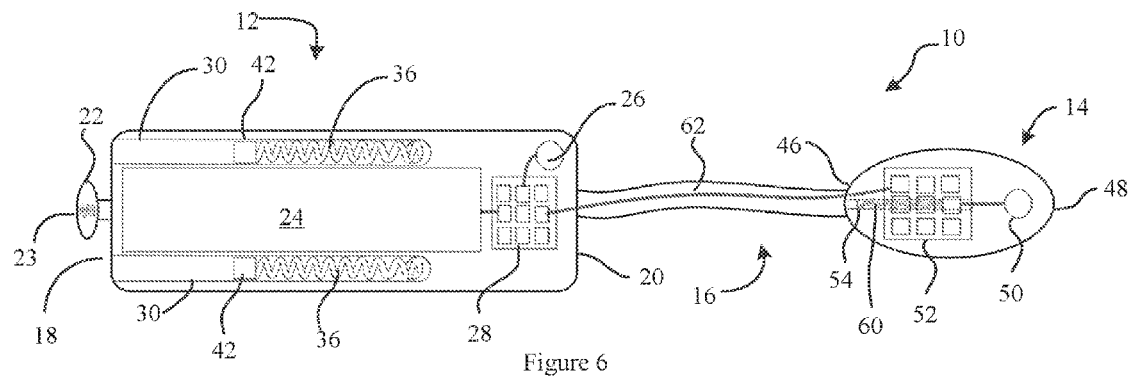
FIG. 6 illustrates a top view of the exemplary heart stimulation device shown in FIG. 2 with the anchors advanced in a deployed position according to some embodiments of the invention.
Figure 7:
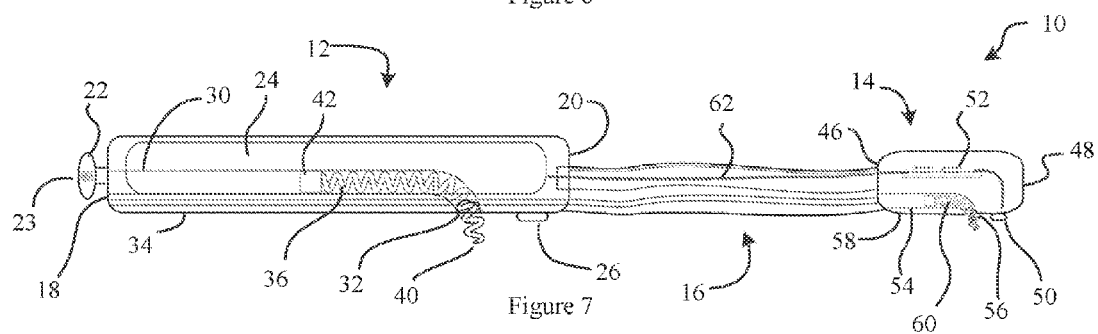
FIG. 7 illustrates a side view of the exemplary heart stimulation device shown in FIG. 2 with the anchors advanced in a deployed position according to some embodiments of the invention.

FIG. 6 and FIG. 7 illustrate a top view and a side view, respectively, of the exemplary heart stimulation device 10 when the anchors 36, 60 are advanced out of anchor channels 30, 54, respectively, according to some embodiments of the invention. Implantable heart stimulation device 10 may be in a deployed configuration when the anchors 36, 60 are advanced out of anchor channels 30, 54, respectively. When in the deployed configuration, anchors 36, 60 may have an anchor axis that angles towards the attachment side 34, 58 of the proximal module 12 and distal module 14, respectively.

Figure 8:
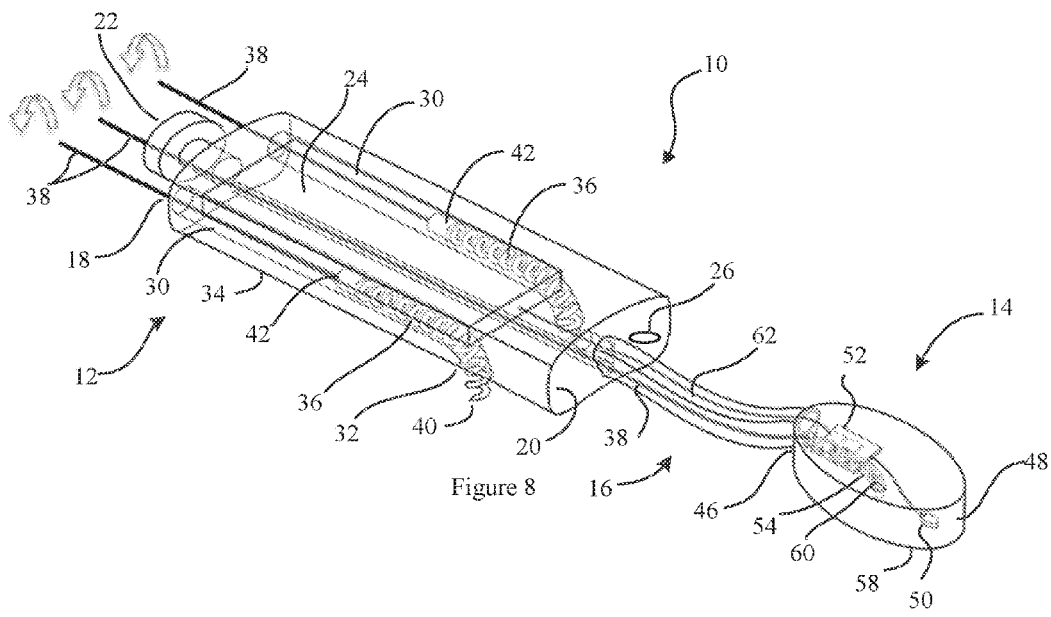
FIG. 8 illustrates the operation of stylets for deploying the anchors of the exemplary heart stimulation device shown in FIG. 2 according to some embodiments of the invention.

FIG. 8 illustrates the operation of stylets 38 for deploying the anchors 36, 60 of the exemplary implantable heart stimulation device 10 according to some embodiments of the invention. As illustrated in FIG. 8, stylets 38 may be advanced into the attachment channels 30, 54 for deploying the anchors 36, 60. A distal end of the stylets 38 may be configured to engage with a proximal end 42 of the anchors 36 and a proximal end of anchor 60 for actuating anchors 36, 60. In some embodiments, the stylets 38 may rotationally couple with the anchors 36, 60. In the illustrated embodiment 10, the stylets 38 may be advanced distally to advance anchors 36, 60 distally in attachment channels 30, 54, respectively. Additionally, the stylets 38 may be rotated to rotate the anchors 36, 60 so that when the distal end 40 of the anchors 36 and the distal end of the anchor 60 extend from the openings 32, 56, respectively, and the anchors 36, 60 engage with the epicardial surface of the heart 1 and screw into the tissue to secure the implantable heart stimulation device 10 to the surface of the heart 1. While the heart stimulation device 10 illustrated in FIGS. 2-8 uses helical coil anchors 36, 60 that rotatably engage with tissue of the heart 1 to secure the heart stimulation device 10 to the implantation location, it should be understood that this anchor configuration is exemplary and non-limiting.

Figure 9:
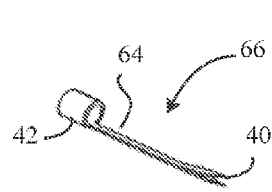
FIG. 9 shows an exemplary shape-memory barb in a collapsed configuration according to some embodiments of the present invention.
Figure 10:
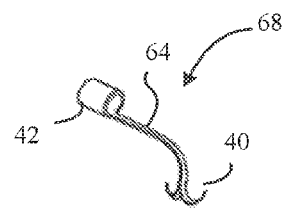
FIG. 10 shows the exemplary shape-memory barb shown in FIG. 9 in a deployed configuration according to some embodiments of the present invention.

For example, FIG. 9 shows an exemplary shape-memory barb 64 in an exemplary collapsed configuration 66 that may be used to secure the implantable heart stimulation device 10 to the epicardial surface of the heart 1 according to some embodiments of the present invention. FIG. 10 shows the exemplary shape-memory barb 64 shown in FIG. 9 in a deployed configuration 68 according to some embodiments of the present invention. As illustrated in FIG. 9, barb 64 may include a plurality of barb portions, each with tissue penetrating distal ends 40. The barb 64 may be manufactured from shape-memory material such as nitinol. The barb portions of barb 64 may be manufactured separately and then coupled together (e.g., through welding or the like) to form barb 64. When in the collapsed configuration 66, the barb portions may be restrained so that the distal tissue penetrating ends are generally aligned in a distal direction. As illustrated in FIG. 10, when in the deployed configuration 68, the barb portions of the barb 64 may deflect transverse to the distal direction and the tissue penetrating distal ends 40 of each barb portion may curl in opposite directions from one another. In the illustrated embodiment of the barb 64, one tissue penetrating distal end 40 may curl in the distal direction whereas the other tissue penetrating distal end 40 may curl in a proximal direction. While illustrated with two barb portions and two distal tissue penetrating ends 40, it should be understood that other shape-memory barb configurations are possible. For example, in some embodiments, a single barb portion and a single tissue penetrating end 40 may be sufficient for securing a heart stimulation device 10 to the epicardial surface of the heart 1. In some embodiments, three or more barb portions and distal tissue penetrating ends 40 may be deployed to secure the device 10 to the epicardial surface of the heart 1. The barb 64 may also be made to a configurations such as expandable hooks made from a super elastic material such as Nitinol. The anchor may include 1-10 hooks, for example, preferably about 4 hooks. The diameter of the curvature of the hooks may be from 1-10 mm, for example, preferably about 5 mm. The arc length of the hooks may be from 3-30 mm, for example, preferably about 15 mm. The expanded dimension of the hooks (tip to tip) may be from 5-15 mm, for example, preferably about 10 mm. The multi-hook anchor may be manufactured by known manufacturing techniques such as laser cutting a tube or sheet of super elastic material in one piece or multiple pieces and then laser welded together.

Figure 11:
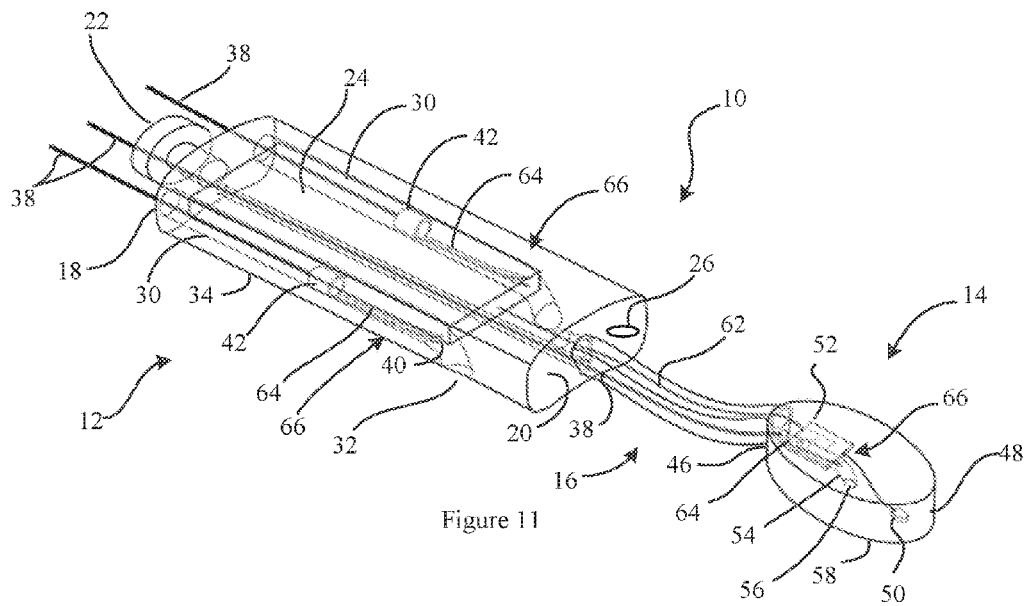
FIG. 11 illustrates an exemplary heart stimulation device using the shape-memory barb shown in FIG. 9 and FIG. 10 with the shape-memory barb in a retracted and collapsed configuration according to some embodiments of the present invention.
Figure 12:
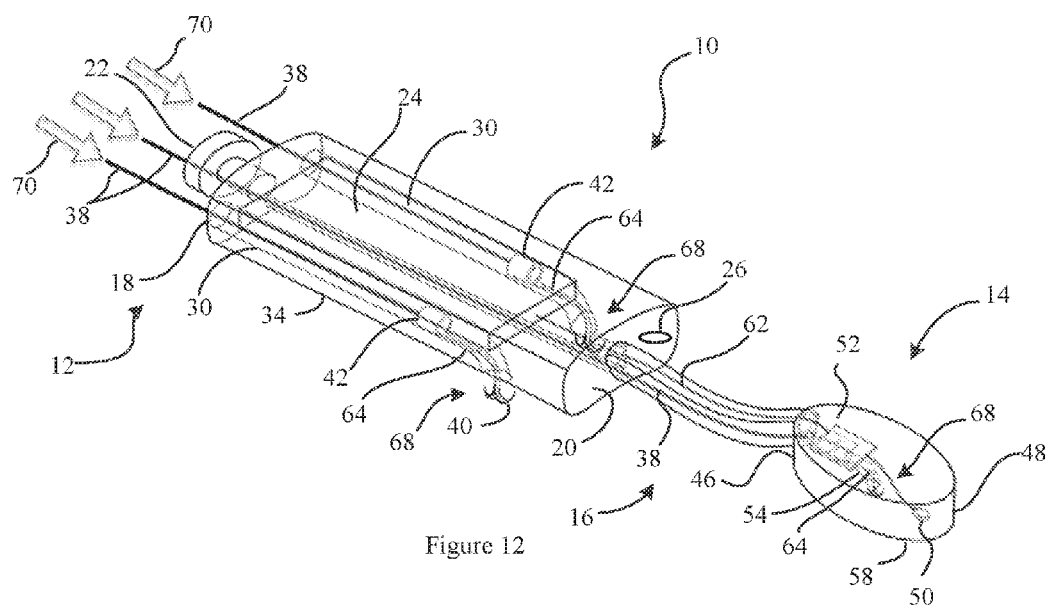
FIG. 12 illustrates the exemplary heart stimulation device of FIG. 11 with the shape-memory barb in an advanced and deployed configuration according to some embodiments of the present invention.

FIG. 11 illustrates exemplary implantable heart stimulation device 10 using the shape-memory barb 64 shown in FIG. 9 and FIG. 10 with the shape-memory barb 64 in a retracted and collapsed configuration 66 according to some embodiments of the present invention. When the shape-memory barb 64 is in the retracted and collapsed configuration 66, the implantable heart stimulation device 10 may be in a delivery configuration according to some embodiments of the invention. As illustrated, in FIG. 11 when the shape-memory barb 64 is disposed within the attachment channels 30, 54, the barb portions may be restricted by the attachment channels 30, 54 to the collapsed configuration 66. FIG. 12 illustrates the exemplary implantable heart stimulation device 10 of FIG. 11 with the shape-memory barb 64 in an advanced and deployed configuration 68 according to some embodiments of the present invention. To deploy barbs 64 from the attachment channels 30, 54, respectively, a stylet 38 may be advanced into attachment channels 30, 54 to engage with a proximal end 42 of the barb 64. The stylets 38 may releaseably couple with the proximal end 42 of the barb 64. Stylets 38 may then be advanced distally to urge the barbs 64 distally toward the openings 32, 56 of attachment channels 30, 54. As the distal tissue penetrating ends 40 of the barb 64 are advanced toward openings 32, 56 of attachment channels 30, 54, respectively, the distal tissue penetrating ends 40 are urged transverse to the distal direction and may be advanced into the epicardial surface of the heart 1. As the barb 64 is advanced further distally by the actuation of the stylets 38, the distal ends 40 of the barb 64 may curl back towards the implanted device 10. In some embodiments, the distal tip 40 of one barb portion may curl in a direction opposite of the curl of the distal tip 40 of the other barb portion. For example, in the illustrated embodiment 10 of FIG. 12, one distal tip 40 may curl back towards the device 10 in the distal direction while the other distal tip 40 may curl back towards the device 10 in the proximal direction. While the embodiments described above may utilize anchors (e.g., anchors 36, 60, 64 or the like) for securing the heart stimulation device 10 to the epicardial surface of the heart 1, other embodiments may use other attachment methods and devices for securing the heart stimulation device 10 to the epicardial surface.

Figure 13:
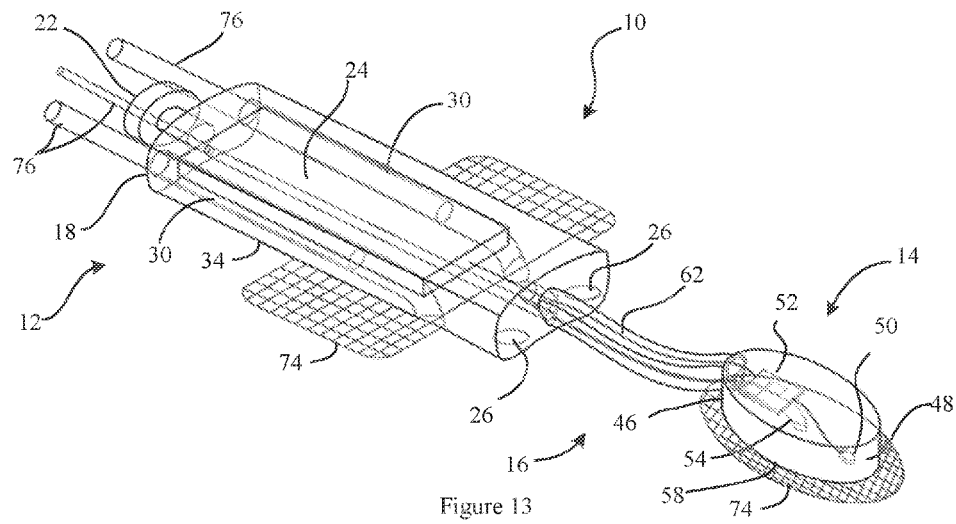
FIG. 13 illustrates an exemplary heart stimulation device using a polymer mesh for attachment to the epicardial surface according to some embodiments of the present invention.

For example FIG. 13 illustrates an exemplary implantable heart stimulation device 10 further including a polymer mesh 74 for facilitating attachment of the heart stimulation device 10 to the epicardial surface according to some embodiments of the present invention. As shown in FIG. 13 the proximal module 12 may further include polymer mesh 74 on the attachment side 34 of the proximal module 12. The polymer mesh 74 of the proximal module 12 may be disposed adjacent openings 32 of the attachment channels 30. Additionally, the distal module 14 may also include polymer mesh 74 on the attachment side 58 of the distal module 14. The polymer mesh 74 of the distal module 14 may be disposed adjacent opening 56 of attachment channel 54. The polymer mesh 74 may be Dakron, polyester, PTFE felt, or the like. Injection ports 76 may extend from a proximal end 18 of the proximal module 12. The injection ports 76 may be releaseably coupled with the attachment channels 30, 54.

Figure 14:
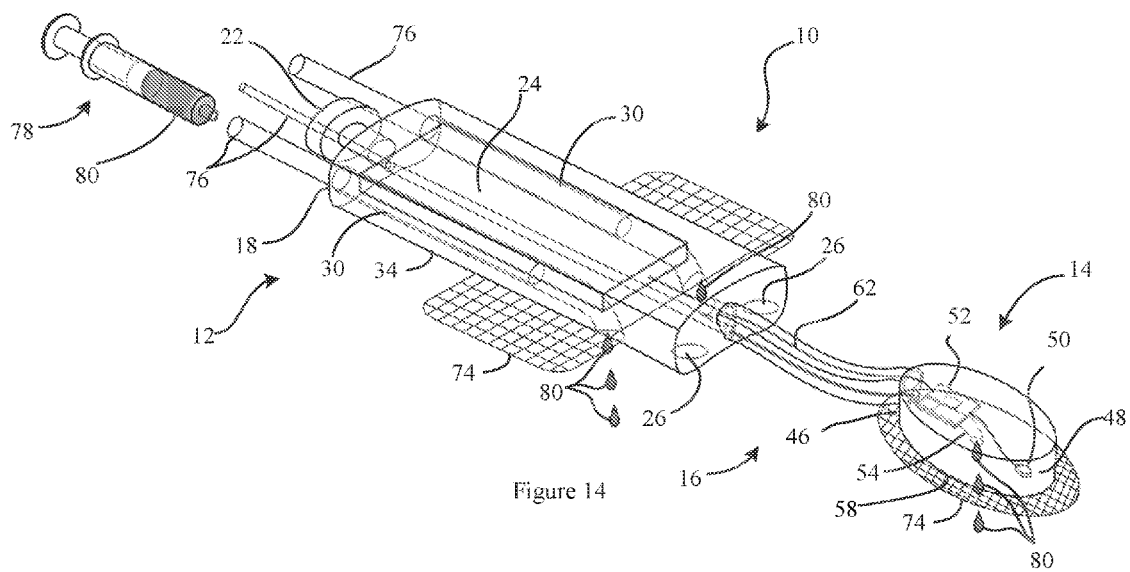
FIG. 14 illustrates the application of adhesive for adhering the polymer mesh of the heart stimulation device shown in FIG. 13 to the epicardial surface according to some embodiments of the present invention.

FIG. 14 illustrates the application of adhesive 80 for adhering the polymer mesh 74 of the implantable heart stimulation device 10 shown in FIG. 13 to the epicardial surface according to some embodiments of the present invention. Once device 10 is positioned at a desired attachment site, a syringe 78 filled with surgical adhesive 80 may couple to a proximal opening of injection port 76 to inject the surgical adhesive 80 into the injection port 76, into the attachment channels 30, 54 and out of the openings 32, 56 of the attachment channels 30, 54, respectively. As the surgical adhesive 80 is urged out of the attachment channels 30, 54 the adhesive 80 may bond the polymer mesh 74 to the epicardial surface of the heart 1. The polymer mesh may be manufactured from known materials such as polyester, PTFE felt, ePTFE, polyurethane foam, polycarbonate foam, combinations thereof, or the like. The polymer mesh could also be made from bio-absorbable material such as Polyglycolide, Polyglycolic acid (PGA) mesh, or the like. The surgical adhesive could be one of or a combination of collagen, Bioglue™ or other surgical adhesives.

Figure 15:
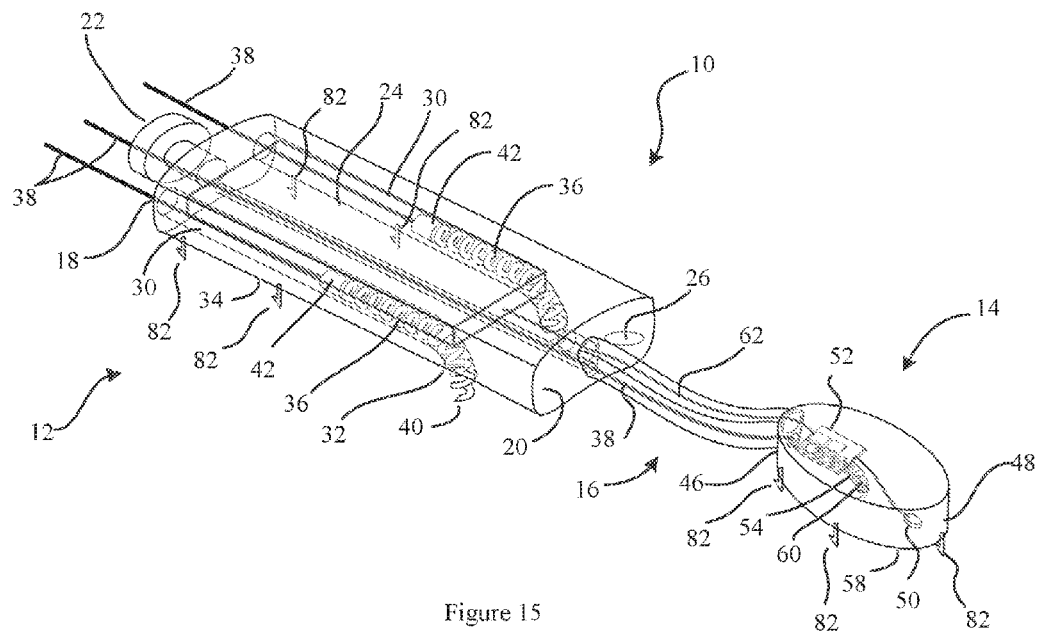
FIG. 15 illustrates an exemplary heart stimulation device using passive anchors in addition to active anchors according to some embodiments of the present invention.
Figure 16:
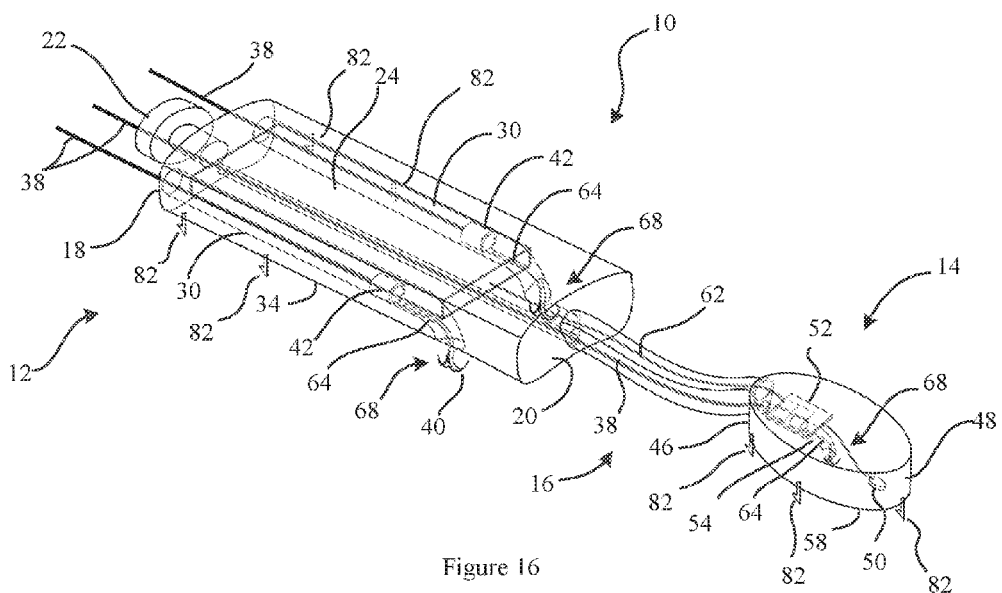
FIG. 16 illustrates another exemplary heart stimulation device using passive anchors in addition to active anchors according to some embodiments of the present invention.

In some embodiments, in addition to using active means (e.g., requiring user actuation) for securing the heart stimulation device 10 to the epicardial surface of the heart 1, passive devices and methods may be used. For example, FIG. 15 illustrates an exemplary implantable heart stimulation device 10 using passive anchors 82 in addition to active anchors 36 according to some embodiments of the present invention. Further, FIG. 16 illustrates another exemplary implantable heart stimulation device 10 using passive anchors 82 in addition to active anchors 64 according to some embodiments of the present invention.

The proximal module 12 may include a plurality of passive anchors 82 that project from the attachment side 34 of the proximal module 12. The distal module 14 may similarly include a plurality of passive anchors 82 that project from the attachment side 58 of the distal module 14. The passive anchors 82 may have a tissue penetrating end with a barb that projects from the tissue penetrating end in the proximal direction. The passive anchors 82 may be manufacture by known techniques such as laser cutting of a sheet of material such as Elgiloy, Stainless steel, Nitinol, or the like and then laser welded to the proximal module 12 and/or distal module 14. The passive anchors may be used in combination with one or more active anchors to provide additional stability or they might be used without active anchors to simplify implantation steps and to simplify pacemaker and catheter designs.

In further aspects of the present invention, delivery devices and methods are provided for delivering an implantable heart stimulation device 10 to an attachment location within the pericardial space of the patient. For example, FIG. 17 illustrates an exemplary delivery catheter 84 for delivering implantable devices (e.g., implantable device 10) to a target implantation site according to some embodiments of the present invention. Delivery catheter 84 may include a handle 86 coupled with a catheter shaft 88 having a distal end 90. The delivery catheter 84 may further include a flush port 92.

Handle 86 may include a number of controllers for user actuation. For example, handle 86 may include a catheter shaft deflection controller 94, an implant release controller 96, a plurality of anchor controllers 100, 102, and a distal module steering controller 104.

The catheter shaft deflection controller 94 may comprise a knob at a distal end of the handle 86 that is actuated by a user by rotation of the knob about the handle axis. The actuation of the catheter shaft deflection controller 94 may deflect the catheter shaft 88 to a curved configuration from a straight configuration of the catheter shaft 88. While illustrated and described with a specific configuration, it should be understood that the illustrated and described deflection controller configuration is exemplary and non-limiting, and that other deflection controller configurations are possible.

The implant release controller 96 may comprise knob at a proximal end of the handle 86 that is actuated by a user by rotation of the knob about the handle axis. The actuation of the implant release controller 96 may actuate an engagement feature 98 of the delivery catheter 84 at the distal end 90 of delivery catheter 84 to disengage with a coupled heart stimulation device, such as a pacemaker, ICD, or the like (e.g., implantable heart stimulation device 10). FIG. 18 illustrates a close up view of the distal end 90 of the delivery catheter 84 shown in FIG. 17 according to some embodiments of the present invention. In the illustrated embodiment 84, the engagement feature 98 comprises a helical coil or screw 98 that may be rotated to disengage with a proximal button 22 of a heart stimulation device 10 (e.g., channel 23 of proximal button 22). While illustrated and described with a specific configuration, it should be understood that the illustrated and described implant release controller configuration is exemplary and non-limiting, and that other implant release controller configurations are possible. Further engagement feature 98 may have other configurations according to some embodiments. For example, engagement feature 98 may be a clamp, a snare, or other engagement feature according to some embodiments of the present invention. The engagement feature 98 may be manipulated (rotated clockwise or counter clockwise, or pulled back and pushed forward) by the release knob 96. The release knob 96 may be connected to release feature 98 by a hollow cable made from stainless steel or Nitinol, a hypo tube made from stainless steel or Nitinol, a tube make from polymer such as PEEK, or the like. The release feature 98 may be configured to a helical shape such as screw to engage to and disengage from the button 22 of the heart stimulation device proximal module by turning the release knob clockwise or counter clockwise. In another embodiment, the feature 98 may be configured to form a clamp appropriately sized to capture the button 22 of the proximal segment of the heart stimulation device 10. The clamp may be configured to open and close by pulling or pushing the detachment knob 98.

Anchor controllers 100, 102 may be torque knobs coupled to stylets 38 to actuate a distal end 103 of the stylets 38. The stylets 38 may extend from the proximal end of the delivery catheter 84 through the handle 86, through the catheter shaft 88, and out the distal end 90 of the delivery catheter 84. As discussed above, the distal ends 103 of the stylets 38 may be configured to couple with a proximal end 42 of the anchors 36, 64. In some embodiments, the distal end 103 of a stylet 38 may have a cross-section that fittingly mates with a proximal end 42 of an anchor 36, 64. For example, in some embodiments, distal end 103 of stylet 38 may have a flat-head cross-section 103a. In some embodiments, distal end 103 of stylet 38 may have a square cross-section 103b. In further embodiments, distal end 103 of stylet 38 may have a hexagonal cross-section 103c.

In some embodiments 84, the anchor controllers 100 may be configured to control stylets 38 inserted within attachment channels 30 of an implantable heart stimulation device 10 for engagement with anchors 36, 64 of a proximal module 12. The anchor controllers 102 may be configured to control a stylet 38 inserted within attachment channel 54 of an implantable heart stimulation device 10 for engagement with anchors 60, 64 of a distal module 14. In some embodiments, the stylet 38 coupled with controller 102 may be inserted through hypo tube stylet 39. While illustrated with two anchor controllers 100, it should be understood that other embodiments may include one or more (e.g., three, four, or more) anchor controllers 100 depending on the number of anchors provided on the heart stimulation device. Further while illustrated with one anchor controller 102, it should be understood that other embodiments may include more than one anchor controllers 102 depending on the number of anchors provided on the distal module 14 of an heart stimulation device. Further, where the heart stimulation device does not include a distal module 14 coupled to a proximal module 12 by a tether 16, the delivery catheter 84 may not have an anchor controller 102 and may only include one or more anchor controllers 100.

In some embodiments 84, a distal module steering controller 104 is provided. The distal module steering controller 104 may be a torque knob coupled with a hypo tube stylet 39 that extends out the distal end 90 of the deliver catheter 84 and may be configured to steer a distal module 14 of an implantable device 10 separate from the proximal end 12. The use of a hypo tube stylet 39 may allow the insertion of a stylet 38 to actuate an anchor in the distal module. The steering of a distal module 14 of an implantable heart stimulation device 10 is illustrated and discussed in more detail below. The hypo tube stylet 39 may be made from material such as stainless steel, Nitinol, a polymer such as PEEK, or the like. In some embodiments, the distal section of the hypo tube stylet may be shaped to a curve with a radius from 5-40 mm or the like, for example, preferably about 10 mm. The hypo tube stylet 39 may be connected to the toque knob 104 on the proximal end. The torque knob 104 is rotatable clockwise and counter clockwise. As the torque knob 104 is rotated, the hypo tube stylet 39 and the curved distal section of the hypo tube stylet are rotated in the same direction as the torque shaft which result in changing the direction of the distal tip of the hypo tube stylet, thereby steering the tip.

As discussed above, delivery catheter shaft 88 may be deflectable. FIG. 19 illustrates the operation of the deflection knob 94 of the delivery catheter 84 shown in FIG. 17 to control the deflection of shaft 88 to reposition the distal end 90 of the delivery catheter 84 according to some embodiments of the invention. Deflection knob 94 may be rotated to controllably deflect shaft 88 from a straight configuration so as to reposition distal end 90 between a distal end position 90*a* and to a distal end position 90*b*. Further, as illustrated, with the deflection of the shaft 88 and the repositioning of distal end 90, the stylets 38 and the distal ends 103 of stylets 38 may also be deflected and repositioned through the actuation of deflection knob 94. Accordingly, deflection knob 94 may control a curvature of shaft 88 so as to reposition the distal end 90 of the delivery catheter 84. The deflection knob 94 may be attached to a pull wire that is connected to the tip 90 of the catheter shaft 88. By rotating the deflection knob 94 in one direction, the pull wire may be pulled to deflect the tip 90 of the catheter shaft 88. By rotating the deflection knob 94 in the opposite direction, the pull wire may be relaxed to remove the deflection at the distal end 90 of the catheter shaft 88. The pull wire may comprise known materials such as stainless steel wire, stainless steel cable, Nitinol wire, Nitinol cable, or the like, and may be attached by known techniques such as laser welding to the distal tip 90 of the catheter shaft 88.

Distal end 90 may be radiopaque in some embodiments. A radiopaque distal end 90 may facilitate implantable device delivery to the attachment site using fluoroscopic guidance, for example. Optionally, devices may be delivered with endoscopic imaging and guidance and may avoid the application of x-ray radiation. Flush port 92 may be provided for introducing solution (e.g., saline) into the catheter shaft 88 for flushing the catheter shaft 88. The flush port 92 may be connected to one or more lumens of the catheter shaft 88 in communication with distal end 90. The flush port may be used to irrigate fluids such as saline through the catheter shaft 88 for enhanced lubricity and removing air form the catheter shaft.

Figure 20:
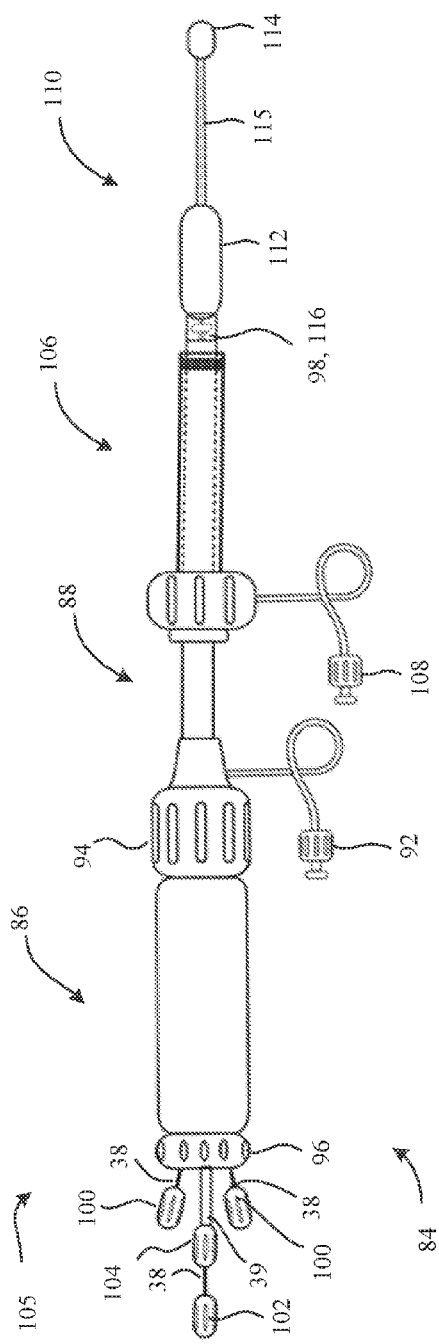
FIG. 20 illustrates a catheter-heart stimulation device assembly according to some embodiments of the present invention.
Figure 21:
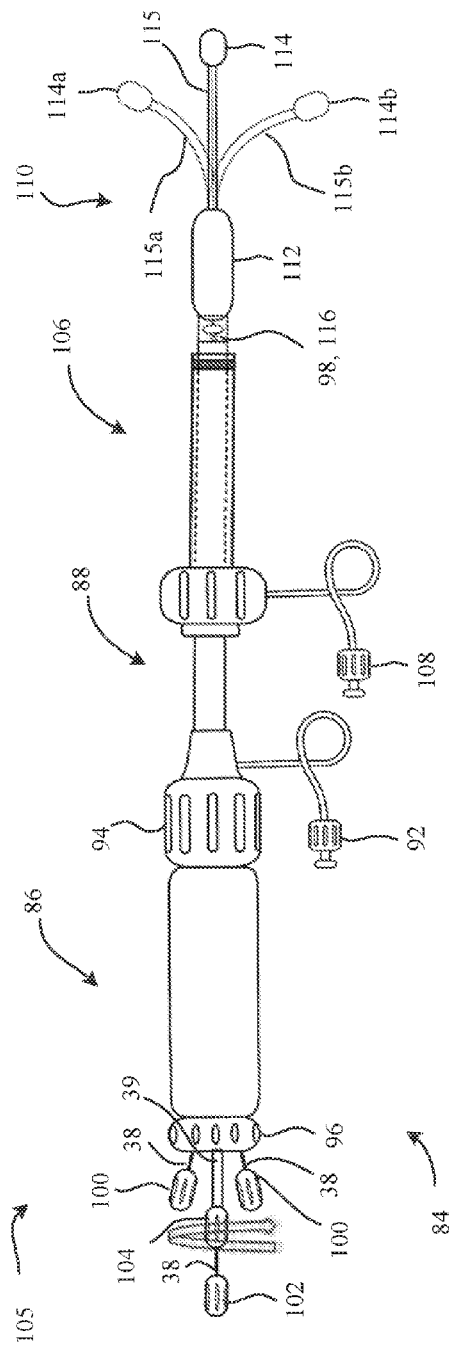
FIG. 21 illustrates the catheter-heart stimulation device assembly shown in FIG. 20 and the operation of a distal module steering knob to control the deflection of the distal module of an exemplary heart stimulation device relative to a proximal module of the exemplary heart stimulation device according to some embodiments of the present invention.

FIG. 20 illustrates a catheter-implant assembly 105 according to some embodiments of the present invention. Catheter-implant assembly 105 includes a delivery catheter 84 releaseably coupled with an implantable heart stimulation device 110. The implantable heart stimulation device 110 includes a proximal module 112, a distal module 114, and a tether 115 coupling the proximal module 112 to the distal module 114. The proximal module 112 may include a button 116 that is releaseably engaged with the engagement feature 98 of the delivery catheter 84. In some embodiments, the implantable heart stimulation device 110 may be delivered to the pericardial space by advancing the implantable heart stimulation device 110 through an introducer sheath 106 that is positioned in the pericardial space. The introducer sheath 106 may include a flush port 108 for introducing solution into the introducer sheath 106 for flushing the introducer sheath 106. The introducer sheath 106 may be manufactured with materials such as Pebax, Nylon, High Density Polyurethane, or the like, and may be reinforced by a coil or braid structure. The flush port 108 may be connected to the center lumen of the introducer 106 to allow fluid communication between the hub and the distal tip of the introducer sheath 106. The hub of the introducer sheath 106 may include a gasket to provide a seal to prevent back flow of fluid from the hub of the introducer sheath 106. The gasket may also be used to provide a seal as the heart stimulation device is inserted into the introducer sheath 106 to prevent leakage of fluid from the hub FIG. 21 illustrates the catheter-implant assembly 105 shown in FIG. 20 and the operation of a distal module steering knob 104 to control the deflection of the distal module 114 of an exemplary implantable heart stimulation device 110 relative to a proximal module 112 of the exemplary implantable heart stimulation device 110 according to some embodiments of the present invention. As mentioned above, a distal module steering knob 104 may be rotated to increase a curvature of tether 115 to deflect the distal module 114 from a straight configuration and to controllably reposition the distal module 114 between distal module position 114*a* and to distal module position 114*b*. Accordingly, in some embodiments, the distal module steering knob 104 may be actuated to control a curvature of tether 115 for selectively sweeping the distal module 114 relative the proximal module 112. By rotating the steering knob 104 the curved stylet may be rotated to the left and right thus increasing the curvature of tether 115 to steer (sweep) the distal module 114 on the epicardial surface of the heart.

Figure 22:
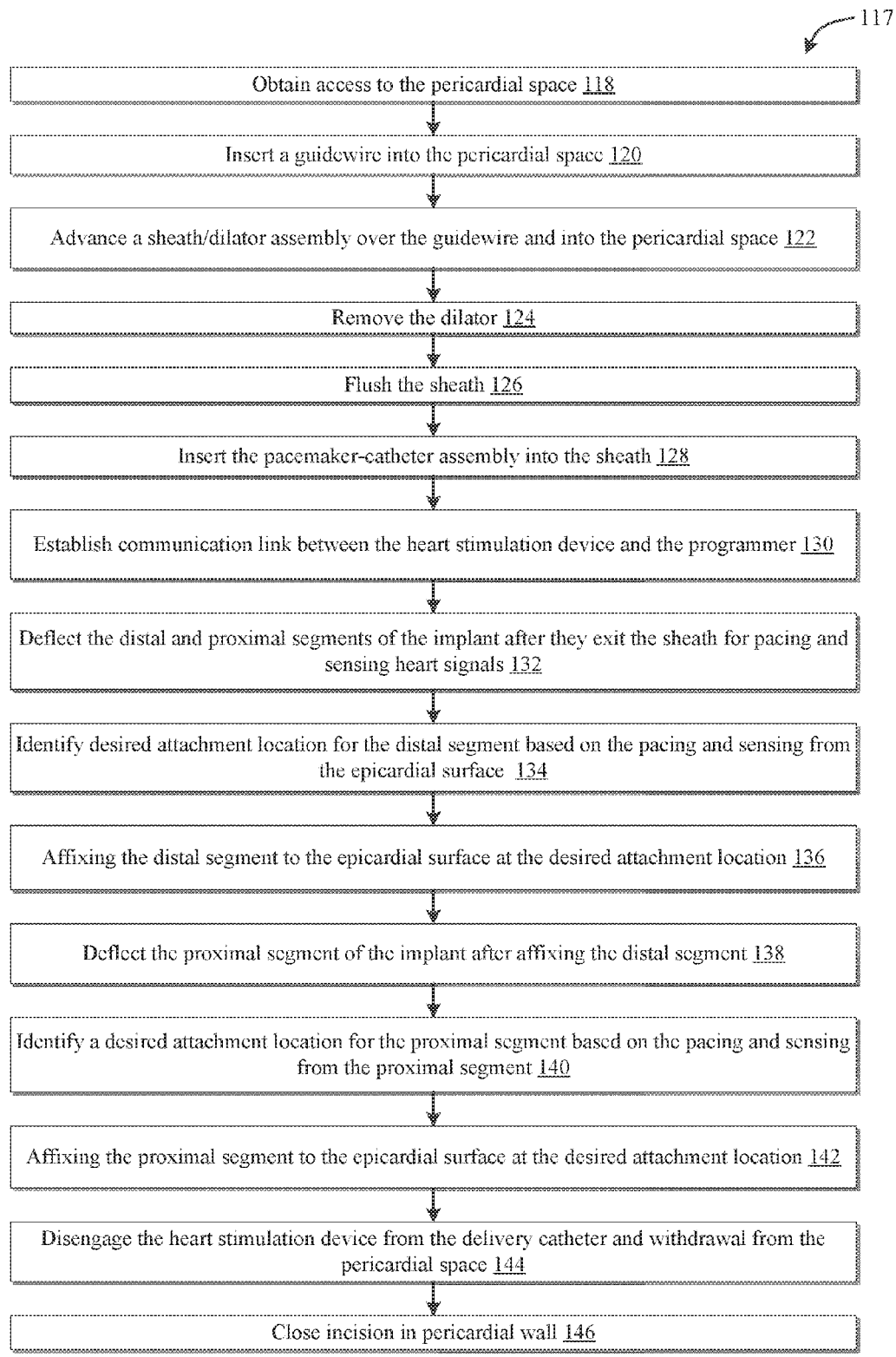
FIG. 22 illustrates an exemplary implantation method according to some embodiments of the present invention.

In further aspects of the present invention, methods of delivering and attaching an implantable heart stimulation device to the epicardial surface of the heart are provided. FIG. 22 illustrates an exemplary implantation method 117 according to some embodiments of the present invention. The method 117 may start by obtaining access to the pericardial space of the patient 118. A guidewire may be inserted into the pericardial space 120. An introducer sheath (e.g., introducer sheath 106) and dilator assembly may be advanced over the guidewire and into the pericardial space 122. A dilator 124 may be removed. The introducer sheath (e.g., introducer sheath 106) may be flushed. A catheter-implant assembly (e.g., catheter-implant assembly 105) may be inserted through the introducer sheath 128 to insert the heart stimulation device into the pericardial space. A communication link may be established between the heart stimulation device and the programmer 130. A distal and proximal module of the heart stimulation device may be deflected after they exit the sheath for pacing and sensing heart signals 132 from various regions of the epicardial surface of the heart 1. A desired attachment location for the distal module may be identified based on the pacing and sensing from the epicardial surface 134. The distal module may be affixed to the epicardial surface at a desired attachment location 136. The proximal module of the implant may be deflected after affixing the distal module 138. A desired attachment location for the proximal module may be identified based on the pacing and sensing from the proximal module 140. The proximal module may be affixed to the epicardial surface at the desired attachment location 142. The heart stimulation device may then be disengaged from the delivery catheter and the delivery catheter may be withdrawn from the pericardial space 144. Thereafter, the incision in the pericardial wall may be closed 148.

Figure 23:
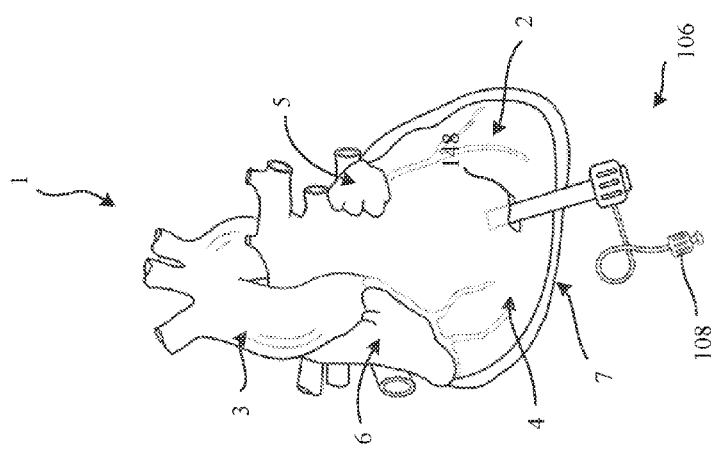
FIG. 23 illustrates the incision of the pericardium and the introduction of an introducer sheath for the purposes of implanting a heart stimulation device into the pericardial space of a patient according to some embodiments of the present invention.

FIG. 23 illustrates an exemplary method of obtaining access to the pericardial space of a patient 118. In some embodiments, the pericardium may be accessed by a sub-xiphoid surgical approach. An incision 148 of the pericardium can be made and a guidewire inserted through the incision 148. An introducer sheath 106 may be advanced over the guidewire to provide access to the pericardial space 122. Optionally, a dilator may be used to facilitate the insertion of the introducer sheath 106 into the pericardial space. After the introducer sheath 106 is in place, the dilator may be removed 124. If needed, the introducer sheath 106 may be flushed 126 by introducing solution (e.g., saline) into flush port 108. Accordingly, in some embodiments, methods of implantation may avoid a transvascular approach such as a transfemoral implantation method. Further, in some embodiments, methods of implantation may avoid the need for introducing contrast agents into the blood for visualizing a position of the device within the vasculature.

Figure 24:
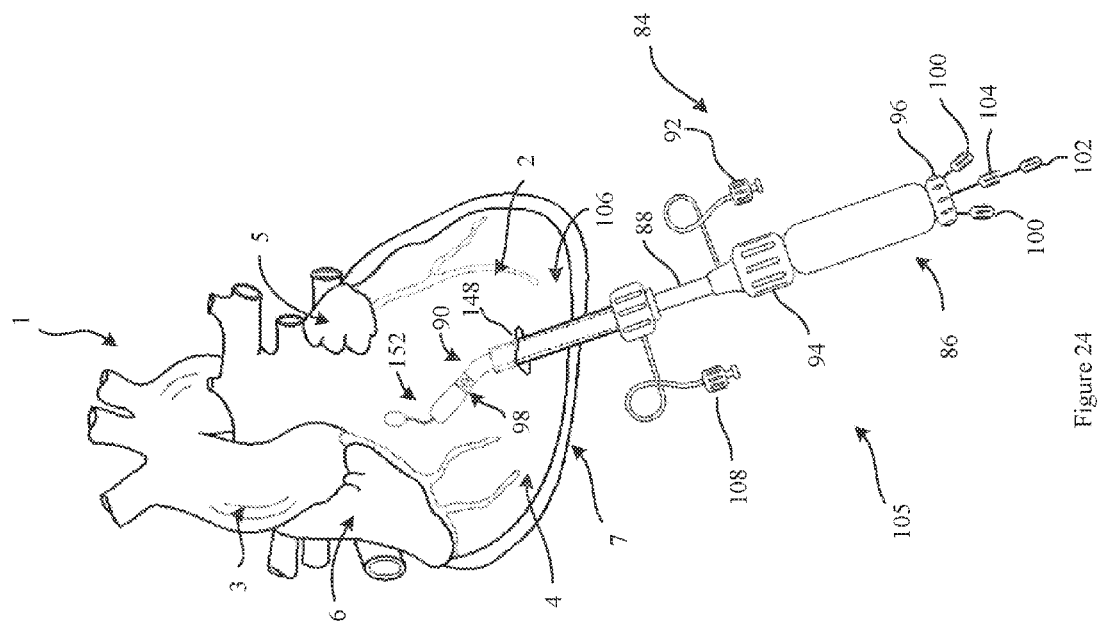
FIG. 24 illustrates the introduction of a heart stimulation device into the pericardial space by introducing the catheter-heart stimulation device assembly through the introducer sheath according to some embodiments of the invention.

FIG. 24 illustrates the introduction of an implantable heart stimulation device 152 into the pericardial space by introducing 128 the catheter-implant assembly 105 through the introducer sheath 106 according to some embodiments of the invention. Implantable heart stimulation device 152 may include a proximal module, a distal module, and a tether coupling the proximal module to the distal module. The implantable heart stimulation device 152 may include a proximal button that releaseably couples the implantable device 152 with the engagement feature 98 of the delivery catheter 84.

A communication link between the heart stimulation device 152 and a programmer 154 may be established. The communication link may be through wireless communication (e.g., sending and receiving RF signals, Bluetooth communications link, WiFi standards, or the like). The programmer 154 may also communicate with one or both modules of the heart stimulation device by conducting communication using the patient's electrically conducting tissue, using surface electrodes placed on the body of the patient (similar to obtaining electrocardiogram (ECG) signals), or the like. The heart stimulation device programmer may receive natural heart beat signals from the heart 1 of the patient and may be configured to program the stimulating and/or pacing of the heart stimulation device 152 depending on the application and attachment of the heart stimulation device 152.

After the heart stimulation device 152 is positioned in the pericardial space of the heart 1, the heart stimulation device 152 may be deflected and swept across and over the epicardial surface of the heart for testing pacing and sensing thresholds 132. A desired attachment location for the device 152 may be identified based on the pacing and sensing from the epicardial surface 134, 140.

Figure 25:
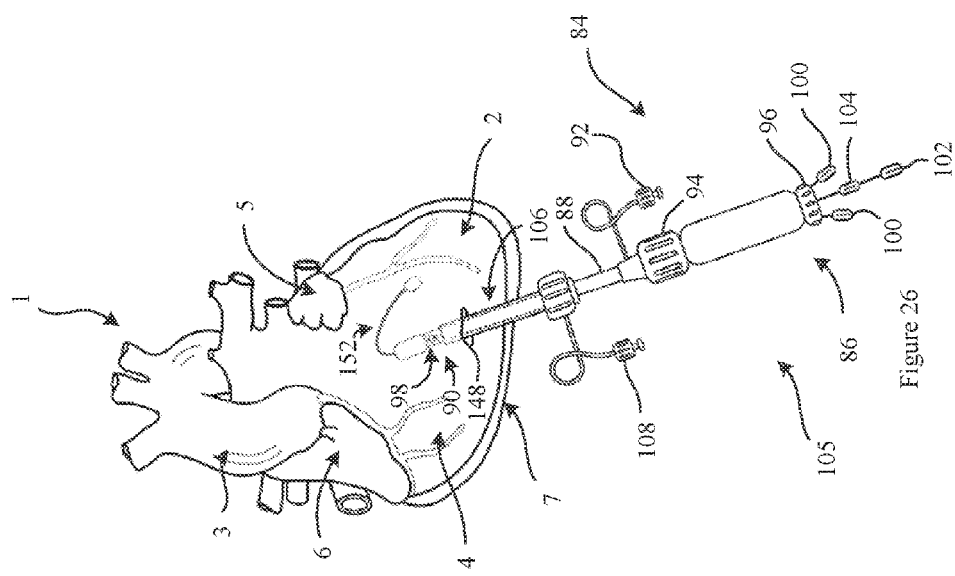
FIG. 25 illustrates the operation of the deflection knob of the delivery catheter during heart stimulation device implantation for identifying a desired implantation site within the pericardial space of the patient according to some embodiments of the invention.

FIG. 25 illustrates the operation of the deflection knob 94 of the delivery catheter 84 during device 152 implantation for sweeping the device 152 over the surface of the heart to identify a desired implantation site within the pericardial space of the patient according to some embodiments of the invention. Further as mentioned above, the distal module of heart stimulation device 152 may be steered separately from the proximal module of the device 152 by actuating a distal module steering controller 104. Thus, in some embodiments, the distal module may be swept over the epicardial surface for testing pacing and sensing thresholds separately from the proximal module of device 152.

Advantageously, pericardial fluid in the pericardial space may facilitate sweeping of the device 152 over the epicardial surface of the heart 1 as it naturally reduces friction and provides lubrication so that the pericardium glides over the heart surface with each heartbeat. Further, in some embodiments, heart stimulation device 152 may have a delivery configuration where anchors or other attachment features are retracted from an attachment side of the heart stimulation device 152. The delivery configuration of implantable heart stimulation device 152 may further facilitate sweeping of the heart stimulation device 152 over the epicardial surface for testing pacing in sensing thresholds with a retracted attachment feature (e.g., helical screw, barb, shape-memory barb, or the like). Accordingly, in some embodiments, testing pacing and sensing thresholds may be conducted without having to anchor the device 152 into the tissue at multiple sites and may thereby reduce the amount of trauma to the tissue during the identification of a preferred attachment location.

After identifying a desired attachment location for the distal module 134 and attaching the distal module to the desired attachment location 136, the flexible tether may allow the proximal module to be deflected or steered over the epicardial surface of the heart 138 for testing pacing and sensing thresholds while the distal module is affixed. Accordingly, a desired attachment location for the proximal module may be identified 140 after attaching the distal module, according to some embodiments.

Figure 26:
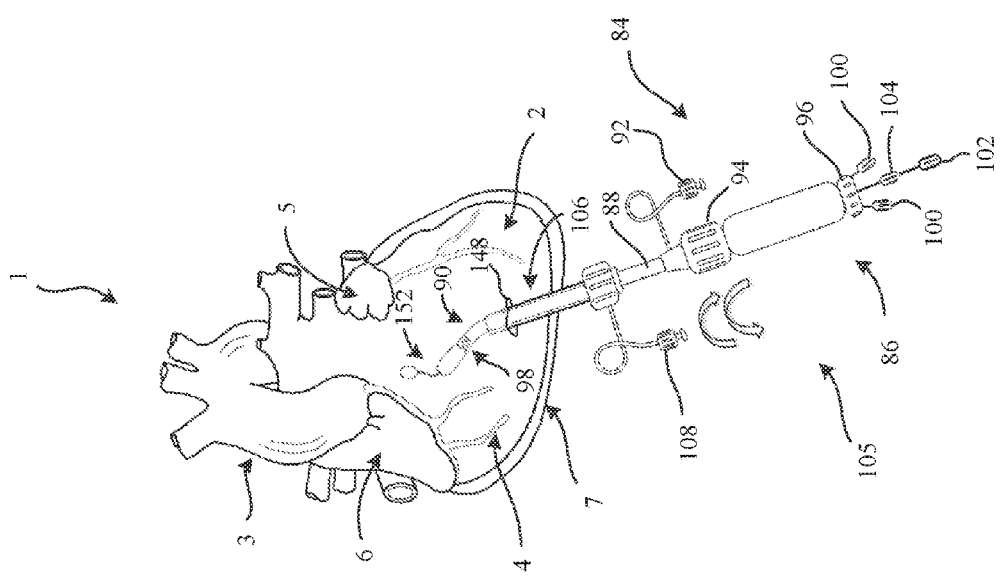
FIG. 26 illustrates the exemplary placement of the distal module and the proximal module of an exemplary heart stimulation device for bi-ventricular stimulating and/or pacing according to some embodiments of the present invention.

FIG. 26 illustrates the exemplary placement of the distal module and the proximal module of an exemplary heart stimulation device 152 for bi-ventricular stimulating and/or pacing according to some embodiments of the present invention. In FIG. 26, the distal module may be attached over the left ventricle to stimulate and/or pace the left ventricle and the proximal module may be placed on the right ventricle to stimulate and/or pace the right ventricle. Accordingly the heart stimulation device 152 may be attached and programmed to provide for bi-ventricular stimulating and/or pacing according to some embodiments. In further embodiments the distal module may be attached over the right ventricle and the proximal module may be attached over the left ventricle to provide bi-ventricular stimulating and/or pacing.

Figure 27:
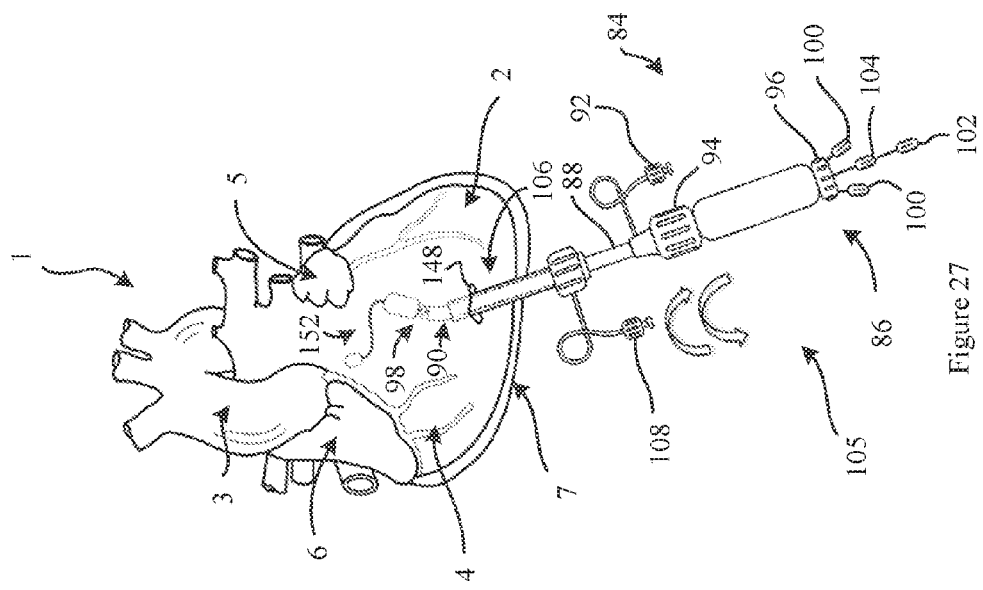
FIG. 27 illustrates the exemplary placement of the distal module and the proximal module of an exemplary heart stimulation device for dual chamber stimulating and/or pacing according to some embodiments of the present invention.

FIG. 27 illustrates another exemplary placement of the distal module and the proximal module of an exemplary heart stimulation device 152 for dual chamber stimulating and/or pacing according to some embodiments of the present invention. In FIG. 27, the distal module may be placed over the right atrium to stimulate and/or pace the right atrium and the proximal module may be placed on the right ventricle to stimulate and/or pace the right ventricle. Accordingly, the device 152 may be attached and programmed to provide dual-chamber stimulating and/or pacing according to some embodiments.

Figure 29:
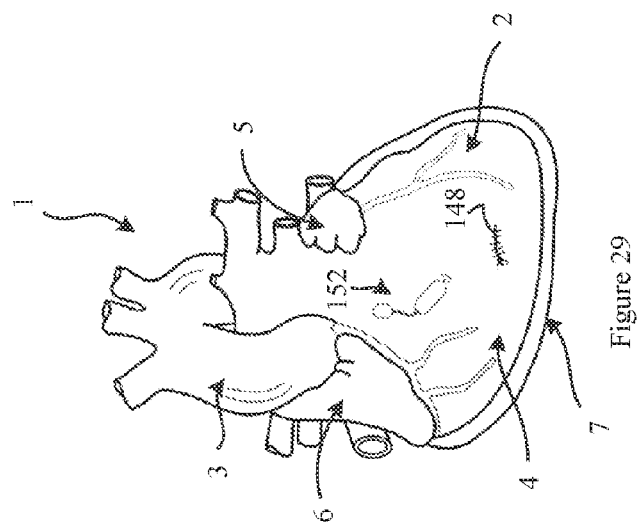
FIG. 29 illustrates the removal of the introducer sheath from the pericardial space and the suturing of the incision of the pericardium according to some embodiments of the present invention.
Figure 28:
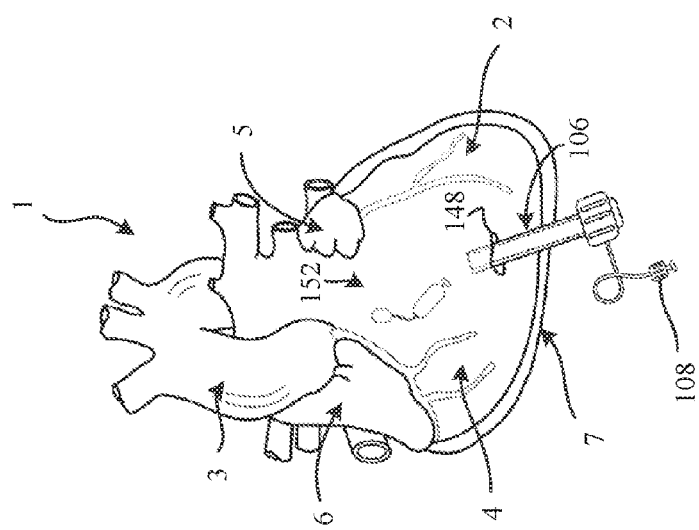
FIG. 28 illustrates the implantation of the exemplary heart stimulation device and the withdrawal of the delivery catheter from the pericardial space according to some embodiments of the present invention.

FIG. 28 illustrates the implantation of the exemplary heart stimulation device 152 and the withdrawal of the delivery catheter 84 from the pericardial space according to some embodiments of the present invention. Once the heart stimulation device 152 is desirably attached to the epicardial surface of the heart 1, the heart stimulation device 152 may be released from the delivery catheter 84 by actuating the release controller 96. After the heart stimulation device 152 has been released, the delivery catheter 84 may be withdrawn through the introducer sheath 106 and from the pericardial space. Thereafter, the introducer sheath 106 may be removed from the pericardial space and the incision 148 of the pericardium may be sutured according to some embodiments of the present invention, as illustrated in FIG. 29.

Advantageously, the heart stimulation device (e.g., pacemaker, ICD, or the like) may be implanted on the epicardial surface of the heart and outside the blood flow of the patient. Thus such implantation methods and devices may avoid risks associated with thrombus formation and clot debris being dislodged and traveling in the blood to the brain, heart, or lungs and potentially causing stroke, myocardial infarctions, and/or pulmonary embolisms in a patient. Further the heart stimulation device implantation approach may be simplified be accessing an implantation site through a subxiphoid surgical approach rather than through a transvascular approach such as a transfemoral approach. Optionally, the implantation procedure may be performed under fluoroscopic guidance. Endoscopic cameras may be used to avoid the use of x-ray imaging techniques.

While illustrated and described as implanting a heart stimulation device 152 having a proximal and a distal module, it should be understood that the description and illustration of the method 171 is provided by way of example only. In further embodiments, the method described and illustrated above may be applied to heart stimulation devices which only include a single module. The single module may be attached and configured to stimulate and/or pace an individual chamber of the heart. Further, other embodiments may be provided where three or more tethered modules are provided. For example, a first module may be provided to stimulate and/or pace the right atrium, a second module may be provided to stimulate and/or pace the right ventricle, and a third module may be provided to stimulate and/or pace the left ventricle. In yet further embodiments, multiple individual modules may be implanted within the pericardial space that may wirelessly communicate. The individual modules may wirelessly communicate with a heart stimulation device programmer and/or with each of the other implanted heart stimulation modules.

Figure 30:
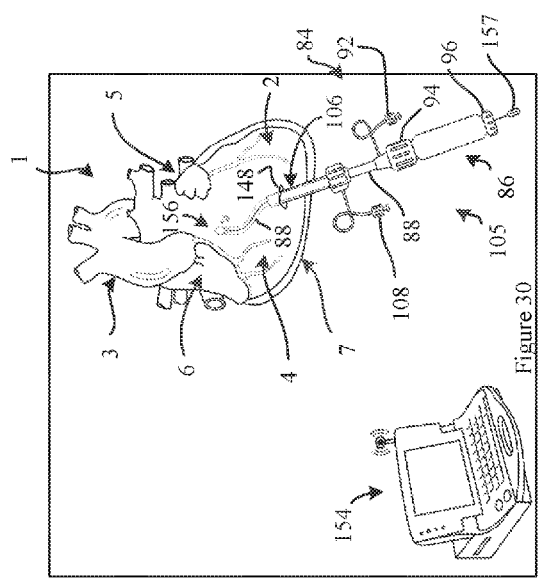
FIG. 30 illustrates the implantation of an exemplary heart stimulation device to the pericardial space of a patient that wirelessly communicates to a heart stimulation device programmer according to some embodiments of the invention.

For example, FIG. 30 illustrates the implantation of an exemplary implantable heart stimulation device 156 to the pericardial space of a patient that wirelessly communicates to a heart stimulation device programmer 154 according to some embodiments of the invention. As illustrated in FIG. 30, a catheter-implant assembly 105 may be inserted through introducer sheath 106 to advance implant 156 into the pericardial space of the patient. Heart stimulation device 156 may comprise a single stimulation module. For example, the heart stimulation device 156 may include an electrode, battery, communications board, pulse generator, and device controller.

Similar to methods disclosed above, the device 156 may be swept over the epicardial surface for testing pacing and sensing threshold for identifying a preferred attachment location. For example, the heart stimulation device 156 may be attached for stimulating and/or pacing the right atrium, the right ventricle, the left atrium, or the left ventricle. The heart stimulation device 156 may then be attached to the epicardial surface of the heart 1 by actuating anchor control knob 157 of the delivery catheter 84. While illustrated with a single anchor knob 157 for deploying an anchor of heart stimulation device 156, it should be understood that in other embodiments, heart stimulation device 156 may include a plurality of anchors deployable by a plurality of anchor knobs 157. Additionally, it should be understood that in some embodiments, heart stimulation device 156 may include a polymer mesh on the attachment side of heart stimulation device 156 and may attach to the epicardial surface by injecting a surgical adhesive to bond the polymer mesh to the epicardial surface. In such an embodiment, the heart stimulation device 156 may not include an anchor and the delivery catheter 84 may not need any anchor control knobs 157.

Figure 31:
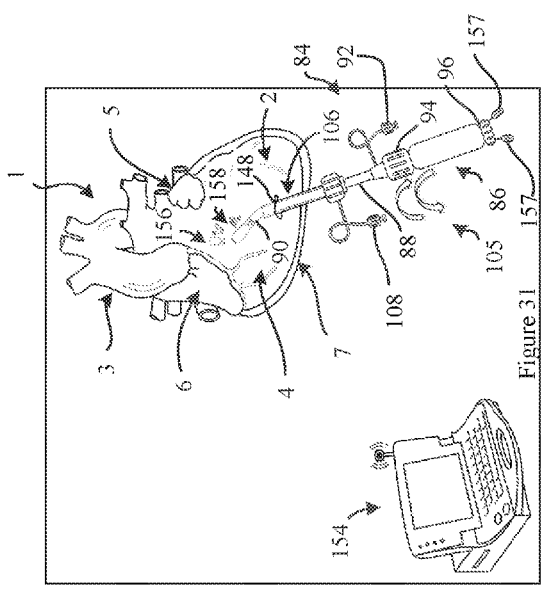
FIG. 31 illustrates the implantation of another exemplary heart stimulation device to the pericardial space of the patient that wirelessly communicates to the heart stimulation device programmer and the heart stimulation device of FIG. 30 according to some embodiments of the present invention.

After device 156 attachment to the epicardial surface and release using controller 96, the method may end. In other embodiments, the operation may continue as illustrated in FIG. 31. FIG. 31 illustrates the implantation of another exemplary implantable heart stimulation device 158 to the pericardial space of the patient that wirelessly communicates to the heart stimulation device programmer 154 and the implantable heart stimulation device 156 of FIG. 30 according to some embodiments of the present invention. Implantable heart stimulation device 158 may also be a single stimulation module and may be complementary to heart stimulation device 156 for providing therapeutic treatment. As illustrated, implantable heart stimulation device 158 may be advanced into the pericardial space by inserting a catheter-implant assembly 105 through introducer sheath 106. The catheter-implant assembly 105 may utilize the same catheter 84 as used in FIG. 30 for the implantation of heart stimulation device 156. For example, after implantation of heart stimulation device 156, the catheter 84 may be removed and loaded with heart stimulation device 158 such that the catheter 84 is reused for the implantation of heart stimulation device 158. In such embodiments, heart stimulation device 156, heart stimulation device 158, and catheter 84 may be provided together in a kit and delivery catheter 84 may be configured to deploy the heart stimulation device 156, 158 individually. In other embodiments, catheter-implant assembly 105 illustrated in FIG. 31 may be a completely separate assembly 105 with a new delivery catheter 84 releaseably coupled to heart stimulation device 158. In such embodiments, the catheter-implant assemblies 105 may come preassembled in kits and the delivery catheter 84 may be a single use device and/or disposable.

Heart stimulation device sweeping over the epicardial surface may be performed to identify the desired attachment location for heart stimulation device 158. Heart stimulation device 158 may be attached to stimulate and/or pace the right atrium, the right ventricle, the left atrium, or the left ventricle, for example. Device 158 may be a module of a different size. In FIG. 31, heart stimulation device 158 is larger than heart stimulation device 156. The size difference may be due to different battery capacities and/or different functions (e.g., defibrillating vs. pacing, etc.), for example. Optionally, a larger module 158 may be secured by the actuation of two anchor control knobs 157 of catheter 84 for attachment to the epicardial surface.

In FIG. 31, heart stimulation device 156 may be positioned for stimulating and/or pacing the right atrium, however as discussed above, the heart stimulation device 156 may optionally be placed for stimulating and/or pacing the left atrium, the left ventricle, or the right ventricle. Optionally, heart stimulation device 158 may be positioned to stimulate and/or pace the right ventricle so that heart stimulation device 156, 158 provide dual chamber stimulating and/or pacing. It should be understood that the attachment locations of devices 156, 158 may be switched such that heart stimulation device 156 stimulates and/or paces the right ventricle and heart stimulation device 158 stimulates and/or paces the right atrium. After attachment, the heart stimulation device 158 may be released via controller 96.

Figure 32:
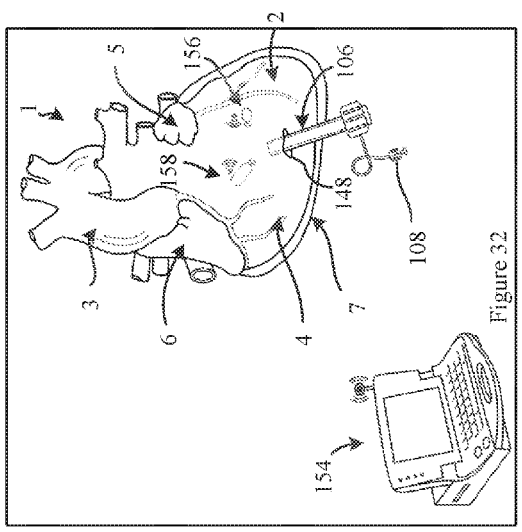
FIG. 32 illustrates the removal of the delivery catheter from the pericardial space according to some embodiments of the present invention.

In other embodiments, as illustrated in FIG. 32, heart stimulation device 156 may be positioned to stimulate and/or pace the left ventricle and device 158 may be positioned to stimulate and/or pace the right ventricle such the heart stimulation device 156, 158 provide bi-ventricular stimulating and/or pacing. Other device arrangements are possible according to embodiments of the invention.

Figure 33:
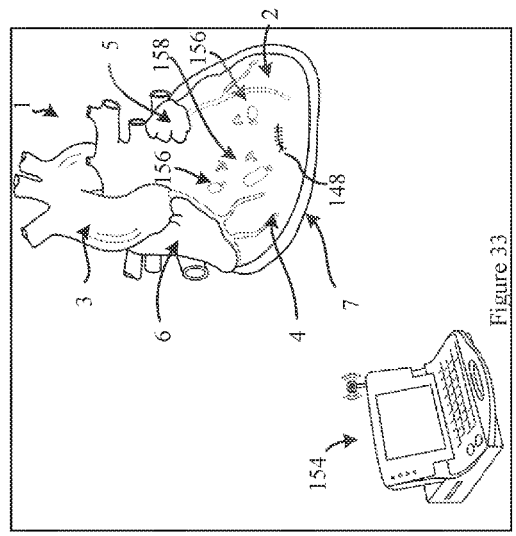
FIG. 33 illustrates the implantation of a plurality of heart stimulation devices to the pericardial space where each of the plurality of heart stimulation devices wirelessly communicate with each other and with a heart stimulation device programmer according to some embodiments of the present invention.

For example, FIG. 33 illustrates the implantation of a plurality of implantable heart stimulation device (i.e., heart stimulation device 156 (×2) and heart stimulation device 158) to the pericardial space where each of the plurality of implantable heart stimulation device wirelessly communicate with each other and with a heart stimulation device programmer 154 according to some embodiments of the invention. The plurality of devices may be implanted using the methods described above. Optionally, separate catheter-implant assemblies 105 may be used. Further, methods may include reloading a single catheter 84 with the following device (e.g., device 156, 158) to be implanted. In FIG. 31, one device 156 is placed for stimulating and/or pacing the left ventricle, one heart stimulation device 156 is placed for stimulating and/or pacing the right atrium, and another heart stimulation device 158 is placed for stimulating and/or pacing the right ventricle. It should be understood that other attachment arrangements are possible and the illustrated and described arrangement is provided by way of example only. Further, other combinations of heart stimulation device 156, 158 may be used. For example, in some embodiments, only heart stimulation device 156 are implanted. In other embodiments, only heart stimulation device 158 are implanted. In even further embodiments, a plurality of heart stimulation device 158 are implanted and a single heart stimulation device 156 is implanted. In still further embodiments, a plurality of heart stimulation device 158 are implanted and a plurality of heart stimulation device 156 are implanted.

Figure 34:
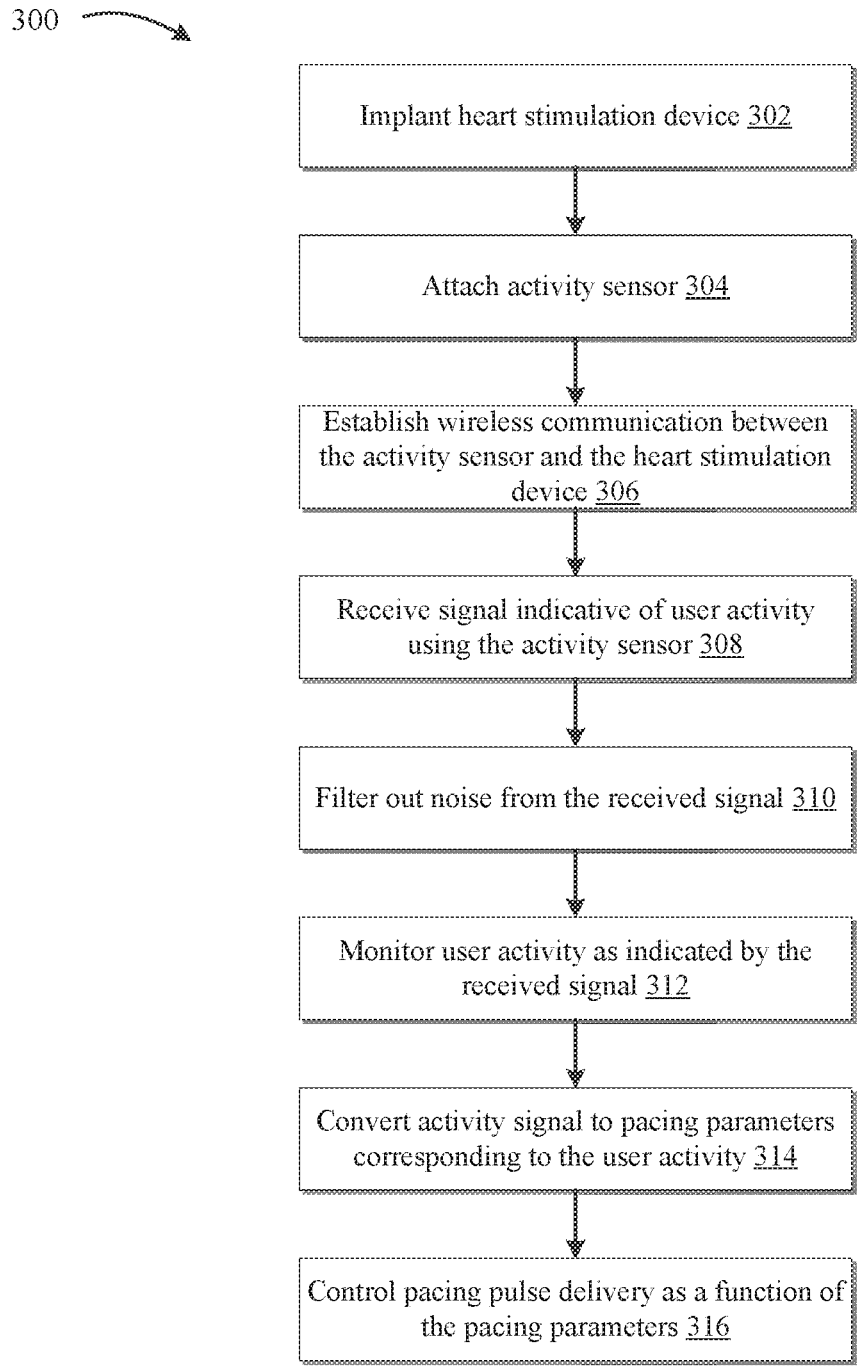
FIG. 34 illustrates an exemplary method of attaching an activity level sensor that transmits a signal indicative of the activity of the user to the one or more implanted heart stimulation devices for adjusting a stimulating and/or pacing pulse delivery in response to the indicated level of activity of the user according to some embodiments of the present invention.

In further aspects of the present invention, implantation methods (e.g., implantation method 117) may further include attaching and/or implanting an activity level sensor to a portion of the patient. For example, FIG. 34 illustrates an exemplary method 300 according to some embodiments of the present invention. The method 300 may including implanting a heart stimulation device 302 and attaching an activity level sensor 304 to the patient. A wireless communication between the activity level sensor and the heart stimulation device may be established 306. A signal indicative of user activity may be received using the activity level sensor 308. Noise may be filtered from the received signal 310. A user activity level may be monitored 312. The activity level signal may be converted to stimulating and/or pacing parameters corresponding to the user activity level 314. Stimulating and/or pacing pulse delivery may then be controlled as a function of the stimulating and/or pacing parameters 316.

A heart stimulation device may be implanted 302 according to one or more methods described above. For example, a heart stimulation device may be attached along an epicardial surface of the heart for electrically stimulating the epicardial surface. In other embodiments, the heart stimulation device may be an intracardiac device, such as a pacemaker implanted within a chamber of the heart.

An activity level sensor may be attached to the patient 304 (e.g., inner surface of the sternum, ribs, collar bone, or implanted within tissue pockets, or the like) using one or more of the methods described above. The activity sensor may be implanted in the pleural cavity by catheter and surgical techniques describe above, through a sub xyphoid surgical access technique or the like. Preferably the attachment or implantation location has minimal relative motion with respect to the patient's heart. The activity level sensor may be configured to provide activity level data and the data may be transmitted to the heart stimulation device. In response to receiving the activity level data, the heart stimulation device may adjust stimulation of the heart based on the activity level data received from the activity level sensor. In some embodiments, an activity level sensor may be included in a kit with one or more implantable heart stimulation devices. The kit may further include a delivery catheter (e.g., delivery catheter 84) according to some embodiments of the invention. In some embodiments, the activity level sensor may be included in a kit where the implantable heart stimulation device is preassembled with the delivery catheter (e.g., delivery catheter 84) to form a delivery catheter-heart stimulation device assembly (e.g., assembly 105).

Figure 35:
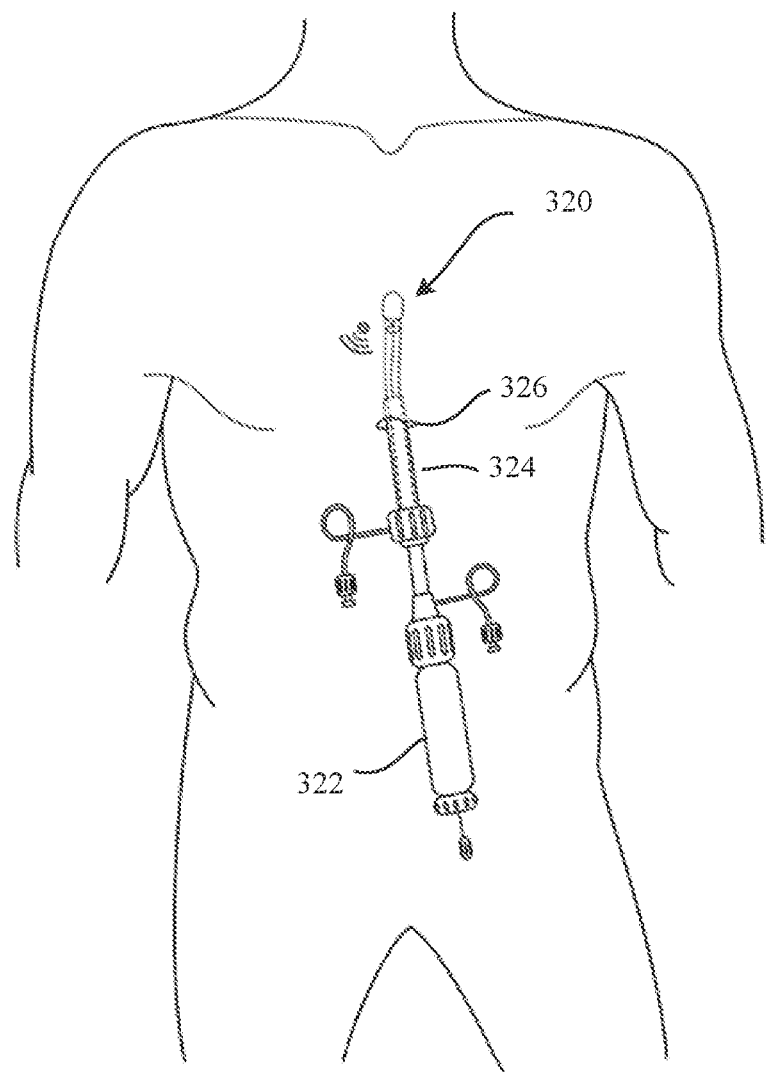
FIG. 35 illustrates an implantation of the activity level sensor to the sternum or parietal pleura according to some embodiments of the present invention.

The activity level sensor may have a similar configuration as the heart stimulation devices described above and may be deliverable with the delivery catheter devices described above in a similar manner. For example, FIG. 35 illustrates the insertion and attachment of an activity level sensor 320 to a posterior surface of a sternum or the ribs of a patient utilizing a delivery catheter 322 according to some embodiments. The activity level sensor 320 may include a battery, an accelerometer, and a communications board for establishing a communication link with one or more heart stimulation devices. The activity level sensor 320 may further include a proximal button that is configured in a similar manner to the proximal button described above with regard to the heart stimulation devices. The proximal button may be configured to releasably engage with the distal end of the delivery catheter 322. For example, the proximal button may include an engagement channel for receiving an engagement feature (e.g., helical coil, or the like) of the delivery catheter 322. The activity level sensor 320 may further include one or more attachment channels that extends from a proximal end of the activity level sensor 320 to an opening on an attachment side of the activity level sensor 320. The channel may include an anchor with a distal tissue engaging end and a proximal stylet engaging end. The anchor may be a helical coil or a shape-memory barb as described above. Optionally, the attachment side of the activity level sensor 320 may include a polymer mesh such that surgical adhesive may be advanced through the channel and out the opening on the attachment side of the activity level sensor 320 to adhere the polymer mesh of the activity level sensor 320 to the tissue of the patient.

The delivery catheter 322 may include a handle, coupled with a delivery catheter shaft that extends to a distal end of the delivery catheter shaft. The delivery catheter 322 may further include a flush port, a deflection knob for controllably deflecting the shaft of the delivery catheter 322. A release controller may control the engagement of the activity level sensor 320 with the distal end of the catheter 322. One or more anchor controllers may be provided that couple with one or more stylets that extend through the delivery catheter 322 and into the one or more anchor channels of the activity level sensor 320. The anchor controllers may be actuated to deploy the one or more anchors of the activity level sensor 320 to attach the activity level sensor to the tissue of the patient.

The activity level sensor 320 may be advanced into the patient by sub xiphiod surgical technique, incising the skin of the patient and advancing an introducer sheath 324 through the incision 326. The introducer sheath 324 may include a flush port. Thereafter, the activity level sensor-catheter assembly 320, 322 may be advanced through the introducer sheath 324. The activity level sensor 320 may then be deployed to a desired attachment location utilizing one of the methods described above (e.g., introducing surgical glue to adhere the device to the attachment location, advancing one or more shape-memory barbs, actuating one or more helical coils, or the like). After attachment, the delivery catheter 322 may disengage with the activity level sensor 320 and may then be withdrawn from the patient.

Figure 36:
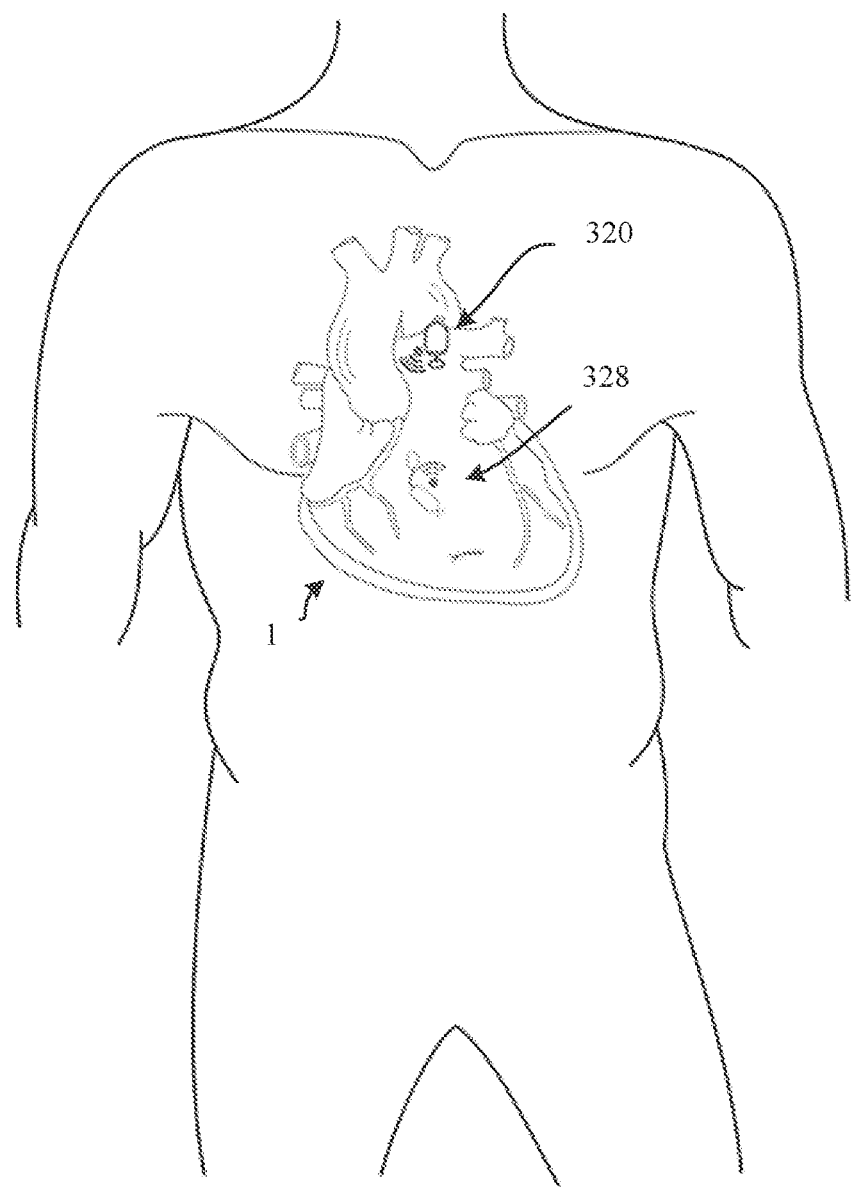
FIG. 36 illustrates the wireless communication between the activity level sensor and an implanted heart stimulation device according to some embodiments of the present invention.

FIG. 36 illustrates the attachment of the activity level sensor 320 to the inner surface of the sternum of a patient and the attachment of a heart stimulation device 328 along the epicardial surface of the heart 1. While illustrated as having two modules coupled by a tether, it should be understood that heart stimulation device 328 may have other configurations according to some embodiments. FIG. 36 also shows a wireless communication link (e.g., by RF signal link, Bluetooth communication, WiFi standards, or the like) between the heart stimulation device 328 and the activity level sensor 320 may be established 306.

After the communication link is established, the heart stimulation device 328 may receive a signal indicative of user activity level from the activity level sensor 308. The activity level sensor 320 may include one or accelerometers in some embodiments. The one or more accelerometers may include one or more single-axis accelerometers and/or one or more multi-axis accelerometers. Noise may be filtered out from the received signal 310.

The one or more accelerometers of an attached activity level sensor may provide acceleration data of the patient and the acceleration data may be correlated with a user activity level so as to monitor a user activity level 312. For example, an accelerometer of an attached activity level sensor 320 may measure little to no acceleration changes over time when a patient sleeping, sitting, or otherwise resting. In contrast, an accelerometer of an attached activity level sensor 320 may measure greater acceleration changes over time when a patient is engaged in increased physical activity, such as walking, running, etc.

The activity signal may be converted to stimulating and/or pacing parameters corresponding to the user activity 314. For example, particular stimulating and/or pacing parameters may be retrieved when the activity level signal is indicative of a patient resting (e.g., minimal accelerometer measurements, intermittent measurements, or the like). Further, particular stimulating and/or pacing parameters may be retrieved when the activity level signal is indicative of a patient engaged in activity (e.g., walking, running, etc.). In some embodiments, different pacing parameters may be retrieved depending on whether the monitored activity level is indicative of low user activity, medium user activity, or high user activity. After retrieving preferred parameters based on the activity level, heart stimulation may be controlled based on the retrieved stimulating and/or pacing parameters 316.

Figure 37:
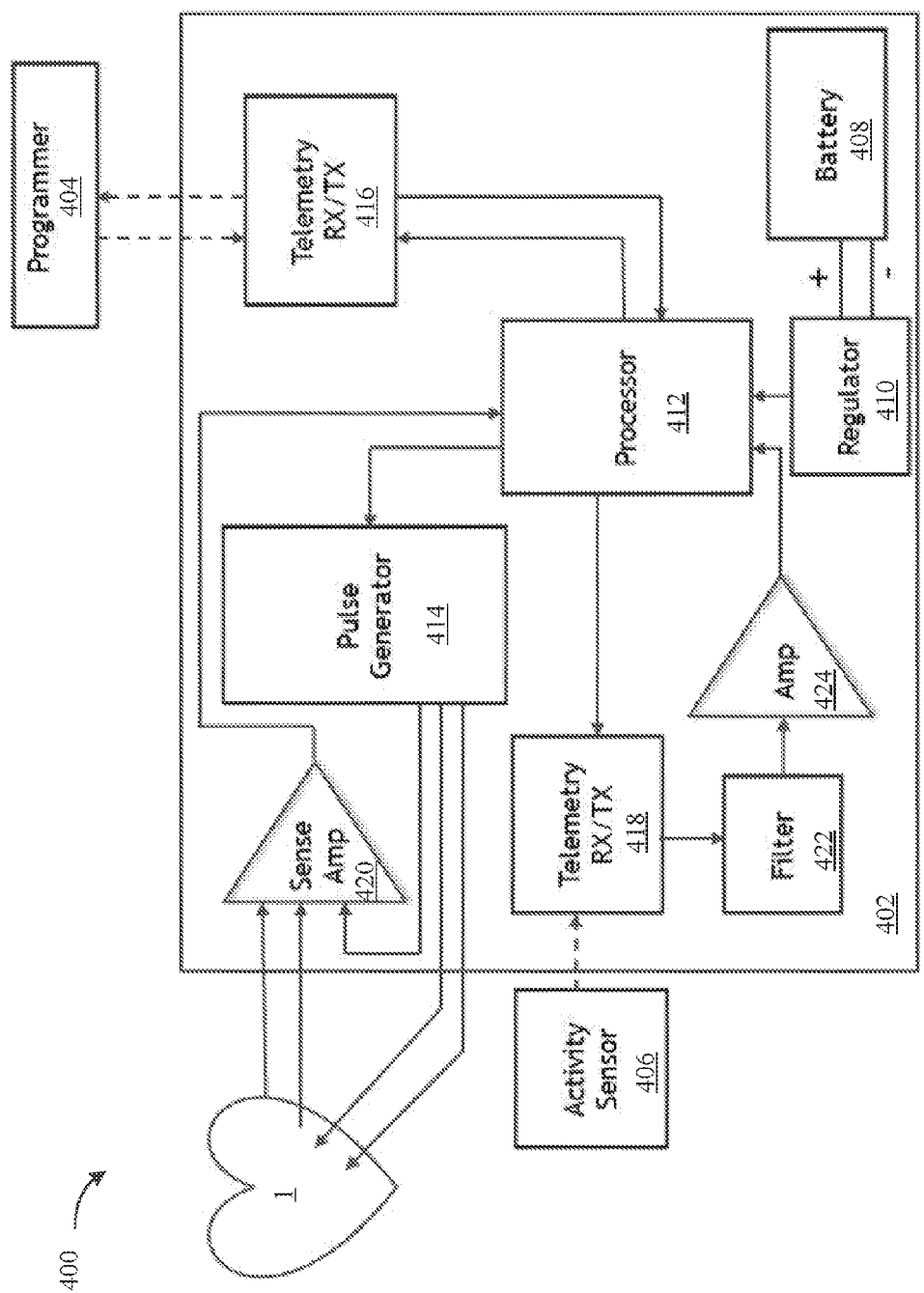
FIG. 37 illustrates an exemplary system diagram according to some embodiments.

FIG. 37 illustrates an exemplary simplified heart stimulation system diagram 400. Heart stimulation system 400 includes a heart stimulation device 402 coupled with heart 1. The heart stimulation device 402 may be communicatively coupled with programmer 404. The heart stimulation device 402 may also be communicatively coupled with activity sensor 406.

Heart stimulation device 402 may be a heart stimulation device described herein (e.g., device 10, 110, 152, 158, 156, 328, or the like). Heart stimulation device 402 may include a battery 408 for powering device 402. Battery 408 may be a lithium battery in many embodiments. The battery 408 may be coupled with regulator 410. The regulator 410 may be coupled with processor 412. The processor 412 may be configured to execute non-transitory computer readable instructions to control the operation of heart stimulation device 402. The processor 412 may be an application-specific integrated circuit (ASIC), for example. The processor 412 may be operatively coupled with and output signals to a pulse generator 414, a telemetry receiver/transmitter circuit or module 416 and a telemetry receiver/transmitter circuit or module 418.

The pulse generator 414 may stimulate the heart 1 (e.g., via one or more electrodes on an attachment side of the heart stimulation device 402) in response to signals from processor 412. The one or more electrodes of the heart stimulation device 402 may also sense signals from the heart 1 and relay the sensed signals to an amplifier 420. Amplifier 420 may also receive signals from pulse generator 414. The amplifier 420 may be configured to amplify received signals (e.g., from the electrodes or the pulse generator) and to output the amplified signals to processor 412.

Telemetry receiver/transmitter 416 may establish two way communication between the stimulation device 402 and the programmer 404. Programmer 404 may be a heart stimulation device programmer 154 or the like. The processor 412 may relay sensed signals to programmer 404 via telemetry receiver/transmitter 416 (e.g., during stimulation device attachment, device diagnostics, etc.). Programmer 404 may transmit preferred operational parameters to the processor 412 via the telemetry receiver/transmitter 416 for stimulating the heart 1. The operational parameters may be selected based on the signals sensed from the heart 1 and the type of desired stimulation/pacing of the heart (e.g., bi-ventricular, dual chamber, defibrillating, etc.).

Telemetry receiver/transmitter 418 may establish communication between the activity sensor 406 and the processor 412. The activity sensor 406 may be activity sensor 320 or the like. The telemetry receiver 418 may receive a signal from the activity sensor 406. The received signal may be processed by filter 422. After filtering, the signal may be amplified by amplifier 424 prior to being received and processed by processor 412. As mentioned above, processor 412 may adjust stimulation and/or pacing of the heart 1 based on signals received from activity sensor 406. For example, when the signal from activity sensor 406 is associated with a decrease in activity of the user, a pacing of the heart 1 may be decreased by the processor 412 as the user may not require as high of a heart rate. Similarly, when the signal from activity sensor 406 is associated with an increase in activity of the user, a pacing of the heart 1 may be increased by the processor 412 as the user may benefit from an increased heart rate to account for the detect increase in activity level of the user (e.g., from resting to walking, or from walking to running, etc.).

It should be understood that system 400 is a simplified and exemplary system schematic of heart stimulation systems according to some embodiments. Further, it should be understood that the borders do not necessarily represent structural borders. For example, heart stimulation device 402 may comprise two or more separate modules for stimulating two or more locations across the heart 1. In some embodiments the two or more separate modules may be wirelessly coupled with one another to provide controlled pacing of different locations of the heart. In some embodiments, the two or more separate modules may be electrically coupled by a flexible tether. Additionally, while illustrated with a single battery 402, and a single pulse generator 414, the device 402 may include multiple batteries 402 and multiple pulse generators as desired. For example, devices comprising two or more modules may be configured such that each module carries a separate battery or such that each module carries separate pulse generators. Accordingly, the system 400 of FIG. 37 is exemplary and non-limiting.

After implantation of a heart stimulation device (and/or an activity sensor), it may be desirable to retrieve or reposition an implanted heart stimulation device in the pericardial space of the patient. Accordingly, some embodiments of the present invention generally relate to recapture devices and methods for detaching and repositioning or removing an implanted device (e.g., a heart stimulation device, activity sensor, or the like).

Figure 38:
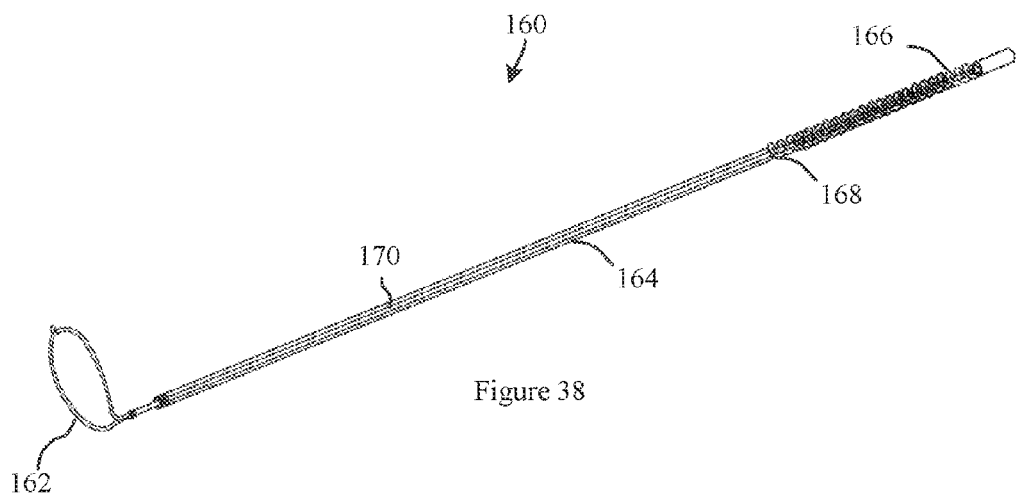
FIG. 38 illustrates a snare device for the recapture of implanted devices according to some embodiments of the present invention.

FIG. 38 illustrates a snare device 160 for the retrieval of implanted devices according to some embodiments of the present invention. Snare device 160 includes an expandable and collapsible snare 162 coupled with a fixed coil 166. A sleeve 164 is provided for locking and unlocking the snare 162 and a rotating coil 168 may be attached to the sleeve 164. Rotating coil 168 and fixed coil 166 may be rotatably engaged to controllably adjust a translation between the rotating coil 168 and the fixed coil 166. Further, the sleeve 164, rotating coil 168, and fixed coil 166 may define a lumen 170 of snare device 160. The rotating coil 168 and the fixed coil 66 may be manufactured with known materials such as stainless steel or Nitinol and configured with similar outside and inside diameters and similar pitches. Therefore, the coils 168 and 166 may be engaged together without adding any additional profile to the engaged portion of the coils. The fixed coil 166 may be attached to the proximal end of the snare 162 and the rotatable coil 168 may be attached to a hypo tube made from stainless steel or nitinol or a polymeric tube made from PEEK or similar material. The rotatable coil and the hypo tube may be rotated clockwise or counter clockwise. After the rotatable coil 166 and the fixed coil 168 are engaged, the rotation of the hypo tube 164 is converted into linear motion of the hypo tube 164 (forward or backward) depending on the direction of the rotation of the hypo tube 164. The linear motion of the hypo tube over the snare 162 may result in reduction or increase in diameter of the snare 162 depending on the direction of the linear movement of the hypo tube 164.

Figure 39:
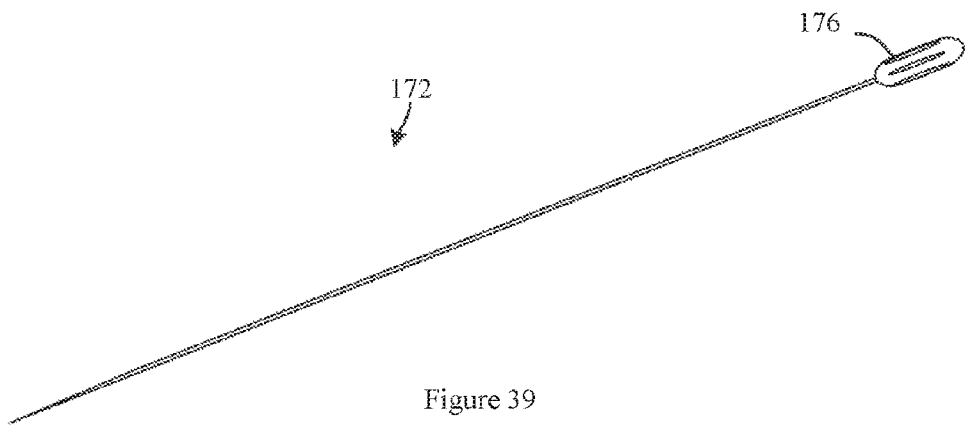
FIG. 39 illustrates a straight stylet for use with the snare device of FIG. 38 according to some embodiments of the invention.

In some embodiments a stylet may be inserted within lumen 170 for steering and/or positioning snare 162 in a desired configuration. For example, FIG. 39 illustrates a straight stylet 172 for use with the snare device 160 of FIG. 38 according to some embodiments of the invention. Straight stylet 172 includes a torque knob 176 on a proximal end of the straight stylet 172. The straight stylet 172 may be inserted into a proximal end of the lumen 170 and into the snare device 160 to provide more rigidity to snare device 160 and to impose a straight configuration for snare device 160 such that snare 162 remains along the axis of snare device 160.

Figure 40:
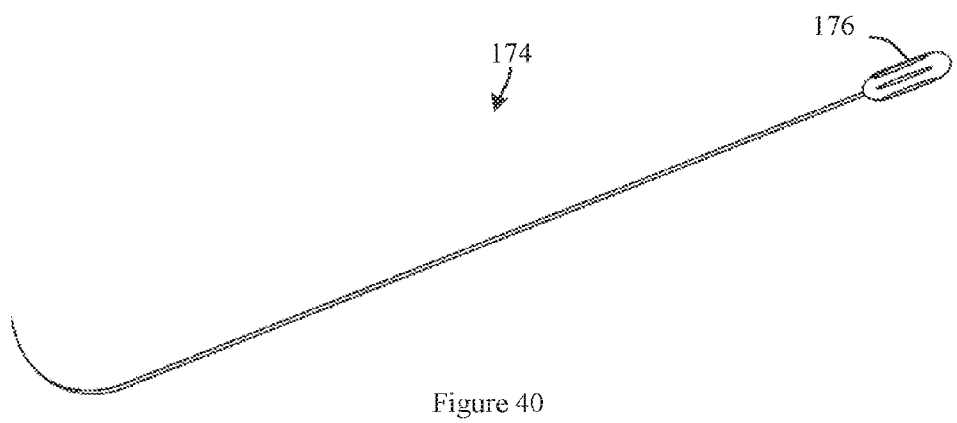
FIG. 40 illustrates a curved stylet for use with the snare device of FIG. 38 according to some embodiments of the invention.

FIG. 40 illustrates a curved stylet 174 for use with the snare device 160 of FIG. 38 according to some embodiments of the invention. Curved stylet 174 includes a torque knob 176 on a proximal end of the curved stylet 174. The curved stylet 174 may be inserted into a proximal end of the lumen 170 and into the snare device 160 to provide more rigidity to snare device 160 and to impose a curved configuration for snare device 160 such that snare 162 is urged off the original axis of snare device 160. The curved stylet 174 may be manufactured with materials such as stainless steel, Nitinol, or the like. The distal curve may be shaped to a curve with a radius from 5-30 mm, for example, preferably about 10 mm.

Figure 41:
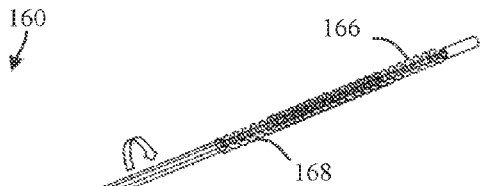
FIG. 41 illustrates the operation of the snare device according to some embodiments of the invention.

FIG. 41 illustrates the operation of the snare device 160 according to some embodiments of the invention. The sleeve 164 and rotating coil 168 may rotate relative to fixed coil 166 to translate the sleeve 174 and rotating coil 168 distally relative to the fixed coil 166 and snare 162 (thereby increasing a length of snare device 160). As the sleeve 164 translates distally relative to fixed coil 166 and snare 162, a distal end of sleeve 164 is advanced over snare 162 and reduces or collapses the loop formed by snare 162. The collapse of the snare 162 may be reversed by reversing the rotation between the rotating coil and the fixed coil 166 so that the sleeve 164 and rotating coil 168 translate in the proximal direction relative to fixed coil 166 (thereby shortening a length of snare device 160). As the sleeve 164 translates proximally relative fixed coil 166 and snare 162, the distal end of sleeve 164 exposes more of the loop of snare 162 such that snare 162 is uncollapsed or expanded. The snare 162 may be made from a super elastic material such as Nitinol wire or cable combined with strands of radiopaque materials such as Tungsten, Platinum, Gold, or the like. The snare 162 may be preshaped to different configurations with a radius from 5-30 mm, for example, preferably about 10 mm. The snare 162 may be configured to different angles with respect to the plane of the shaft 164. The angle between the snare 162 and the shaft 164 may range between 0-270 degrees, for example, preferably about 90 degrees.

Figure 42:
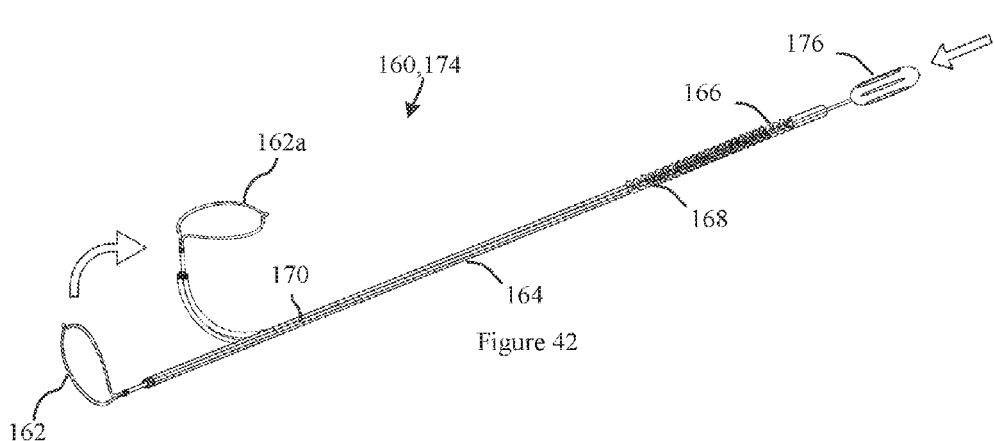
FIG. 42 illustrates the insertion of a curved stylet into the lumen of the snare device of FIG. 38 according to some embodiments of the invention.

FIG. 42 illustrates the insertion of a curved stylet 174 into the lumen 170 of the snare device 160 of FIG. 38 according to some embodiments of the invention. As illustrated, the insertion of curved stylet 174 into lumen 170 of snare device 160 may deflect the distal end of snare device 160 such that snare 162 is repositioned to a curved position 162a. Thereafter the torque knob 176 may be actuated to deflect the distal end of snare device 160 to other positions so as to controllably reposition the snare 162 of snare device 160.

Figure 43:
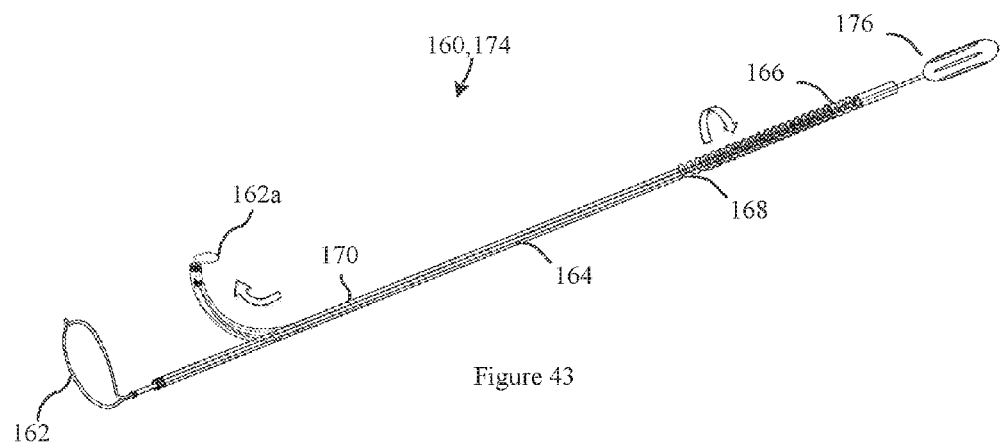
FIG. 43 illustrates the operation of the snare device of FIG. 38 with a curved stylet inserted therein according to some embodiments of the present invention.

FIG. 43 illustrates the operation of the snare device 160 of FIG. 38 with a curved stylet 174 inserted therein. As illustrated, the operation of snare device 160 may be unaffected by the insertion of a stylet therein (e.g., stylet 174). Specifically, the fixed coil 166 and the rotating coil 168 may be actuated to translate the sleeve 164 distally relative to the fixed coil 166. As the sleeve 164 translates distally relative to the fixed coil 166, the sleeve 164 may curve with curved stylet 174 and a distal end of sleeve 164 may advance over snare 162 to controllably collapse, restrict, or otherwise tighten snare 162.

Figures 44, 45:
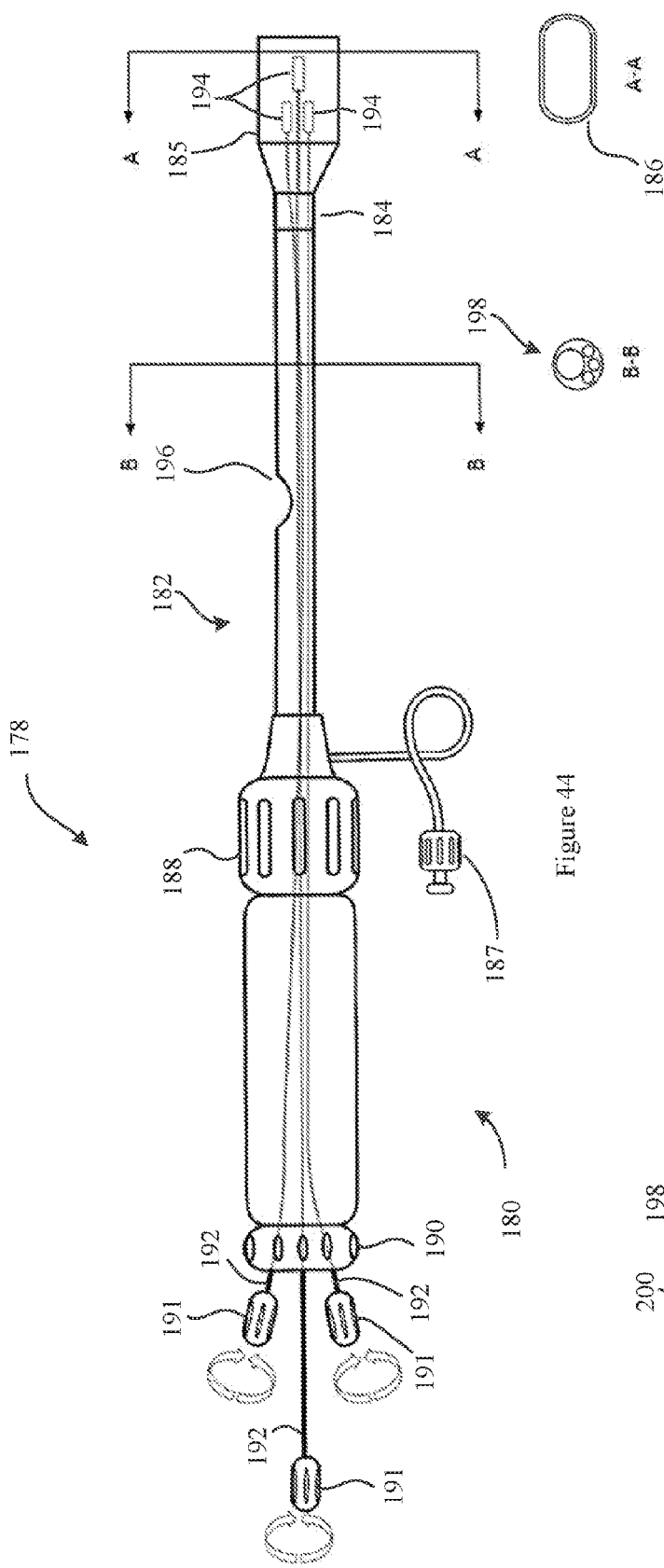
FIG. 44 illustrates a recapture catheter for the recapture of implanted devices according to some embodiments of the present invention.
FIG. 45 illustrates a cross-sectional view of the catheter shaft of FIG. 44 along B-B according to some embodiments of the present invention.

In further embodiments of the invention, a recapture catheter may be provided for detaching, retrieving, and/or repositioning an implanted device. FIG. 44 illustrates a recapture catheter 178 for the detachment, retrieval, and/or repositioning of implanted devices (e.g., heart stimulation devices, activity sensors, or the like) according to some embodiments of the present invention. Recapture catheter 178 may include a handle 180 coupled with a recapture catheter shaft 182 having a distal end 184. Distal end 184 of shaft 182 may include an adaptor 185 with a cross-section 186 (taken along A-A) configured to correspond with and/or fittingly mate with a proximal end (e.g., proximal end 18) of an implantable device (e.g., implantable device 10, activity sensor 320, or the like). Recapture catheter 178 may further include a flush port 187 for flushing the shaft 182 with solution (e.g., saline) during or after catheter 178 advancement into the patient.

Handle 180 may include a deflection controller 188, an implant device engagement controller 190, and one or more anchor retracting controllers 191. Anchor retracting controllers 191 may couple with stylets 192 that extend through the handle 180, through the shaft 182, and through the distal end 184 of the recapture catheter 178. Stylets 192 may terminate at distal ends 194. FIG. 45 illustrates a cross-sectional view of the catheter shaft of FIG. 44 along B-B according to some embodiments of the present invention.

Deflection knob 188 may be configured to deflect shaft 182 in a manner similar to the operation of deflection knob 94 for deflecting shaft 88 of delivery catheter 84. Device engagement controller 190 may be configured to engage an implantable device to secure the device to a distal end 184 of the catheter 178 or to engage with adaptor 185. The device engagement controller 190 may be a knob configured to operate in a manner similar to release knob 96 of catheter 84. For example, the knob 190 may be rotated to actuate a distal engagement feature (not shown) of the recapture catheter 178. The distal engagement feature may have a similar configuration to distal engagement feature 98 of catheter 84. Accordingly, the knob 190 may be turned to engage a screw/coil engagement feature to engage with a threaded channel of the implanted device. In many embodiments, the engagement feature may be configured to engage with a threaded channel (e.g., threaded channel 23) of a proximal button (e.g., proximal button 22) of an implanted device to thereby secure the implant to the recapture device 178.

In some embodiments of the present invention, once the implanted device is engaged with the recapture catheter 178 (e.g., by actuating knob 190 and engaging a distal engagement feature with the implanted device), the adaptor 185 may be configured to engage with and/or mate with the implanted device and may align one or more attachment channels of the implanted device with the distal ends 194 of the stylets 192. Thereafter, the stylets 192 may be advanced distally into the one or more attachment channels by actuating the one or more control knobs 191 (e.g., pushing knobs 191 distally) so as to engage a distal end 194 of stylet 192 with a proximal end of an anchor (e.g., proximal end 42 of anchor 36, 60, 64). In some embodiments the distal end 194 of stylet 192 may have a cross-sectional configuration configured to fittingly mate with a proximal end of an anchor. For example, distal end 194 may have cross-section 103a, 103b, 103c, or the like. After engagement of a distal end 194 of a stylet 192 to a proximal end of an anchor, the control knob 191 may be actuated to retract the anchor from a deployed position to a retracted position. For example, if the anchor is a helical coil, the control knob 191 may be rotated to unscrew the helical coil from the epicardial surface of the heart. In other embodiments, where the anchor is a shape-memory barb, the knob 191 may be pulled proximally to retract the shape-memory barb from the tissue and to transition the barb from the deployed configuration to a retracted and collapsed configuration within the anchor channel. In some embodiments, for example, three anchor controllers 191 may be provided—two may be provided for engaging with and retracting anchors in a proximal module of an implantable device and the third may be advanced through the proximal module, through a tether, and into a distal module for engaging with and retracting an anchor of a distal module.

Shaft 182 may further include an opening 196 where a snare device 60 (with or without a stylet (e.g., stylet 172, 174) inserted therein) may be inserted and advanced distally along the shaft 182. Shaft 192 may have a cross-section 198 along B-B. FIG. 45 illustrates the a close up of the cross-sectional view 198 of the catheter shaft 182 of FIG. 44 along B-B according to some embodiments of the present invention. As illustrated, in some embodiments, the shaft is a multi-lumen shaft 182. The shaft 182 may include lumens 202 for receiving one or more stylets 191 and a lumen 200 for receiving snare device 160. While illustrated with three lumens 202, it should be understood that other embodiments may include more or fewer lumens 202 depending on the number of anchors that need to be engaged and retracted.

Figure 46:
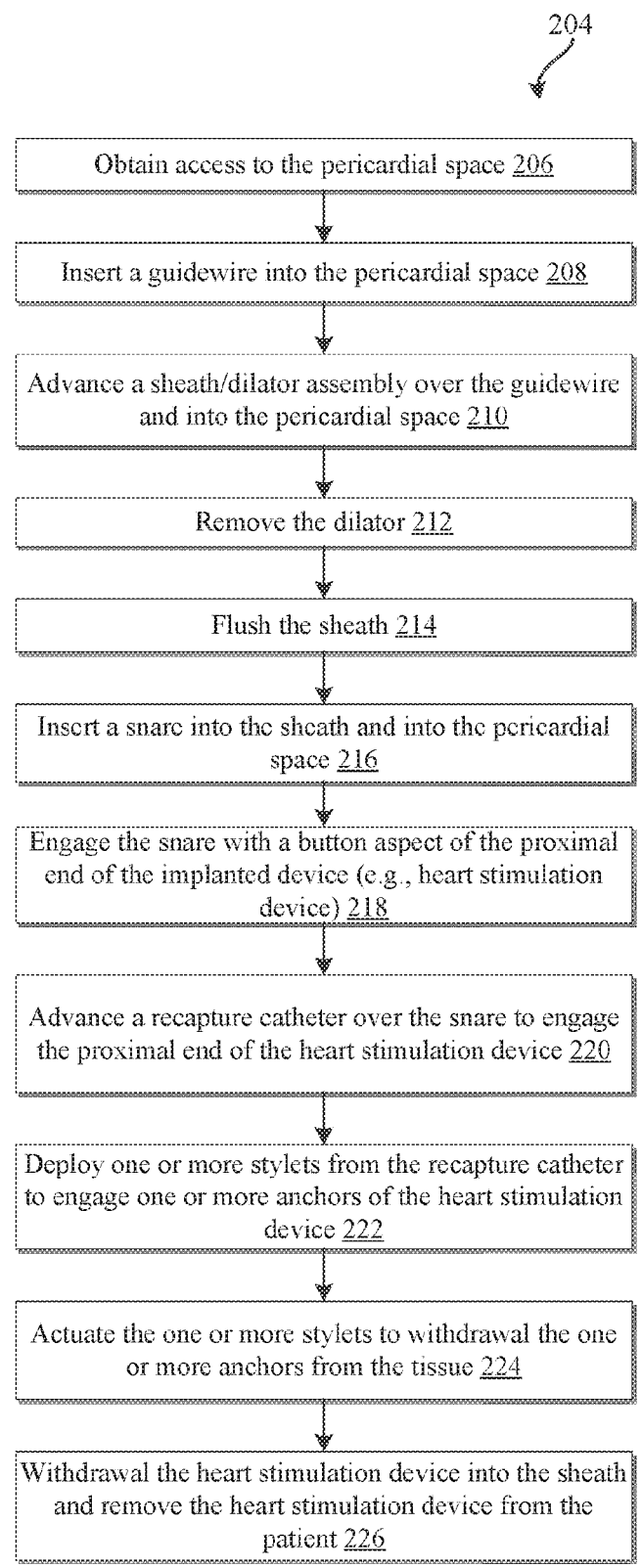
FIG. 46 illustrates an exemplary method of retrieving an implanted device according to some embodiments of the invention.

FIG. 46 illustrates an exemplary method 204 of retrieving an implanted heart stimulation device according to some embodiments of the invention. The method 204 may include obtaining access to the pericardial space 206. Thereafter a guidewire may be inserted into the pericardial space 208. An introducer sheath and/or dilator assembly may be advanced over the guidewire and into the pericardial space 210. The dilator may be removed 121. The sheath may be flushed 214. A snare may be inserted into the sheath and into the pericardial space 216. The snare may be engaged with a button aspect of the proximal end of the heart stimulation device 218. A recapture catheter may be advanced over the snare to engage the proximal end of the heart stimulation device 220. One or more stylets may then be deployed from the recapture catheter to engage one or more anchors of the heart stimulation device 222. Once engaged, the stylets may be actuated to withdrawal the one or more anchors from the tissue 224. After the device becomes detached from the tissue, the device may be withdrawn through the sheath and removed from the patient 226.

FIG. 47 illustrates the use of a recapture catheter-snare assembly 160, 178 for retrieving an implanted device 228 according to some embodiments of the invention. Implanted heart stimulation device 228 may be a pacemaker and/or an ICD device attached to the epicardial surface of a heart 1 of a patient. In FIG. 47, the implanted heart stimulation device 228 comprises a proximal module 230, a distal module 232, and a tether 234 coupling the distal module 232 with the proximal module 230. While heart stimulation device 228 is illustrated and described as having such a configuration, it should be understood that the detachment, removal, or repositioning methods described herein may be utilized with other implantable devices attached to different locations of the patient and having different configurations (e.g., activity level sensor 320).

Access to the pericardial space may be obtained 206 via a subxiphoid surgical approach according to some embodiments. An incision 227 of the pericardium 7 can be made and a guidewire inserted 208 through the incision 227. An introducer sheath 106 may be advanced over the guidewire to provide access to the pericardial space 210. Optionally, a dilator may be used to facilitate the insertion of the introducer sheath 106 into the pericardial space. After the introducer sheath 106 is in place, the dilator may be removed 212. If needed, the introducer sheath 106 may be flushed 214 by introducing solution (e.g., saline) into flush port 108. Accordingly, in some embodiments, methods of detaching, recapturing, or repositioning an implant may avoid a transvascular approach such as a transfemoral implantation method. Further, in some embodiments, methods of implantation may avoid the need for introducing contrast agents into the blood for visualizing a position of the device within the vasculature.

After positioning the introducer sheath 106, a snare device 160 may be inserted into the pericardial space through the sheath 106. Optionally, the snare device 160 may be inserted through the sheath 106 as part of a recapture catheter-snare device 178, 160 assembly or the snare device 160 (with or without a stylet inserted therein (e.g., stylet 172, 174)) may be introduced into the pericardial space separate from a recapture catheter 178.

After the snare device 160 is inserted into the pericardial space, the snare device 160 may be positioned and actuated to engage the snare 162 with a portion of the implanted device 228. For example, the snare 162 may engage with a proximal button of the proximal module 230 of the implanted heart stimulation device 228. FIG. 48 illustrates the engagement of the snare 162 to the implanted device 228 according to some embodiments of the invention. In some embodiments, the snare device 160 may have radiopaque markers at the distal end of the snare device 160 so that engagement of the snare 162 to the implanted device 228 may be guided by fluoroscopy. For example, in some embodiments, portions of snare 162 may be radiopaque. Optionally, the distal end of sleeve 164 may be radiopaque. In other embodiments, engagement of the snare device 160 to the implant 228 may be facilitated using endoscopic techniques or the like. Once, the snare 162 is properly positioned for engaging with the implant 228, the snare device 160 may be actuated by rotating the rotate coil 168 relative the fixed coil 166 to translate the sleeve 164 distally relative to the fixed coil 166. As the sleeve 164 translates distally, the distal end of the sleeve 164 advances over the snare 162 and reduces a diameter of snare 162 to collapse the snare 162 about a portion of implant device 228. In some embodiments, the snare 162 may be reduced over a protrusion of implant 228 such as a proximal button on a proximal end of the implant heart stimulation device 228.

After engagement of the snare device 160 to the implanted device 228, the recapture catheter 178 may be advanced over the snare 160 to engage the proximal module 230 of the implanted device 228. In some embodiments, an adaptor (e.g., adaptor 185) may be provided on the distal end 184 of recapture catheter 178 to engage with and/or align a distal end 184 of the recapture catheter 178 with a proximal end of the implant 228. Advantageously, alignment of the recapture catheter 178 with the implant 228 during device 228 detachment, repositioning, or removal may facilitate the advancement of one or more stylets 190 from the recapture catheter 178 and into an attachment channel of the implant device 228 for engagement with one or more anchors 222 of the device 228. For example, the distal openings of lumens 202 of recapture catheter 178 may be configured to align with attachment channels of an implant (e.g., implant 228) when the implant is engaged by adaptor 185. Accordingly, with the lumens 202 of recapture catheter 178 aligned with attachment channels of the device, stylets 190 may be pushed distally from the recapture catheter 178 to advance from the lumens 202 into the attachment channels to engage a distal end 194 of the stylets 190 with a proximal end of the deployed anchors of the device 228. In the illustrated embodiment, the recapture device may include three stylets 190. Two stylets may be advanced into attachment channels of the proximal module 230 of the device 228 to engage anchors of the proximal module 230. Another stylet 190 may be advanced in an attachment channel that extends through the proximal module 230, through the tether 234 and into an attachment channel of the distal module 232 to engage an anchor of the distal module 232.

After the distal ends 194 of the stylets 190 are operatively coupled with the proximal end of the deployed anchors of device 228, the one or more anchor control knobs 191 may be actuated to withdrawal the one or more anchors from the tissue 224. For example, if the anchors are helical anchors, the control knobs 191 may be retract and withdrawal the helical anchors from the tissue. If the anchors are shape-memory barbs (e.g., barb 64), the control knobs 191 may be pulled proximally to withdrawal the anchors and to reconfigure the anchors from a deployed configuration (e.g., deployed configuration 68) to a collapsed configuration (e.g., collapsed configuration 66) within the attachment channel.

Once the anchors are withdrawn to a retracted position, the device 228 may be disengaged from the epicardial surface of the heart 1. Thereafter, the device may be repositioned to another attachment location (e.g., by testing pacing and sensing thresholds over the epicardial surface, identifying a preferred location, and deploying the anchors into the tissue by actuating the one or more stylets) or may be removed from the pericardial space of the patient. FIG. 49 illustrates the removal of the implanted heart stimulation device 228 through the introducer sheath 106 using the recapture catheter 178 according to some embodiments of the invention.

Figure 50:
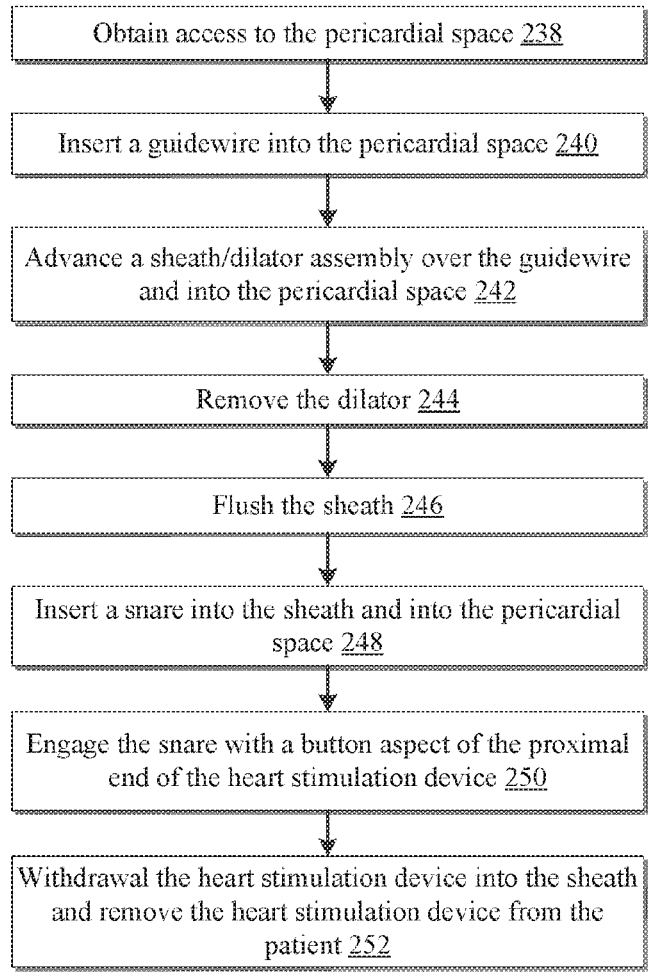
FIG. 50 illustrates an exemplary method of removing the implanted device using the snare device without a recapture catheter according to some embodiments of the invention.

FIG. 50 illustrates an exemplary method 236 of removing the implanted heart stimulation device using the snare device 160 without a recapture catheter 178 according to some embodiments of the invention. Method 236 may start by obtaining access to the pericardial space 238. A guidewire may be inserted into the pericardial space 240. An introducer sheath and/or dilator may be advanced over the guidewire and into the pericardial space 242. The dilator may be removed thereafter 244. The introducer sheath may be flushed 246. A snare may be inserted through the introducer sheath and into the pericardial space 248. The snare device may engage with a portion of the implanted device 250. The implanted device 250 may then be withdrawn from the pericardial space and through the introducer sheath to remove the heart stimulation device from the patient 252.

Figure 53:
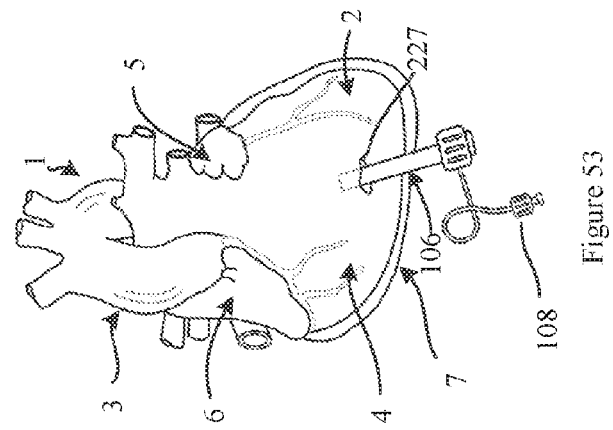
FIG. 53 illustrates the removal of the implanted device through the introducer sheath using the snare device according to some embodiments of the invention.
Figure 52:
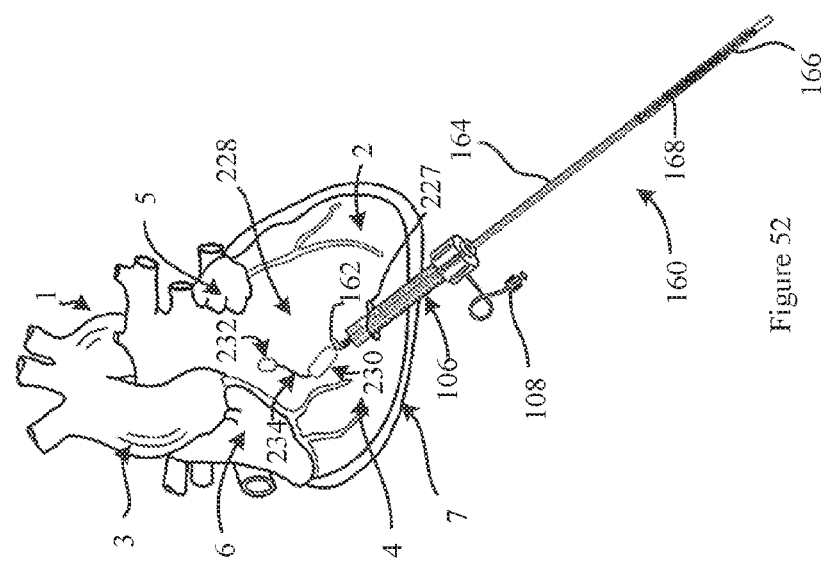
FIG. 52 illustrates the engagement of the snare device to the implanted device for device removal according to some embodiments of the invention.
Figure 51:
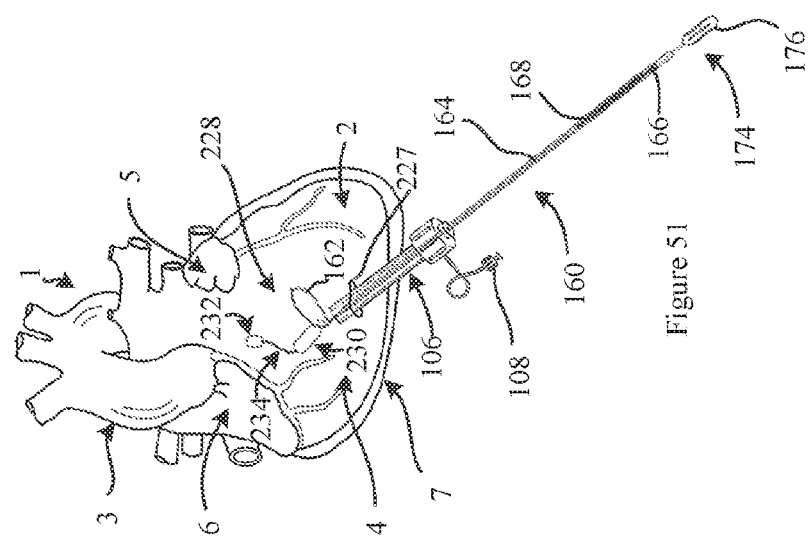
FIG. 51 illustrates the use of a snare device to remove an implanted device according to some embodiments of the present invention.

The pericardial space may be accessed 238 by the methods described above (e.g., by subxiphoid surgical approach, without transvascular approach, and without contrast agents). Additionally the steps of positioning the introducer sheath (e.g., steps 240, 242, 244, 246) may also be carried out in a manner similar to that described above. FIG. 51 illustrates the use of a snare device 160 to remove an implanted device 228 without the use of a recapture catheter 178 according to some embodiments of the present invention. The snare device 160 may be inserted along the axis of introducer sheath 160 and into the pericardial space. Optionally a straight stylet 174 may be inserted within lumen 170 of snare device 160. After positioning the snare 162 about a portion of the implanted heart stimulation device 228, optionally under endoscopic or fluoroscopic guidance, the snare 162 may engage with the device by rotating coils 166, 168 and translating sleeve 164 in a distal direction such that a distal end of sleeve 164 advances over the snare 162 to collapse the snare 162 over a portion of the implanted device 228. FIG. 52 illustrates the engagement of the snare device 160 to the implanted device 228 for heart stimulation device 228 removal according to some embodiments of the invention. After engagement with the snare device 160 to the implanted device 228, the snare device 160 may urge the implanted device 228 away from the epicardial surface of the heart 1 to detach the device 228 from the heart 1. After detachment, the device 228 may be removed from the pericardial space of the patient. FIG. 53 illustrates the removal of the implanted device 228 through the introducer sheath 106 using the snare device 160 according to some embodiments of the invention.

The method 236 may be employed when, for example, the device 228 does not use anchors and adheres to the epicardial surface of the heart 1 using a polymer mesh (e.g., polymer mesh 74) and a surgical glue 80. In some embodiments, the method may be employed when, for example, the device 228 uses shape-memory barbs that may be withdrawn from the tissue by urging the device 228 away from the epicardial surface of the heart 1 using the snare device 160. In other embodiments, the method 236 may be used even when the device 228 attaches to the epicardial surface of the heart 1 using anchors and when trauma to the epicardial surface of the heart tissue is determined to be minimal.

While the removal methods are illustrated and discussed specifically for heart stimulation devices, it should be understood that the methods and devices may be applicable to attached activity level sensors. For example, when removing or repositioning an activity level sensor that is attached to a location other than the heart of the patient (e.g., the inner surface of the sternum, or the like), it should be understood that there may be no need to access the pericardial space of the patient. In some embodiments, a snare device alone may be used to retrieve an activity level sensor. In some embodiments, a snare device and retrieval catheter may be used in combination for retrieving an activity level sensor.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. An epicardial heart stimulation device system, comprising:
   a delivery catheter comprising a handle coupled with a catheter shaft having a distal end;
   a heart stimulation device releaseably coupled to the distal end of the catheter shaft by an engagement feature, the heart stimulation device comprising a first anchor channel housing an anchor therein, the first anchor channel terminating at an opening on an attachment side of the heart stimulation device;
   wherein the delivery catheter further comprises:
   a heart stimulation device release controller for actuating the engagement feature of the delivery catheter to selectively disengage the heart stimulation device from the distal end of the catheter shaft;
   a first anchor controller for actuating a first stylet to control the deployment of the heart stimulation device anchor disposed in the first anchor channel, the first stylet extending down the catheter shaft and engaging with the anchor housed in the first anchor channel of the heart stimulation device;
   wherein the heart stimulation device comprises a proximal module coupled to a distal module by a tether, the distal end of the catheter shaft releaseably coupled with the proximal module at an attachment end of the proximal module and the distal module extending cantilever from the distal end of the catheter shaft.

2. The epicardial heart stimulation device system of claim 1, wherein the first anchor channel is disposed within the proximal module and terminates on the attachment side of the proximal module; wherein the distal module comprises a second anchor channel housing an anchor therein, the second anchor channel terminating at an opening on an attachment side of the distal module; and wherein the second anchor channel extends through the tether and through the proximal module to the attachment end of the proximal module; the proximal module including a first electrode on the attachment side of the proximal module and the distal module including a second electrode on the attachment side of the distal module, wherein the delivery catheter further comprises a second anchor controller for actuating a second stylet to control the deployment of the heart stimulation device anchor disposed in the second anchor channel, the second stylet extending down the catheter shaft and engaging with the anchor housed in the second anchor channel of the heart stimulation device.

3. The epicardial heart stimulation device system of claim 1, wherein the delivery catheter further comprises a shaft deflection controller for deflecting the catheter shaft and a distal module steering controller for separately deflecting the distal module relative to the proximal module.

4. An epicardial heart stimulation device implantation kit comprising a guidewire for insertion into a pericardial space of a patient, an introducer sheath for advancement over the guidewire and into the pericardial space; and the epicardial heart stimulation device system of claim 1 for delivery of the heart stimulation device to the pericardial space through the introducer sheath.

5. An epicardial heart stimulation device implantation kit comprising the epicardial heart stimulation device system of claim 1 and an activity level sensor for implantation within the patient, the activity level sensor communicatively coupled with the heart stimulation device to provide activity level data, and wherein the heart stimulation device adjusts pacing of the epicardial surface of the heart based on activity level data received from the activity level sensor.

6. The epicardial heart stimulation device implantation kit of claim 5, wherein the activity level sensor comprises an accelerometer and wherein the activity level data comprises accelerometer data.

7. The epicardial heart stimulation device system of claim 1, wherein the heart stimulation device comprises a pacemaker.

8. The epicardial heart stimulation device system of claim 1, wherein the heart stimulation device comprises an implantable cardioverter-defibrillator.

9. The epicardial heart stimulation device system of claim 1, wherein a heart attachment side of the proximal module is concave and couples with the epicardial surface of the heart in a direction transverse to a length of the proximal module and wherein a heart attachment side of the distal module is concave and couples with the epicardial surface of the heart in a direction transverse to a length of the distal module.

10. The epicardial heart stimulation device system of claim 1, wherein only one of the proximal module and the distal module comprises a battery for powering both the proximal module and the distal module.

\* \* \* \* \*